United States Patent
Yamakawa et al.

(10) Patent No.: US 7,935,712 B2
(45) Date of Patent: *May 3, 2011

(54) SPIROCHROMANONE DERIVATIVES AS ACETYL COENZYME A CARBOXYLASE (ACC) INHIBITORS

(75) Inventors: Takeru Yamakawa, Tsukuba (JP); Hideki Jona, Moriya (JP); Kenji Niiyama, Tsuchiura (JP); Koji Yamada, Tsuchiura (JP); Tomoharu Iino, Tsukuba (JP); Mitsuru Ohkubo, Ushiku (JP); Hideaki Imamura, Ryugasaki (JP); Jun Shibata, Tsukuba (JP); Jun Kusunoki, Tsukuba (JP); Lihu Yang, Edison, NJ (US)

(73) Assignees: Merck Sharp & Dohme Corp., Rahway, NJ (US); MSD K.K., Tokyo (JP)

( * ) Notice: Subject to any disclaimer, the term of this patent is extended or adjusted under 35 U.S.C. 154(b) by 471 days.

This patent is subject to a terminal disclaimer.

(21) Appl. No.: 11/988,588

(22) PCT Filed: Jul. 14, 2006

(86) PCT No.: PCT/US2006/027543

§ 371 (c)(1),
(2), (4) Date: Jan. 10, 2008

(87) PCT Pub. No.: WO2007/011809

PCT Pub. Date: Jan. 25, 2007

(65) Prior Publication Data

US 2009/0131464 A1   May 21, 2009

Related U.S. Application Data

(60) Provisional application No. 60/700,382, filed on Jul. 19, 2005.

(51) Int. Cl.
*A01N 43/42* (2006.01)
*A61K 31/44* (2006.01)
*A61K 31/535* (2006.01)

(52) U.S. Cl. .................. 514/278; 514/229.5; 514/229.8

(58) Field of Classification Search ............... 514/229.5, 514/229.8, 278

See application file for complete search history.

(56) References Cited

U.S. PATENT DOCUMENTS

| | | | | |
|---|---|---|---|---|
| 5,206,240 A | * | 4/1993 | Baldwin et al. | 514/231.5 |
| 5,563,716 A | * | 10/1996 | Shibayama et al. | 386/68 |
| 5,633,247 A | * | 5/1997 | Baldwin et al. | 514/210.2 |
| 5,885,999 A | | 3/1999 | Elliott et al. | |
| 7,410,976 B2 | * | 8/2008 | Yamakawa et al. | 514/278 |
| 2008/0171761 A1 | * | 7/2008 | Iino et al. | 514/278 |
| 2009/0270436 A1 | * | 10/2009 | Iino et al. | 514/278 |

FOREIGN PATENT DOCUMENTS

| | | | |
|---|---|---|---|
| EP | 0004624 | | 3/1979 |
| EP | 0431943 | * | 12/1990 |
| JP | 2003/059871 | * | 7/2003 |
| JP | 2003/059886 | * | 7/2003 |
| JP | 2003/094912 | * | 11/2003 |
| JP | 2004/092179 | * | 10/2004 |
| JP | 2005-119987 | | 12/2005 |
| WO | WO 94/17045 | | 8/1994 |
| WO | 95/30642 | * | 11/1995 |
| WO | WO 95/30642 | | 11/1995 |
| WO | 96/39140 | * | 12/1996 |
| WO | WO 96/39140 | | 12/1996 |
| WO | 03/072197 | * | 9/2003 |
| WO | WO 2004/092179 | | 10/2004 |
| WO | WO 2006/055752 | | 5/2006 |

OTHER PUBLICATIONS

H. James Harwood, Treating the Metabolic Syndrome: Acetyl-CoA Carboxylase Inhibition, 9 Expert Opin. Ther. Targets 267 (2005).*
H. James Harwood, et al, Isozyme-nonselective N-substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals, 39 J Bio. Chem. 37099 (Sep. 26, 2003).*
Database Chemcats Abstract. XP002407688, CAS-registry No. 877811-12-6, 877811-11-5 & "Interchim Intermediates", Jan. 18, 2005.

* cited by examiner

*Primary Examiner* — Jeffrey S. Lundgren
*Assistant Examiner* — Sean Basquill
(74) *Attorney, Agent, or Firm* — Janet E. Fair; John C. Todaro

(57) ABSTRACT

The invention relates to a compound of a formula (I): or a pharmaceutically acceptable salt or ester thereof, useful as a therapeutic agent for various ACC-related disorders.

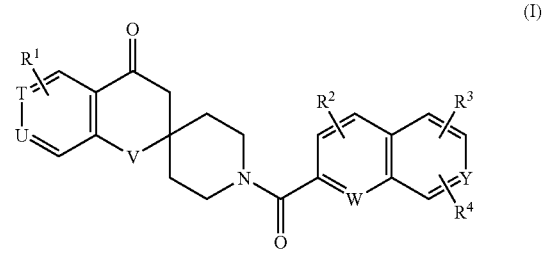

2 Claims, No Drawings

SPIROCHROMANONE DERIVATIVES AS ACETYL COENZYME A CARBOXYLASE (ACC) INHIBITORS

CROSS-REFERENCE TO RELATED APPLICATIONS

This application is a U.S. National Phase application under 35 U.S.C. §371 of PCT Application No. PCT/US2006/027543, filed 14 Jul. 2006, which claims priority from and the benefit of U.S. Provisional Application No. 60/700,382, filed Jul. 19, 2005.

BACKGROUND OF THE INVENTION

Acetyl CoA carboxylase (ACC) is an enzyme that carboxylates acetyl CoA to produce malonyl CoA, and mammals have two isozymes of ACC1 and ACC2 in their own bodies. Malonyl CoA produced by ACC may be a starting material for long-chain fatty acids or triglycerides, and in addition, it may negatively control carnitine palmitoyl transferase-1 (CPT-1) which participates in oxidative decomposition of fatty acids. Of the above isozymes, ACC1 exists in cytoplasm and is considered as a rate-limiting enzyme in biosynthesis of long-chain fatty acids; while ACC2 exists predominately in mitochondria and is said to participate principally in oxidation of fatty acids. Accordingly, compounds capable of inhibiting ACC1 and/or ACC2 are expected not only to inhibit synthesis of fatty acids but also to reduce accumulated fat. It is known that high cellular fat and fatty acids, as well as malonyl CoA which is generated by ACC2, induce insulin resistance in animals and play an important role in type 2 diabetes. In fact, it was shown that, as compared with normal mice which became obese and diabetic on a high fat/high carbohydrate diet, ACC2-knock out mice on a high fat/high carbohydrate diet had reduced obesity due to increased fatty acid oxidation and reduced fat storage, remained insulin sensitive, and did not develop diabetes. (see *Proceedings of the National Academy of Sciences of the United States of America*, 100 (18), pp. 10207-10212, 2003; Science, Vol. 291, pp 2613-2616 (2001)).

An excess of accumulated fat may cause, for example, insulin resistance, diabetes, hypertension, hyperlipemia and obesity, and it is known that a plurality of those factors, as combined, lead to a higher risk of arteriosclerosis and metabolic syndrome. Further, it is known that hypertriglyceridemia or obesity leads to a higher risk of, for example, pancreatitis, hepatic dysfunction, cancers such as breast cancer, uterine cancer, ovarian cancer, colon cancer and prostate cancer, emmeniopathy, arthritis, gout, cholecystitis, gastroesophageal reflux, Pickwickian syndrome, and sleep apnea syndrome. It is well known that diabetes often causes, for example, cardiac angina, heart failure, stroke, claudication, retinopathy, eyesight failure, renal failure, neuropathy, skin ulcer, infectious diseases (see *The Merck Manual of Medical Information*, second home edition, Merck & Co., 2003). Accordingly, ACC inhibitors are useful for the treatment and/or prevention of such disorders.

ACC exists also in plants, parasites, bacteria and fungi, and participates in the growth of cells. For example, aryloxyphenoxypropionic acid-type herbicides represented by diclofop, and cyclohexanedione-type herbicides represented by sethoxydim exert their activity by inhibiting ACC in plants (see Biochemical Society Transaction, 22(3), p. 616 (1994)), and aryloxyphenoxypropionic acid also exhibits a growth-inhibiting effect on parasites (see Journal of Biological Chemistry, 277 (26), pp. 23208-23215 (2002)). Soraphen and moiramide B, known ACC inhibitors, exhibit an antibacterial effect and an antifungal effect (see Current Genetics, 25 (2), pp. 95-100 (1994); Journal of Biological Chemistry, 279 (25), pp. 26066-26073 (2004)).

Tumor cells generally show an increased synthesis of fatty acids, and it is reported that some fatty acid synthesis inhibitors exhibit a cell growth-inhibiting effect.

Based on the above-mentioned information, ACC inhibitors are expected to be useful for the treatment and/or prevention of disorders such as hyperlipemia, dyslipidemia, hepatic steatosis, hepatic dysfunction, non-alcoholic fatty liver disease, obesity, diabetes, insulin resistance, metabolic syndrome, arteriosclerosis, hypertension, cardiac angina, heart failure, cardiac infarction, stroke, claudication, retinopathy, eyesight failure, renal failure, electrolyte abnormality, neuropathy, skin ulcer, bulimia, pancreatitis, emmeniopathy, arthritis, gout, cholecystitis, gastroesophageal reflux, Pickwickian syndrome, sleep apnea syndrome, infectious diseases, neoplasia, and also as herbicides.

There still remains a need for potent low molecular weight ACC1 and ACC2 inhibitors that have pharmacokinetic and pharmacodynamic properties suitable for use as human pharmaceuticals.

Up to the present, for example, those described in WO 2003/094912, WO 2003/072197, WO 2003/059886, and WO 2003/059871 are known as compounds capable of inhibiting ACC, but the compounds described in these references are structurally distinct from the compounds of the present invention.

On the other hand, various compounds having a spirochromanone skeleton are disclosed in U.S. Pat. Nos. 5,206,240, 5,633,247, JP2005119987A, EP 431973A, EP 004624 A2, WO 94/17045, WO 95/30642, WO 96/39140, and WO 2004/092179. However, these references neither disclose nor suggest the ACC-inhibiting effect of the compounds disclosed therein or of the compounds of the present invention.

SUMMARY OF THE INVENTION

Novel spirochromanone derivatives of the invention are acetyl coenzyme A carboxylase (ACC) inhibitors useful as therapeutic agents for various vascular diseases, nervous system diseases, metabolic diseases, genital diseases, digestive system diseases, respiratory diseases, neoplasm and infectious diseases. In addition, they are also useful as herbicides.

DETAILED DESCRIPTION OF THE INVENTION

The present invention provides compounds of the following general formula (I), and salts and esters thereof, which have a strong ACC-inhibiting effect:

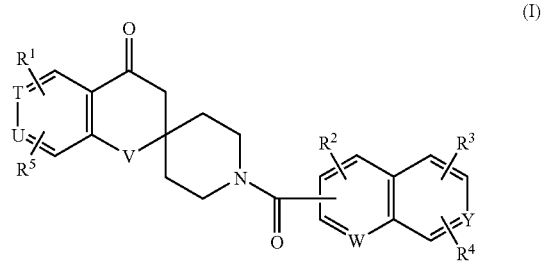

(wherein $R^1$ and $R^5$ each independently represent a hydrogen atom, a halogen atom, a cyano group, a lower alkenyl group, a lower alkoxy group, a lower alkanoyl group, a lower alkoxycarbonyl group, an aralkyloxycarbonyl group, a carbamoyl-lower alkoxy group, a carboxy-lower alkenyl group, or a group of -$Q^1$-N($R^a$)-$Q^2$-$R^b$, a lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$, or a lower alkyl or alkenyl group having the said aryl or heterocyclic group;

$R^2$, $R^3$ and $R^4$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a hydroxy-lower alkoxy group, a lower alkoxy-lower alkoxy group, a cyclo-lower alkyloxy group, a cyclo-lower alkyl-lower alkoxy group, a lower alkylthio group, a group of —O—$R^k$ or a group of —N($R^e$)$R^f$, or a lower alkoxy group substituted by the group of —N($R^e$)$R^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower alkyl group, a lower alkenyl group, a lower alkoxy group, a halo-lower alkoxy group and a lower alkylthio group;

$Q^1$ and $Q^2$ each independently represent a single bond, or a group of —CO—, —$SO_2$— or —C($R^g$)($R^h$)—, when $Q^2$ represents the group of —C($R^g$)($R^h$)—, $R^a$ and $R^g$, taken together, may represent a group of -$Q^1$-N=C($R^h$)—$R^b$;

$R^a$ and $R^b$ each independently represent a hydrogen atom, a lower alkenyl group, a lower alkoxy group, a halo-lower alkoxy group, an aralkyloxy group, a carbamoyl group, a lower alkoxycarbonyl group or a group of —N($R^i$)$R^j$, or a lower alkyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group;

$R^c$, $R^d$, $R^g$, $R^h$, $R^i$ and $R^j$ each independently represent a hydrogen atom, a lower alkyl group, or a halo-lower alkyl group;

$R^e$ and $R^f$ each independently represent a hydrogen atom, a lower alkyl group or a halo-lower alkyl group, or taken together, they may form a lower alkylene group optionally interrupted by an oxygen atom, a sulfur atom or an imino group;

$R^k$ represents a pyrrolidinyl, tetrahydrofuranyl, piperidyl group optionally substituted by a lower alkyl group or a halo-lower alkyl group;

T, U, W and Y each independently represent a nitrogen atom or a methine group; and V represents an oxygen atom or a sulfur atom);

or salt or ester thereof.

The compounds of formula (I) of the invention have an ACC-inhibiting effect and are useful as therapeutic agents for various ACC-related disorders, for example, vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy and sexual dysfunction; digestive system diseases such as liver dysfunction, pancreatitis, cholecystitis and gastroesophageal reflux; respiratory diseases such as Pickwickian syndrome and sleep apnea syndrome; infectious diseases caused by bacteria, fungi or parasites; malignant neoplasm; and inflammatory diseases such as arthritis and skin ulcer. The compounds of formula (I) are also useful as herbicides. In particular, the compounds of formula (I) of the invention are useful as therapeutic agents, for example, for metabolic syndrome, fatty liver, hyperlipemia, obesity, diabetes, bulimia, malignant neoplasm and infectious diseases.

The invention relates to the compounds of formula (I), and their salts and esters, and to their production and use.

The meanings of the terms used herein are mentioned below, and the invention is described in more detail hereinunder.

"Halogen atom" includes a fluorine atom, a chlorine atom, a bromine atom, and an iodine atom.

"Lower alkenyl group" means a linear or branched alkenyl group having from 2 to 6 carbon atoms, and it includes, for example, a vinyl group, a 1-propenyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, and a 4-pentenyl group.

"Lower allyl group" means a linear or branched alkyl group having from 1 to 6 carbon atoms, and it includes, for example, a methyl group, an ethyl group, a propyl group, an isopropyl group, a butyl group, an isobutyl group, a sec-butyl group, a tert-butyl group, a pentyl group, an isopentyl group, a hexyl group, and an isohexyl group.

"Lower alkanoyl group" means an alkanoyl group having the above-mentioned lower alkyl group, or that is, an alkanoyl group having from 2 to 7 carbon atoms, and it includes, for example, an acetyl group, a propionyl group, a butyryl group, an isobutyryl group, a valeryl group, an isovaleryl group, and a pivaloyl group.

"Lower alkoxy group" means a linear or branched alkoxy group having from 1 to 6 carbon atoms, and it includes, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, and an isohexyloxy group.

"Lower alkoxycarbonyl group" means an alkoxycarbonyl group having the above-mentioned lower alkoxy group, or that is, an alkoxycarbonyl group having from 2 to 7 carbon atoms, and it includes, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, and a pentyloxycarbonyl group.

"Aralkyl group" means the above-mentioned lower alkyl group which is substituted by the above-mentioned aryl group and which has one, two or more, but preferably one unlimited substitutable position, and it includes, for example, a benzyl group, a 1-phenylethyl group, a phenethyl group, a 1-naphthylmethyl group, and a 2-naphthylmethyl group.

"Aralkyloxy group" means an aralkyloxy group having the above-mentioned aralkyl group, and it includes, for example, a benzyloxy group, a 1-phenylethyloxy group, a phenethyloxy group, a 1-naphthylmethyloxy group, and a 2-naphthylmethyloxy group.

"Aralkyloxycarbonyl group" means an aralkyloxycarbonyl group having the above-mentioned aralkyloxy group, and it includes, for example, a benzyloxycarbonyl group, a 1-phenylethyloxycarbonyl group, a phenethyloxycarbonyl group, a 1-naphthylmethyloxycarbonyl group, and a 2-naphthylmethyloxycarbonyl group.

"Carbamoyl-lower alkoxy group" means the above-mentioned lower alkoxy group which is substituted by carbamoyl group(s) and which has one, two or more, but preferably one unlimited substitutable position, and it includes, for example, a carbamoylmethoxy group, a 1-carbamoylethoxy group, a 2-carbamoylethoxy group, a 2-carbamoylpropoxy group, and a 3-carbamoylpropoxy group.

"Carboxy-lower alkenyl group" means the above-mentioned lower alkenyl group which is substituted by carboxyl group(s) and which has one, two or more, but preferably one unlimited substitutable position, and it includes, for example, a 1-carboxyvinyl group, a 2-carboxyvinyl group, a 2-carboxy-1-propenyl group, a 3-carboxy-1-propenyl group, a 3-carboxy-2-propenyl group, a 4-carboxy-3-butenyl group, and a 4-carboxy-2-butenyl group.

"Halo-lower alkoxy group" means the above-mentioned lower alkoxy group which is substituted by the above-mentioned halogen atom(s) of the same type or different types and which has one, two or more, but preferably from 1 to 3 unlimited substitutable positions, and it includes, for example, a fluoromethoxy group, a difluoromethoxy group, a trifluoromethoxy group, a 2-fluoroethoxy group, a 1,2-difluoroethoxy group, a chloromethoxy group, a 2-chloroethoxy group, a 1,2-dichloroethoxy group, a bromomethoxy group, and an iodomethoxy group.

"Lower alkylthio group" means a linear or branched alkylthio group having from 1 to 6 carbon atoms, and it includes, for example, a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group, and an isohexylthio group.

"Lower alkanoyloxy group" means an alkanoyloxy group having the above-mentioned lower alkanoyl group, and it includes, for example, an acetyloxy group, a propionyloxy group, a butyryloxy group, an isobutyryloxy group, a valeryloxy group, an isovaleryloxy group, and a pivaloyloxy group.

"Lower alkylsulfonyl group" means a linear or branched alkylsulfonyl group having from 1 to 6 carbon atoms, and it includes, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, and an isohexylsulfonyl group.

"Halo-lower alkyl group" means the above-mentioned lower alkyl group which is substituted by the above-mentioned halogen atom(s) of the same type or different types and which has one, two or more, but preferably from 1 to 3 unlimited substitutable positions, and it includes, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group.

"Hydroxy-lower alkyl group" means the above-mentioned lower alkyl group which is substituted by hydroxyl group(s) and which has one, two or more, but preferably one or two unlimited substitutable positions, and it includes, for example, a hydroxymethyl group, a 2-hydroxyethyl group, a 1-hydroxy-1-methylethyl group, a 1,2-dihydroxyethyl group, and a 3-hydroxypropyl group.

"Lower alkanoyloxy-lower alkyl group" means the above-mentioned lower alkyl group which is substituted by the above-mentioned lower alkanoyloxy group and which has one, two or more, but preferably one unlimited substitutable position, and it includes, for example, an acetyloxymethyl group, a propionyloxymethyl group, a butyryloxymethyl group, an isobutyryloxymethyl group, a valeryloxymethyl group, an isovaleryloxymethyl group, and a pivaloyloxymethyl group.

"Aryl group" includes, for example, a phenyl group, and a naphthyl group.

"Heteroaromatic group" means a 5-membered or 6-membered monocyclic heteroaromatic group which has one, two or more, but preferably from 1 to 3 and the same or different hetero atoms selected from a group consisting of oxygen, nitrogen and sulfur atoms, or means a condensed-cyclic heteroaromatic group which is constructed through condensation of the monocyclic heteroaromatic group and the above-mentioned aryl group or through condensation of those, same or different monocyclic heteroaromatic groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a, 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, and a pyrido[3,2-b]pyridyl group.

"Heterocyclic group" means a 3- to 7-membered monocyclic heterocyclic group which has one, two or more, but preferably from 1 to 3 and the same or different hetero atoms selected from a group consisting of oxygen, nitrogen and sulfur atoms, or means a condensed-cyclic heterocyclic group which is constructed through condensation of the monocyclic heterocyclic group and a 3- to 7-membered carbocyclic group or through condensation of those, same or different monocyclic heterocyclic groups; and it includes the above-mentioned heteroaromatic groups. Its examples are, in addition to the those listed hereinabove for the above-mentioned heteroaromatic group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a dihydropyridyl group, a piperidyl group, a piperazinyl group, a morpholinyl group, and a thiomorpholinyl group.

"Hydroxy-lower alkoxy group" means the above-mentioned lower alkoxy group which is substituted by hydroxyl group(s) and which has one, two or more, but preferably one or two unlimited substitutable positions, and it includes, for example, a hydroxymethoxy group, a 2-hydroxyethoxy group, a 2-hydroxy-1-methylethoxy group, a 2-hydroxy-1-ethylethoxy group, a 1,2-dihydroxyethoxy group, a 3-hydroxypropoxy group.

"Lower alkoxy-lower alkoxy group" means the above-mentioned lower alkoxy group which is substituted by the above-mentioned lower alkoxy group(s) and which has one, two or more, but preferably one or two unlimited substitutable positions, and it includes, for example, a methoxymethoxy group, a 2-methoxyethoxy group, a 2-methoxy-1-methylethoxy group, a 1,2-dimethoxyethoxy group, a 3-methoxypropoxy group.

"Cyclo-lower alkyl group" means a cycloalkyl group having from 3 to 6 carbon atoms, and it includes a cyclopropyl group, a cyclobutyl group, a cyclopentyl group, and a cyclohexyl group.

"Cyclo-lower alkyloxy group" means a cycloalkyloxy group having the above-mentioned cyclo-lower alkyl group, and it includes a cyclopropyloxy group, a cyclobutyloxy group, a cyclopentyloxy group, and a cyclohexyloxy group.

"Cyclo-lower alkyl-lower alkoxy group" means the above-mentioned lower alkoxy group which is substituted by the above-mentioned cyclo-lower alkyl group and which has one, two or more, but preferably one unlimited substitutable position, and it includes, for example, a cyclopropylmethoxy group, a cyclobutylmethoxy group, a cyclopentylmethoxy group, a cyclopropylethoxy group, a cyclobutylethoxy group, and a cyclopropylpropoxy group.

"Lower alkylene group" means a linear or branched alkylene group having from 1 to 6 carbon atoms, and it includes, for example, a methylene group, an ethylene group, a trimethylene group, a tetramethylene group, a pentamethylene group, and a hexamethylene group.

"Lower alkylene group optionally interrupted by an oxygen atom, a sulfur atom or an imino group" means an alkylene group having from 2 to 5 carbon atoms, which is interrupted or not by one, two or more, but preferably one oxygen atom, sulfur atom or imino group at any position of the allylene chain thereof capable of being interrupted by it, and this includes, for example, an ethylene group, a trimethylene group, a tetramethylene group, a pentamethylene group, a 2-oxatetramethylene group, a 2-oxapentamethylene group, 3-oxapentamethylene group, a 2-thiatetramethylene group, a 2-thiapentamethylene group, a 3-thiapentamethylene group, a 2-azatetramethylene group, 2-azapentamethylene group, and a 3-azapentamethylene group.

"Salts" of the compound of formula (I) means pharmaceutically acceptable and common salts, including, for example, base addition salts of the compound having a carboxyl group, a hydroxyl group or an acidic heterocyclic group such as a tetrazolyl group, with a base added to the carboxyl group, the hydroxyl group or the acidic heterocyclic group of the compound; and acid addition salts of the compound having an amino group or a basic heterocyclic group, with an acid added to the amino group or the basic heterocyclic group of the compound.

The base addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

"Esters" of the compound of formula (I) means those of the compound having a carboxyl group, which are esterified at the carboxyl group of the compound and which are pharmaceutically acceptable esters, including, for example, esters with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or cyclopentyl group; esters with an aralkyl group such as a benzyl group or a phenethyl group; esters with a lower alkenyl group such as an allyl group or a 2-butenyl group; esters with a lower alkoxy-lower alkyl group such as a methoxymethyl group, a 2-methoxyethyl group or a 2-ethoxyethyl group; esters with a lower alkanoyloxy-lower alkyl group such as an acetoxymethyl group, a pivaloyloxymethyl group or a 1-pivaloyloxyethyl group; esters with a lower alkoxycarbonyl-lower alkyl group such as a methoxycarbonylmethyl group or an isopropoxycarbonylmethyl group; esters with a carboxy-lower alkyl group such as a carboxymethyl group; esters with a lower alkoxycarbonyloxy-lower alkyl group such as a 1-(ethoxycarbonyloxy)ethyl group or a 1-(cyclohexyloxycarbonyloxy)ethyl group; esters with a carbamoyloxy-lower alkyl group such as a carbamoyloxymethyl group; esters with a phthalidyl group; and esters with a (5-substituted-2-oxo-1,3-dioxol-4-yl)methyl group such as a (5-methyl-2-oxo-1,3-dioxol-4-yl)methyl group.

"Therapeutic agent" means a medicine used for the treatment and/or prevention of various disorders.

For more concrete disclosure of the compounds of formula (I) of the invention, the symbols used in formula (I) are described in detail hereinunder with reference to their embodiments.

In one embodiment, $R^1$ and $R^5$ each independently represent a hydrogen atom, a halogen atom, a cyano group, a lower alkenyl group, a lower alkoxy group, a lower alkanoyl group, a lower alkoxycarbonyl group, an aralkyloxycarbonyl group, a carbamoyl-lower alkoxy group, a carboxy-lower alkenyl group, or a group of $-Q^1-N(R^a)-Q^2-R^b$, a lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of $-CO-N(R^c)R^d$, or a lower alkyl or alkenyl group having the said aryl or heterocyclic group.

In one class, the halogen atom for $R^1$ and $R^5$ is, for example, a chlorine atom or a bromine atom.

In one class, the lower alkenyl group for $R^1$ and $R^5$ is, for example, a 2-propenyl group or an isopropenyl group.

In one class, the lower alkoxy group for $R^1$ and $R^5$ is, for example, a methoxy group or an ethoxy group.

In one class, the lower alkanoyl group for $R^1$ and $R^5$ is, for example, an acetyl group or a propionyl group.

In one class, the lower alkoxycarbonyl group for $R^1$ and $R^5$ is, for example, a methoxycarbonyl group or an ethoxycarbonyl group.

In one class, the aralkyloxycarbonyl group for $R^1$ and $R^5$ is, for example, a benzyloxycarbonyl group.

In one class, the carbamoyl-lower alkoxy group for $R^1$ and $R^5$ is, for example, a carbamoylmethoxy group or a 2-carbamoylethoxy group.

In one class, the carboxy-lower alkenyl group for $R^1$ and $R^5$ is, for example, a 2-carboxyvinyl group, a 3-carboxy-1-propenyl group or a 3-carboxy-2-propenyl group.

In the group of $-Q^1-N(R^a)-Q^2-R^b$ for $R^1$ and $R^5$, $Q^1$ and $Q^2$ each independently represent a single bond, or a group of $-CO-$, $-SO_2-$ or $-C(R^g)(R^h)-$, when $Q^2$ represents the group of $-C(R^g)(R^h)-$, $R^a$ and $R^g$, taken together, may represent a group of $-Q^1-N=C(R^h)-R^b$; $R^a$ and $R^b$ each independently represent a hydrogen atom, a lower alkenyl group, a lower alkoxy group, a halo-lower alkoxy group, an aralkyloxy group, a carbamoyl group, a lower alkoxycarbonyl group or a group of $-N(R^i)R^j$,
a lower alkyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group.

In $-C(R^g)(R^h)-$ for $Q^1$ and $Q^2$, $R^g$ and $R^h$ each independently represent a hydrogen atom, a lower alkyl group, or a halo-lower alkyl group.

In one class, $R^g$ and $R^h$ each are a hydrogen atom, a methyl group or an ethyl group.

In one class, $Q^1$ is a single bond, $-CO-$, $-SO_2-$ or $-C(CH_3)_2-$, and $Q^2$ is a single bond, $-CO-$ or $-CH_2-$.

When $Q^2$ represents the group of $-C(R^g)(R^h)-$, $R^a$ and $R^g$, taken together, may represent a group of $-Q^1-N=C(R^h)-R^b$ which includes, for example, a (1-propoxyethylidene)aminosulfonyl group.

The lower alkenyl group for $R^a$ and $R^b$ is, for example, a vinyl group or a 2-propenyl group.

The lower alkoxy group for $R^a$ and $R^b$ is, for example, a methoxy group or an ethoxy group.

The halo-lower alkoxy group for $R^a$ and $R^b$ is, for example, a fluoromethoxy group, a difluoromethoxy group, a trifluoromethoxy group, a chloromethoxy group, or a dichloromethoxy group.

The aralkyloxy group for $R^a$ and $R^b$ is, for example, a benzyloxy group.

The lower alkoxycarbonyl group for $R^a$ and $R^b$ is, for example, a methoxycarbonyl group, an ethoxycarbonyl group, or a tert-butoxycarbonyl group.

In the group of $-N(R^i)R^j$ for $R^a$ and $R^b$, $R^i$ and $R^j$ each independently represents a hydrogen atom, a lower alkyl group or a halo-lower alkyl group.

For example, in one class, $R^i$ and $R^j$ each are a hydrogen atom, a methyl group or a 2,2,2-trifluoroethyl group.

In another class, the group of $-N(R^i)R^j$ for $R^a$ and $R^b$ is an amino group, a dimethylamino group, or a 2,2,2-trifluoroethylamino group.

"Lower alkyl group optionally substituted by a substituent selected from a group consisting of a halogen atom, a lower alkoxy group, a carbamoyl group and a lower alkoxycarbonyl group" for $R^a$ and $R^b$ means the above-mentioned unsubstituted lower alkyl group, or the above-mentioned lower alkyl group having a substituent at any substitutable position thereof, in which the substituent may be one, two or more and the same or different, but preferably from 1 to 3 substituents selected from a group consisting of a halogen atom, a lower alkoxy group, a carbamoyl group and a lower alkoxycarbonyl group.

In one class, the halogen atom for the substituent is a fluorine atom or a chlorine atom.

In another class, the lower alkoxy group for the substituent is a methoxy group or an ethoxy group.

In yet another class, the lower alkoxycarbonyl group for the substituent is a methoxycarbonyl group, an ethoxycarbonyl group, or a tert-butoxycarbonyl group.

In still another class, the substituent is a halogen atom, a carbamoyl group, or a lower alkoxycarbonyl group.

"Lower alkyl group" per se of the lower alkyl group that may optionally have a substituent for $R^a$ and $R^b$ is, for example, a methyl group, an ethyl group, a propyl group or an isopropyl group.

The lower alkyl group that may optionally have a substituent for $R^a$ and $R^b$ is, for example, a methyl group, a difluoromethyl group, a trifluoromethyl group, a methoxymethyl group, a carbamoylmethyl group, a tert-butoxycarbonylmethyl group, an ethyl group, a propyl group, or an isopropyl group.

"Heteroaromatic group optionally substituted by a lower alkyl group that is optionally substituted by a substituent selected from a group consisting of a halogen atom, a lower alkoxy group, a carbamoyl group and a lower alkoxycarbonyl group" for $R^a$ and $R^b$ means the above-mentioned unsubstituted heteroaromatic group, or the above-mentioned heteroaromatic group having, as the substituent thereof, "a lower alkyl group that is optionally substituted by a substituent selected from a group consisting of a halogen atom, a lower alkoxy group, a carbamoyl group and a lower alkoxycarbonyl group" at any substitutable position thereof, in which the substituent on the heteroaromatic group may be one, two or more and the same or different, but preferably one or two substituents selected from the above.

Examples of the "lower alkyl group that is optionally substituted by a substituent selected from a group consisting of a halogen atom, a lower alkoxy group, a carbamoyl group and a lower alkoxycarbonyl group", as the substituent on the heteroaromatic group, may be the same as those listed hereinabove for the "lower alkyl group optionally having a substituent" for the above-mentioned $R^a$ and $R^b$.

"Heteroaromatic group" per se of the heteroaromatic group optionally substituted by a lower alkyl group that may have the above-mentioned substituent for $R^a$ and $R^b$ is, for example, a pyrrolyl group, a pyrazolyl group, a 1,2,4-triazolyl group or a pyrimidinyl group; in one class, the "heteroaromatic group" per se is a pyrazolyl group or a 1,2,4-triazolyl group.

The heteroaromatic group optionally substituted by a lower alkyl group that may have the above-mentioned substituent for $R^a$ and $R^b$ is, for example, a 2-pyrrolyl group, a 1-methyl-2-pyrrolyl group, a 3-pyrazolyl group, a 2-methyl-3-pyrazolyl group, a 2-ethyl-3-pyrazolyl group, a 2-methoxymethyl-3-pyrazolyl group, a 1,2,4-triazol-3-yl group, a 1-methyl-1,2,4-triazol-3-yl group, a 2-methyl-1,2,4-triazol-3-yl group, a 2-pyrimidinyl group or a 5-pyrimidinyl group, or in one class the heteroaromatic group is a 2-methyl-3-pyrazolyl group, a 2-ethyl-3-pyrazolyl group or a 1,2,4-triazol-3-yl group.

In one class, $R^a$ and $R^b$ each are a hydrogen atom, a lower alkoxy group, an aralkyloxy group, a carbamoyl group, a lower alkoxycarbonyl group, a group of —N($R^i$)$R^j$, a lower alkyl group optionally having the above-mentioned substituent, or a heteroaromatic group optionally substituted by a lower alkyl group that may have the above-mentioned substituent; in a subclass of this class $R^a$ and $R^b$ each are a hydrogen atom, a lower alkoxy group, a carbamoyl group, a group of —N($R^i$)$R^j$, a lower alkyl group optionally having the above-mentioned substituent, or a heteroaromatic group optionally substituted by a lower alkyl group that may have the above-mentioned substituent.

In another embodiment, $R^1$ or $R^{1a}$ is an acetylamino group, a methoxycarbonylamino group, a carbamoylamino group, a 2-methyl-3-pyrazolylamino group, a 2-ethyl-3-pyrazolylamino group, a 1,2,4-triazol-3-ylamino group, a (carbamoylmethyl)carbamoyl group, an aminosulfonyl group, a methylaminosulfonyl group, a 1-carboxy-1-methylethyl group, a tert-butyl group, a 3-carboxyphenyl group, a 4-pyrazolyl group, a 1-methyl-4-pyrazolyl group, a 1,2,4-triazol-3-yl group, a 5-carbamoyl-1,2,4-triazol-3-yl group, a 5-tetrazolyl group, a 1-methyl-5-tetrazolyl group, a 2-methyl-5-tetrazolyl group, a 1-pivaloyloxymethyl-5-tetrazolyl group, a 2-pivaloyloxymethyl-5-tetrazolyl group, a 3-pyridyl group, a 4-carboxy-2-pyridyl group, a 5-carboxy-3-pyridyl group, a 5-carbamoyl-2-pyridyl group, a 5-carbamoyl-3-pyridyl group, a 2-pyrimidinyl group, a 5-oxo-4,5-dihydro-1,2,4-triazol-3-yl group, a 5-oxo-4,5-dihydro-1,2,4-oxadiazol-3-yl group, a 5-oxo-4,5-dihydro-1,3,4-oxadiazol-2-yl group, a 3-oxo-1-piperazinyl group, a 4-acetyl-1-piperazinyl group, a 4-carbamoyl-1-piperazinyl group, a 4-methylsulfonyl-1-piperazinyl group or a 1,1-dioxido-4-thiomorpholinyl group, and $R^5$ is a hydrogen atom.

In another embodiment, $R^1$ or $R^{1a}$ is an acetylamino group, a carbamoylamino group, a 2-methyl-3-pyrazolylamino group, a 1-carboxy-1-methylethyl group, a tert-butyl group, a 5-tetrazolyl group, a 2-pivaloyloxymethyl-5-tetrazolyl group, a 4-carboxy-2-pyridyl group, a 5-carboxy-3-pyridyl group, a 5-carbamoyl-3-pyridyl group, or a 3-oxo-1-piperazinyl group, and $R^5$ is a hydrogen atom.

Another embodiment of the group of -$Q^1$-N($R^a$)-$Q^2$-$R^b$ for $R^1$ and $R^5$ includes, for example, the case where (i) $Q^1$ and $Q^2$ are a single bond, $R^a$ is a hydrogen atom or a lower alkyl group, and $R^b$ is a heteroaromatic group optionally substituted by a lower alkyl group that is optionally substituted by a substituent selected from a group consisting of a halogen atom, a lower alkoxy group, a carbamoyl group and a lower alkoxycarbonyl group, (ii) $Q^1$ is a single bond, $Q^2$ is a group of —CO—, $R^a$ is a hydrogen atom or a lower alkyl group, and $R^b$ is a hydrogen atom, a lower alkoxy group, a halo-lower alkoxy group, an aralkyloxy group or a group of —N($R^i$)$R^j$, or a lower alkyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group, (iii) $Q^1$ is a group of —CO—, $Q^2$ is a single bond, and $R^a$ and $R^b$ each independently are a hydrogen atom or a lower alkyl group, (iv) $Q^1$ is a group of —CO—, $Q^2$ is a group of —C($R^g$)($R^h$)—, $R^a$ is a hydrogen atom or a lower alkyl group, and $R^b$ is a carbamoyl group, or a lower alkyl group optionally substituted by a substituent selected from a group consisting of a halogen atom, a lower alkoxy group, a carbamoyl group and a lower alkoxycarbonyl group, or (v) $Q^1$ is a group of —SO$_2$—, $Q^2$ is a single bond, and $R^a$ and $R^b$ each independently are a hydrogen atom or a lower alkyl group.

In one class, the group of -$Q^1$-N($R^a$)-$Q^2$-$R^b$ for $R^1$ and $R^5$ includes, for example, an isopropylamino group, a formylamino group, an acetylamino group, a methoxycarbonylamino group, a benzyloxycarbonylamino group, a carbamoylamino group, a 2,2,2-trifluoroethylcarbamoylamino group, a 2-pyrrolylcarbonylamino group, a 1-methyl-2-pyrrolylcarbonylamino group, a 3-pyrazolylamino group, a 2-methyl-3-pyrazolylamino group, a 2-ethyl-3-pyrazolylamino group, a 2-methoxymethyl-3-pyrazolylamino group, an N-methyl-N-(2-methyl-3-pyrazolyl)amino group, a 1,2,4-triazol-3-ylamino group, a 1-methyl-1,2,4-triazol-3-ylamino group, a 2-methyl-1,2,4-triazol-3-ylamino group, a 2-pyrimidinylamino group, a 5-pyrimidinylamino group, a carbamoyl group, a methylcarbamoyl group, a 2,2-difluoroethylcarbamoyl group, a (carbamoylmethyl)carbamoyl group, a (2-carbamoylethyl)carbamoyl group, a (1-carbamoyl-1-methylethyl)carbamoyl group, a (1-tert-butoxycarbonyl-1-methylethyl)carbamoyl group, a (2-tert-butoxycarbonylethyl) carbamoyl group, an aminosulfonyl group, a methylaminosulfonyl group, a dimethylaminosulfonyl group, an ethylaminosulfonyl group, a propylaminosulfonyl group, a butylaminosulfonyl group, an N-acetyl-N-methylaminosulfonyl group, an N-acetyl-N-ethylaminosulfonyl group, an N-acetyl-N-propylaminosulfonyl group, a 1-amino-1-methylethyl group, a 1-acetylamino-1-methylethyl group, a 1-(benzyloxycarbonylamino)-1-methylethyl group; in another class the group of -$Q^1$-N($R^a$)-$Q^2$-$R^b$ for $R^1$ and $R^5$ is an acetylamino group, a methoxycarbonylamino group, a carbamoylamino group, a 2-methyl-3-pyrazolylamino group, a 2-ethyl-3-pyrazolylamino group, a 1,2,4-triazol-3-ylamino group, a (carbamoylmethyl)carbamoyl group, an aminosulfonyl group or a methylaminosulfonyl group.

"Lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group" for $R^1$ and $R^5$ means the above-mentioned unsubstituted lower allyl group, or the above-mentioned lower alkyl group having a substituent at any substitutable position thereof, in which the substituent may be one, two or more and the same or different, but preferably from 1 to 3 substituents selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group.

In one class, the halogen atom for the substituent is a fluorine atom or a chlorine atom.

In one class, the lower alkoxy group for the substituent is a methoxy group or an ethoxy group.

In one class, the halo-lower alkoxy group for the substituent is a difluoromethoxy group.

In one class, the lower alkylthio group for the substituent is a methylthio group or an ethylthio group.

In one class, the lower alkanoyloxy group for the substituent is an acetyloxy group or a propionyloxy group.

In one class, the lower alkoxycarbonyl group for the substituent is a methoxycarbonyl group or an ethoxycarbonyl group.

In one class, the lower alkylsulfonyl group for the substituent is a methylsulfonyl group or an ethylsulfonyl group.

In one class, the substituent is a halogen atom, a hydroxyl group, a carboxyl group, a carbamoyl group or a lower alkoxycarbonyl group; in another class the substituent is a carboxyl group.

"Lower alkyl group" per se of the lower alkyl group that may optionally have a substituent for $R^1$ and $R^5$ is, for example, a methyl group, an ethyl group, a propyl group, an isopropyl group or a tert-butyl group; or in one class "lower alkyl group" per se is a tert-butyl group.

In one class, the lower alkyl group that may optionally have a substituent for $R^1$ is a methyl group, a fluoromethyl group, a hydroxymethyl group, an azidomethyl group, a methoxymethyl group, a methylthiomethyl group, an acetyloxymethyl group, a methoxycarbonylmethyl group, a methylsulfonylmethyl group, an ethyl group, a 1-hydroxyethyl group, a 1-carboxy-1-methylethyl group, a 1-carbamoyl-1-methylethyl group, a 1-methoxycarbonyl-1-methylethyl group, a propyl group, an isopropyl group, or a tert-butyl group; in another class, the lower alkyl group is a 1-carboxy-1-methylethyl group or a tert-butyl group.

"Aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$" for $R^1$ and $R^5$ means the above-mentioned unsubstituted aryl or heterocyclic group, or the above-mentioned aryl or heterocyclic group having a substituent at any substitutable position thereof, in which the substituent may be one, two or more and the same or different, but preferably one or two substituents selected from a group consisting of a halogen atom, a hydroxyl group, an oxo group, a thioxo group, a lower alkyl group, a halo-lower alkyl group, a hydroxy-lower allyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$.

In one class, the halogen atom for the substituent is a fluorine atom or a chlorine atom.

In one class, the lower alkyl group for the substituent is a methyl group or an ethyl group.

In one class, the halo-lower alkyl group for the substituent is a fluoromethyl group, a difluoromethyl group or a trifluoromethyl group.

In one class, the hydroxy-lower alkyl group for the substituent is a hydroxymethyl group, a 1-hydroxyethyl group or a 2-hydroxyethyl group.

In one class, the lower alkanoyloxy-lower alkyl group for the substituent is an acetyloxymethyl group or a pivaloyloxymethyl group.

In one class, the lower alkoxy group for the substituent is a methoxy group or an ethoxy group.

In one class, the halo-lower alkoxy group for the substituent is a difluoromethoxy group.

In one class, the lower alkanoyl group for the substituent is an acetyl group or a propionyl group.

In one class, the lower alkoxycarbonyl group for the substituent is a methoxycarbonyl group or an ethoxycarbonyl group.

In one class, the lower alkylsulfonyl group for the substituent is a methylsulfonyl group.

In the group —CO—N($R^c$)$R^d$ for the substituent, $R^c$ and $R^d$ each independently represent a hydrogen atom, a lower alkyl group, or a halo-lower alkyl group.

In one class, the lower alkyl group for $R^c$ and $R^d$ is a methyl group or an ethyl group.

In another class, the group —CO—N($R^c$)$R^d$ for the substituent is a carbamoyl group or a dimethylcarbamoyl group.

In another class, the substituent is an oxo group, a lower alkyl group, a carboxyl group, a lower alkylsulfonyl group, or a group of —CO—N($R^c$)$R^d$.

"Aryl group" per se of the aryl or heterocyclic group optionally having a substituent for $R^1$ and $R^5$ is, for example, a phenyl group; and "heterocyclic group" per se thereof is, for example, a pyrrolyl group, an imidazolyl group, a pyrazolyl group, a 1,2,4-triazolyl group, a tetrazolyl group, a pyridyl group, a pyrimidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidyl group, a piperazinyl group, a morpholinyl group or a thiomorpholinyl group; in one class the "aryl" group per se is a pyrazolyl group, a 1,2,4-triazolyl group, a tetrazolyl group, a pyridyl group, a pyrimidinyl group, a dihydro-1,2,4-triazolyl group, a dihydro-1,2,4-oxadiazolyl group, a dihydro-1,3,4-oxadiazolyl group, a piperazinyl group or a thiomorpholinyl group; in another class, the "aryl" group per se is a tetrazolyl group or a pyridyl group.

The aryl or heterocyclic group optionally having a substituent for $R^1$ and $R^5$ is, for example, a phenyl group optionally substituted by a carboxyl group; a pyrazolyl group optionally substituted by a lower alkyl group; a 1,2,4-triazolyl group optionally substituted by a group of —CO—N($R^c$)$R^d$; a tetrazolyl group optionally substituted by a lower alkyl group or a lower alkanoyloxy-lower allyl group; a pyridyl group optionally substituted by a carboxyl group or a group of —CO—N($R^c$)$R^d$; a pyrimidinyl group; a dihydro-1,2,4-triazolyl group optionally substituted by an oxo group; a dihydro-1,2,4-oxadiazolyl group optionally substituted by an oxo group; a dihydro-1,3,4-oxadiazolyl group optionally substituted by an oxo group; a piperazinyl group optionally substituted by an oxo group, a lower alkanoyl group, a lower alkylsulfonyl group or a group of —CO—N($R^c$)$R^d$; a thiomorpholinyl group optionally substituted by an oxo group; in one class the aryl or heterocyclic group is a tetrazolyl group optionally substituted by a lower alkyl group or a lower alkanoyloxy-lower alkyl group; or a pyridyl group optionally substituted by a carboxyl group or a group of —CO—N($R^c$)$R^d$.

The aryl or heterocyclic group optionally having a substituent for $R^1$ and $R^5$ includes, for example, a phenyl group, a 3-carboxyphenyl group, a 4-carbamoylphenyl group, a 1-pyrrolyl group, a 1-imidazolyl group, a 3-pyrazolyl group, a 4-pyrazolyl group, a 1-methyl-4-pyrazolyl group, a 1,2,4-triazol-3-yl group, a 1,2,4-triazol-4-yl group, a 5-carbamoyl-1,2,4-triazol-3-yl group, a 1-tetrazolyl group, a 5-tetrazolyl group, a 1-methyl-5-tetrazolyl group, a 2-methyl-5-tetrazolyl group, a 1-pivaloyloxymethyl-5-tetrazolyl group, a 2-pivaloyloxymethyl-5-tetrazolyl group, a 2-dimethylcarbamoyl-5-tetrazolyl group, a 3-pyridyl group, a 4-carboxy-2-pyridyl group, a 5-carboxy-3-pyridyl group, a 5-carbamoyl-2-pyridyl group, a 5-carbamoyl-3-pyridyl group, a 2-pyrimidinyl group, a 5-pyrimidinyl group, a 2-oxo-1-pyrrolidinyl group, a 5-oxo-4,5-dihydro-1,2,4-triazol-3-yl group, a 3-oxo-2,3-dihydro-1,2,4-triazol-4-yl group, a 5-oxo-4,5-dihydro-1,2,4-oxadiazol-3-yl group, a 5-thioxo-4,5-dihydro-1,2,4-oxadiazol-3-yl group, a 5-oxo-4,5-dihydro-1,3,4-oxadiazol-2-yl group, a 5-oxo-4,5-dihydro-1,2,4-thiadiazol-3-yl group, a 2-oxo-2,3-dihydro-1,2,3,5-oxathiadiazol-4-yl group, a 1-piperidyl group, a 4-oxo-1-piperidyl group, a 1-piperazinyl group, a 3-oxo-1-piperazinyl group, a 4-methyl-1-piperazinyl group, a 4-formyl-1-piperazinyl group, a 4-acetyl-1-piperazinyl group, a 4-methoxycarbonyl-1-piperazinyl group, a 4-carbamoyl-1-piperazinyl group, a 4-methylsulfonyl-1-piperazinyl group, a 4-morpholinyl group, or a 1,1-dioxido-4-thiomorpholinyl group. In one class the aryl and heterocyclic group is a 3-carboxyphenyl group, a 4-pyrazolyl group, a 1-methyl-4-pyrazolyl group, a 1,2,4-triazol-3-yl group, a 5-carbamoyl-1,2,4-triazol-3-yl group, a 5-tetrazolyl group, a 1-methyl-5-tetrazolyl group, a 2-methyl-5-tetrazolyl group, a 1-pivaloyloxymethyl-5-tetrazolyl group, a 2-pivaloyloxymethyl-5-tetrazolyl group, a 3-pyridyl group, a 4-carboxy-2-pyridyl group, a 5-carboxy-3-pyridyl group, a 5-carbamoyl-2-pyridyl group, a 5-carbamoyl-3-pyridyl group, a 2-pyrimidinyl group, a 5-oxo-4,5-dihydro-1,2,4-triazol-3-yl group, a 5-oxo-4,5-dihydro-1,2,4-oxadiazol-3-yl group, a 5-oxo-4,5-dihydro-1,3,4-oxadiazol-2-yl group, a 3-oxo-1-piperazinyl group, a 4-acetyl-1-piperazinyl group, a 4-carbamoyl-1-piperazinyl group, a 4-methylsulfonyl-1-piperazinyl group or a 1,1-dioxido-4-thiomorpholinyl group; in another class the aryl and heterocyclic group is a 5-tetrazolyl group or a 5-carboxy-3-pyridyl group; in yet another class the aryl and heterocyclic group is a 5-tetrazolyl group.

"Lower alkyl or alkenyl group having the said aryl or heterocyclic group" for $R^1$ and $R^5$ means the above-mentioned lower alkyl or alkenyl group having one, two or more and the same or different, but preferably one aryl or heterocyclic group selected from the above-mentioned "aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$" and includes, for example, a 5-tetrazolylmethyl group, a 2-(5-tetrazolyl)ethyl group, a 2-(5-tetrazolyl)vinyl group, a 3-(5-tetrazolyl)-1-propenyl group.

In another embodiment of $R^1$ and $R^5$ include, for example, the case where $R^1$ is a hydrogen atom, a halogen atom, a cyano group, an aralkyloxycarbonyl group or a group of -$Q^1$-N($R^a$)-$Q^2$-$R^b$, a lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$, or a lower alkyl or alkenyl group having the said aryl or heterocyclic group, and in the group of -$Q^1$-N($R^a$)-$Q^2$-$R^b$,
(i) $Q^1$ and $Q^2$ are a single bond, $R^a$ is a hydrogen atom or a lower alkyl group, and $R^b$ is a heteroaromatic group optionally substituted by a lower alkyl group that is optionally substituted by a substituent selected from a group consisting of a halogen atom, a lower alkoxy group, a carbamoyl group and a lower alkoxycarbonyl group,
(ii) $Q^1$ is a single bond, $Q^2$ is a group of —CO—, $R^a$ is a hydrogen atom or a lower alkyl group, and $R^b$ is a hydrogen atom, a lower alkoxy group, a halo-lower alkoxy group, an aralkyloxy group or a group of —N($R^i$)$R^j$, or a lower alkyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group,
(iii) $Q^1$ is a group of —CO—, $Q^2$ is a single bond, and $R^a$ and $R^b$ each independently are a hydrogen atom or a lower alkyl group,
(iv) $Q^1$ is a group of —CO—, $Q^2$ is a group of —C($R^g$)($R^h$)—, $R^a$ is a hydrogen atom or a lower alkyl group, and $R^b$ is a carbamoyl group, or a lower alkyl group optionally substituted by a substituent selected from a group consisting of a halogen atom, a lower alkoxy group, a carbamoyl group and a lower alkoxycarbonyl group, or
(v) $Q^1$ is a group of —$SO_2$—, $Q^2$ is a single bond, and $R^a$ and $R^b$ each independently are a hydrogen atom or a lower alkyl group; and
$R^5$ is a hydrogen atom.

In one class, $R^1$ is a group of -$Q^1$-N($R^a$)-$Q^2$-$R^b$, or a lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, or an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$.

In one embodiment, $R^2$, $R^3$ and $R^4$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a hydroxy-lower alkoxy group, a lower alkoxy-lower alkoxy group, a cyclo-lower alkyloxy group, a cyclo-lower alkyl-lower alkoxy group, a lower alkylthio group, a group of —O—$R^k$ or a group of —N($R^e$)$R^f$, or a lower alkoxy group substituted by the group of —N($R^e$)$R^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower alkyl group, a lower alkenyl group, a lower alkoxy group, a halo-lower alkoxy group and a lower alkylthio group, provided that at least one of $R^2$, $R^3$ and $R^4$ is lower alkoxy, hydroxy-lower alkoxy, cyclo-lower alkyl, or aryl substituted with at least one lower alkoxy.

In another embodiment, $R^2$, $R^3$ and $R^4$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a hydroxy-lower alkoxy group, a lower alkoxy-lower alkoxy group, a cyclo-lower alkyloxy group, a cyclo-lower alkyl-lower alkoxy group, a lower alkylthio group, a group of O—$R^k$ or a group of —N($R^e$)$R^f$ or a lower alkoxy group substituted by the group of —N($R^e$)$R^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower alkyl group, a hydroxy-lower allyl group, a cyclo-lower alkyl group, a lower alkenyl group, a lower alkoxy group, a halo-lower alkoxy group and a lower alkylthio group.

In one class, the halogen atom for $R^2$, $R^3$ and $R^4$ is, for example, a fluorine atom, a chlorine atom or a bromine atom.

In one class, The cyclo-lower alkyl group for $R^2$, $R^3$ and $R^4$ is, for example, a cyclopropyl group.

In one class, The lower alkenyl group for $R^2$, $R^3$ and $R^4$ is, for example, a 2-propenyl group or an isopropenyl group.

In one class, The lower alkoxy group for $R^2$, $R^3$ and $R^4$ is, for example, a methoxy group, an ethoxy group, a propoxy group or an isopropoxy group.

In one class, The halo-lower alkoxy group for $R^2$, $R^3$ and $R^4$ is, for example, a fluoromethoxy group, a difluoromethoxy group or a trifluoromethoxy group.

In one class, The hydroxy-lower alkoxy group for $R^2$, $R^3$ and $R^4$ is, for example, a 2-hydroxyethoxy group, a 2-hydroxy-1-methylethoxy group or a 2-hydroxy-1-ethylethoxy group.

In one class, The lower alkoxy-lower alkoxy group for $R^2$, $R^3$ and $R^4$ is, for example, a 2-methoxy-1-methylethoxy group.

In one class, The cyclo-lower alkyloxy group for $R^2$, $R^3$ and $R^4$ is, for example, a cyclopropyloxy group.

In one class, The cyclo-lower alkyl-lower alkoxy group for $R^2$, $R^3$ and $R^4$ is, for example, a cyclopropylmethoxy group.

In one class, The lower alkylthio group for $R^2$, $R^3$ and $R^4$ is, for example, a methylthio group, an ethylthio group, a propylthio group or an isopropylthio group.

In one class, In the group of —O—$R^k$ for $R^2$, $R^3$ and $R^4$, $R^k$ represents a pyrrolidinyl, tetrahydrofuranyl, piperidyl group optionally substituted by a lower alkyl group or a halo-lower alkyl group.

In one class, the lower alkyl group for the substituent is a methyl group or an ethyl group.

In one class, the halo-lower alkyl group for the substituent is a chloromethyl group, a fluoromethyl group or a difluoromethyl group.

In another class the group of —O—$R^k$ is a 3-pyrrolidinyloxy group, a 1-methyl-3-pyrrolidinyloxy group, a 3-tetrahydrofuranyloxy group or a 1-methyl-4-piperidyloxy group; in yet another class the group of —O—$R^k$ is a 1-methyl-3-pyrrolidinyloxy group or a 3-tetrahydrofuranyloxy group.

In the group of —N($R^e$)$R^f$ for $R^2$, $R^3$ and $R^4$, $R^e$ and $R^f$ each independently represent a hydrogen atom, a lower alkyl group or a halo-lower alkyl group, or taken together, they may form a lower alkylene group optionally interrupted by an oxygen atom, a sulfur atom or an imino group.

In one class, the lower alkyl group for $R^e$ and $R^f$ is a methyl group, an ethyl group or a propyl group.

In one class, the halo-lower alkyl group for $R^e$ and $R^f$ is a fluoromethyl group, a difluoromethyl group or a trifluoromethyl group.

"Lower alkylene group optionally interrupted by an oxygen atom, a sulfur atom or an imino group" that may be formed by $R^e$ and $R^f$ taken together is, for example, a tetramethylene group, a pentamethylene group or a 3-oxapentamethylene group, and it may form a 1-pyrrolidinyl group, piperidino group or a morpholino group along with the adjacent nitrogen atom.

In one embodiment of $R^e$ and $R^f$ taken together, $R^e$ and $R^f$ form a lower alkylene group optionally interrupted by an oxygen atom, a sulfur atom or an imino group.

Accordingly, for example, the group of —N($R^e$)$R^f$ is an amino group, a methylamino group, an ethylamino group, a propylamino group, a dimethylamino group, a diethylamino group, an ethylmethylamino group, a 1-azetidinyl group, a 1-pyrrolidinyl group, a piperidino group, a morpholino group, a thiomorpholino group, or a 1-piperazinyl group, or in one class the group of —N($R^e$)$R^f$ is a morpholino group.

"Lower alkoxy group substituted by the group of —N($R^e$)$R^f$" for $R^2$, $R^3$ and $R^4$ means the above-mentioned lower alkoxy group substituted by the above-mentioned group of —N($R^e$)$R^f$, and includes, for example, a 2-dimethylaminoethoxy group.

"Lower alkyl group optionally having a substituent selected from a group consisting of a halogen atom, a hydroxyl group and a cyclo-lower alkyl group" for $R^2$, $R^3$ and $R^4$ means the above-mentioned unsubstituted alkyl group, or the above-mentioned alkyl group having a substituent at any substitutable position thereof, in which the substituent may be one, two or more and the same or different, but preferably from 1 to 3 substituents selected from a group consisting of a halogen atom, a hydroxyl group and a cyclo-lower alkyl group.

In one class, the halogen atom for the substituent is a fluorine atom or a chlorine atom.

In one class, the cyclo-lower alkyl group for the substituent is a cyclopropyl group.

In another class, the substituent is a halogen atom or a cyclo-lower alkyl group.

"Lower alkyl group" per se of the lower alkyl group optionally having a substituent for $R^2$, $R^3$ and $R^4$ is, for example, a methyl group, an ethyl group or a propyl group.

In one class, the lower alkyl group optionally having a substituent for $R^2$, $R^3$ and $R^4$ is, for example, a methyl group, a fluoromethyl group, a hydroxymethyl group, a cyclopropylmethyl group, an ethyl group, a 1-hydroxyethyl group, a propyl group, an isopropyl group, or a tert-butyl group; in another class the lower alkyl group is an ethyl group.

"Aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower alkyl group, a lower alkenyl group, a lower alkoxy group, a halo-lower alkoxy group and a lower alkylthio group" for $R^2$, $R^3$ and $R^4$ means the above-mentioned unsubstituted aryl or heteroaromatic group, or the above-mentioned aryl or heteroaromatic group having a substituent at any substitutable position thereof, in which the substituent may be one, two or more and the same or different, but preferably one or two substituents selected from a group consisting of a halogen atom, a nitro group, a hydroxyl group, a lower allyl group, a halo-lower alkyl group, a hydroxy-lower alkyl group, a cyclo-lower alkyl group, a lower alkenyl group, a lower alkoxy group, a halo-lower alkoxy group and a lower alkylthio group.

In one class, the halogen atom for the substituent is, for example, a fluorine atom or a chlorine atom.

In one class, the lower alkyl group for the substituent is, for example, a methyl group or an ethyl group.

In one class, the halo-lower alkyl group for the substituent is, for example, a fluoromethyl group, a difluoromethyl group or a trifluoromethyl group.

In one class, the hydroxy-lower alkyl group for the substituent is, for example, a hydroxymethyl group, a 1-hydroxyethyl group or a 2-hydroxyethyl group.

In one class, the cyclo-lower alkyl group for the substituent is, for example, a cyclopropyl group.

In one class, the lower alkenyl group for the substituent is, for example, a 2-propenyl group or an isopropenyl group.

In one class, the lower alkoxy group for the substituent is, for example, a methoxy group or an ethoxy group.

In one class, the halo-lower alkoxy group for the substituent is, for example, a difluoromethoxy group.

In one class, the lower alkylthio group for the substituent is, for example, a methylthio group or an ethylthio group.

In one class, the substituent is a halogen atom or a lower alkyl group.

"Aryl group" per se of the aryl or heteroaromatic group optionally having a substituent for $R^2$, $R^3$ and $R^4$ is, for example, a phenyl group; and "heteroaromatic group" per se thereof is, for example, a 1,2,4-triazolyl group, a tetrazoly group or a pyridyl group.

In one class, the aryl or heteroaromatic group optionally having a substituent for $R^2$, $R^3$ and $R^4$ is a phenyl group, a 5-tetrazoly group, a 2-pyridyl group, a 3-pyridyl group or a 4-pyridyl group, in another class the aryl or heteroaromatic group is a phenyl group or a 5-tetrazoly group.

In another class, $R^2$, $R^3$ and $R^4$ each are a hydrogen atom, a fluorine atom, a chlorine atom, a bromine atom, a hydroxyl group, a nitro group, a cyano group, a cyclopropyl group, a methoxy group, an ethoxy group, a propoxy group, an isopropoxy group, a fluoromethoxy group, a difluoromethoxy group, a methylthio group, a 2-hydroxyethoxy group, a 2-hydroxy-1-methyethoxy group, a 2-hydroxy-1-ethylethoxy group, 2-methoxy-1-methyethoxy group, a cyclopropyloxy group, a 1-methyl-3-pyrrolidinyloxy group, a 3-tetrahydrofuranyloxy group, a dimethylamino group, a diethylamino group, a 1-pyrrolidinyl group, a piperidino group, a morpholino group, a methyl group, a fluoromethyl group, a hydroxymethyl group, a cyclopropylmethyl group, an ethyl group, a 1-hydroxyethyl group, a propyl group, an isopropyl group, a tert-butyl group, a phenyl group, a 2-fluorophenyl group, a 4-fluorophenyl group, a 3,4-dimethoxyphenyl group, a 4-difluoromethoxyphenyl group, a 1,2,4-triazol-3-yl group, a 5-tetrazolyl group or a 3-pyridyl group, in yet another class $R^2$, $R^3$ and $R^4$ are a hydrogen atom, a chlorine atom, a hydroxyl group, a cyclopropyl group, a methoxy group, an ethoxy group, a 2-hydroxyethoxy group, a morpholino group, an ethyl group, a phenyl group or a 5-tetrazolyl group.

T, U, W and Y each independently represent a nitrogen atom or a methine group. When T, U, W and Y each are a methine group, then the methine group may be substituted by any of $R^1$, $R^2$, $R^3$ or $R^4$. The methine group for W may be bound with the adjacent carbonyl group.

In one embodiment, T is a methine group; and W is a nitrogen atom.

In one embodiment, V represents an oxygen atom or a sulfur atom. In another embodiment, V is an oxygen atom.

In the compound of formula (I), $R^1$ and $R^5$ may be at any substitutable position of the skeleton of the following:

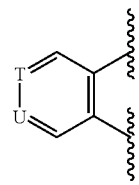

and $R^2$, $R^3$ and $R^4$ may be at any substitutable position of the skeleton of the following:

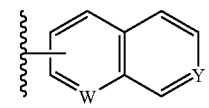

One embodiment of the compound of formula (I) is, for example, a compound of the following general formula (I-1):

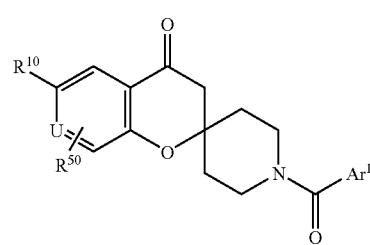

(I-1)

wherein $Ar^1$ is selected from a group of formula (aa):

(aa)

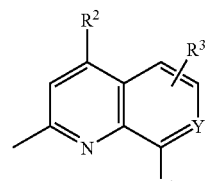

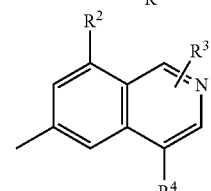

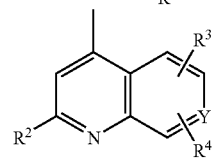

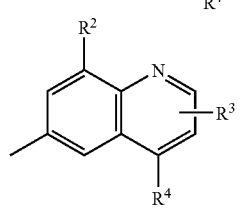

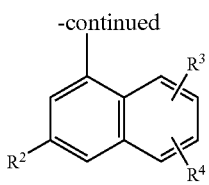

$R^{10}$ is a hydrogen atom, a halogen atom, a cyano group, an aralkyloxycarbonyl group or a group of $-Q^1-N(R^a)-Q^2-R^b$, a lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower allyl group, a lower alkoxy group, a halo-lower alkoxy group, a formyl group, a carboxyl group, a lower alkanoyl group, a lower alkoxycarbonyl group, a lower alkylsulfonyl group and a group of $—CO—N(R^c)R^d$, or a lower alkyl or alkenyl group having the said aryl or heterocyclic group, and in the group of $-Q^1-N(R^a)-Q^2-R^b$, (i) $Q^1$ and $Q^2$ are a single bond, $R^a$ is a hydrogen atom or a lower alkyl group, and $R^b$ is a heteroaromatic group optionally substituted by a lower alkyl group that is optionally substituted by a substituent selected from a group consisting of a halogen atom, a lower alkoxy group, a carbamoyl group and a lower alkoxycarbonyl group, (ii) $Q^1$ is a single bond, $Q^2$ is a group of $—CO—$, $R^a$ is a hydrogen atom or a lower alkyl group, and $R^b$ is a hydrogen atom, a lower alkoxy group, a halo-lower alkoxy group, an aralkyloxy group or a group of $—N(R^i)R^j$, or a lower alkyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group, (iii) $Q^1$ is a group of $—CO—$, $Q^2$ is a single bond, and $R^a$ and $R^b$ each independently are a hydrogen atom or a lower alkyl group, (iv) $Q^1$ is a group of $—CO—$, $Q^2$ is a group of $—C(R^g)(R^h)—$, $R^a$ is a hydrogen atom or a lower alkyl group, and $R^b$ is a carbamoyl group, or a lower alkyl group optionally substituted by a substituent selected from a group consisting of a halogen atom, a lower alkoxy group, a carbamoyl group and a lower alkoxycarbonyl group, or (v) $Q^1$ is a group of $—SO_2—$, $Q^2$ is a single bond, and $R^a$ and $R^b$ each independently are a hydrogen atom or a lower alkyl group;

$R^{50}$ is a hydrogen atom, a halogen atom or a lower alkyl group; and $R^2, R^3, R^4, R^c, R^d, R^g, R^h, R^i, R^j$, U and Y have the same meanings as above.

In formula (I-1), embodiments of $R^{10}, R^{50}, R^2, R^3, R^4$, U and Y may be the same as those of $R^1, R^5, R^2, R^3, R^4$, U and Y which respectively correspond to them in formula (I) mentioned hereinabove. In one class, $R^{10}$ is a 5-tetrazolyl group or a 5-carboxy-3-pyridyl group, in another class $R^{10}$ is a 5-tetrazolyl group, and $Ar^1$ is a group of formula (aa1):

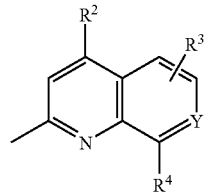

(aa1)

in which $R^2$ and $R^4$ each are independently a hydrogen atom, a halogen atom, a cyclo-lower alkyl group, a lower alkoxy group, a hydroxy-lower alkoxy group, a phenyl group, a pyridyl group or a group of $—N(R^e)R^f$;

In one class, $Ar^1$ is a group of formula (aa1):

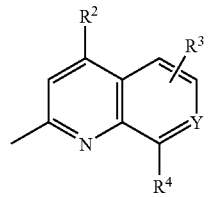

(aa1)

in which $R^2$ is a methoxy group, an ethoxy group, a 2-hydroxyethoxy group, a morpholino group, a phenyl group or a 5-tetrazolyl group, $R^3$ is a hydrogen atom, a fluorine atom, a chlorine atom or a cyano group, or for example a hydrogen atom, and $R^4$ is a chlorine atom, an ethyl group, methoxy group or a cyclopropyl group.

The present invention includes a compound of a formula (Ia):

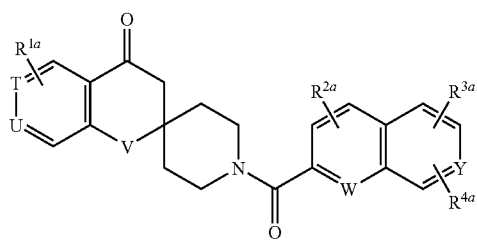

(Ia)

(wherein $R^{1a}$ represents a hydrogen atom, a halogen atom, a cyano group, a lower alkenyl group, a lower alkanoyl group, a lower alkoxycarbonyl group, an aralkyloxycarbonyl group, or a group of $-Q^{1a}-N(R^a)Q^{2a}-R^b$, a lower alkyl group optionally substituted by a substituent selected from a group consisting of a halogen atom, a hydroxy group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, or an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$;

$R^{2a}$, $R^{3a}$ and $R^{4a}$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a cyclo-lower alkyloxy group, a cyclo-lower alkyl-lower alkoxy group, a lower alkylthio group, or a group of —N($R^e$)$R^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower allyl group, a lower alkenyl group, a lower alkoxy group, a halo-lower alkoxy group and a lower alkylthio group;

$Q^{1a}$ and $Q^{2a}$ each independently represent a single bond, or a group of —CO—, —$SO_2$— or —C($R^g$)($R^h$)—; and $R^a$, $R^b$, $R^c$, $R^d$, $R^e$, $R^f$, $R^g$, $R^h$, T, U, W, Y and V have the same meanings as above).

$R^{1a}$ represents a hydrogen atom, a halogen atom, a cyano group, a lower alkenyl group, a lower alkanoyl group, a lower alkoxycarbonyl group, an aralkyloxycarbonyl group, or a group of -$Q^{1a}$-N($R^a$) $Q^{2a}$-$R^b$, or a lower alkyl group optionally substituted by a substituent selected from a group consisting of a halogen atom, a hydroxy group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, or an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$.

The embodiments of the halogen atom, lower alkenyl group, lower alkenyl group, lower alkanoyl group and lower alkoxycarbonyl group for $R^{1a}$ may be respectively the same as those of those groups in the formula (I).

In the group of -$Q^{1a}$-N($R^a$)-$Q^{2a}$-$R^b$ for $R^{1a}$, $Q^{1a}$ and $Q^{2a}$ each independently represent a single bond, or a group of —CO—, —$SO_2$— or —C($R^g$)($R^h$)—. $R^a$, $R^b$, $R^g$ and $R^h$ have the same meanings as above, and also the embodiments of them may be the same as above.

In one class, $Q^{1a}$ is a single bond, —CO—, —$SO_2$— or —C($CH_3$)$_2$—, and $Q^{2a}$ is a single bond, —CO— or —$CH_2$—.

The embodiments of the group of -$Q^{1a}$-N($R^a$)-$Q^{2a}$-$R^b$ for $R^{1a}$ may be the same as those of the group of -$Q^1$-N($R^a$)-$Q^2$-$R^b$ for $R^1$ in the formula (I), namely in the group of -$Q^{1a}$-N($R^a$)-$Q^{2a}$-$R^b$, for example, the case where (i) $Q^{1a}$ and $Q^{2a}$ are a single bond, $R^a$ is a hydrogen atom or a lower alkyl group, and $R^b$ is a heteroaromatic group optionally substituted by a lower alkyl group that is optionally substituted by a substituent selected from a group consisting of a halogen atom, a lower alkoxy group, a carbamoyl group and a lower alkoxycarbonyl group, (ii) $Q^{1a}$ is a single bond, $Q^{2a}$ is a group of —CO—, $R^a$ is a hydrogen atom or a lower alkyl group, and $R^b$ is a hydrogen atom, a lower alkoxy group, a halo-lower alkoxy group, an aralkyloxy group or a group of —N($R^i$)$R^j$, or a lower allyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group, (iii) $Q^{1a}$ is a group of —CO—, $Q^{2a}$ is a single bond, and $R^a$ and $R^b$ each independently are a hydrogen atom or a lower alkyl group, (iv) $Q^{1a}$ is a group of —CO—, $Q^{2a}$ is a group of —C($R^g$)($R^h$)—, $R^a$ is a hydrogen atom or a lower alkyl group, and $R^b$ is a carbamoyl group, or a lower alkyl group optionally substituted by a substituent selected from a group consisting of a halogen atom, a lower alkoxy group, a carbamoyl group and a lower alkoxycarbonyl group, or (v) $Q^{1a}$ is a group of —$SO_2$—, $Q^{2a}$ is a single bond, and $R^a$ and $R^b$ each independently are a hydrogen atom or a lower alkyl group is preferred.

$R^i$ and $R^j$ have the same meanings as above, and also the embodiments of them may be the same as above.

"Lower alkyl group optionally substituted by a substituent selected from a group consisting of a halogen atom, a hydroxy group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group" and "Aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of —CO—N($R^c$)$R^d$" for $R^{1a}$ have the same meanings as those of $R^1$ in the formula (I), and also the embodiments of them may be the same as those.

In one embodiment, $R^{2a}$, $R^{3a}$ and $R^{4a}$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a cyclo-lower alkyloxy group, a cyclo-lower alkyl-lower alkoxy group, a lower alkylthio group, or a group of —N($R^e$)$R^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower alkyl group, a lower alkenyl group, a lower alkoxy group, a halo-lower alkoxy group and a lower alkylthio group.

In another embodiment, $R^{2a}$, $R^{3a}$ and $R^{4a}$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a cyclo-lower alkyloxy group, a cyclo-lower alkyl-lower alkoxy group, a lower alkylthio group, or a group of —N(R$^e$)R$^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower allyl group, a hydroxy-lower alkyl group, a cyclo-lower alkyl group, a lower alkenyl group, a lower alkoxy group, a halo-lower alkoxy group and a lower alkylthio group; provided that at least one of R$^2$, R$^3$ and R$^4$ is lower alkoxy, hydroxy-lower alkoxy, cyclo-lower alkyl, or aryl substituted with at least one lower alkoxy.

The embodiments of the halogen atom, cyclo-lower alkyl group, lower alkenyl group, lower alkoxy group, halo-lower alkoxy group, cyclo-lower alkyloxy group, cyclo-lower alkyl-lower alkoxy group and lower alkylthio group for R$^{2a}$, R$^{3a}$ and R$^{4a}$ may be respectively the same as those of the R$^2$, R$^3$ and R$^4$ groups in the formula (I).

In the group —N(R$^e$)R$^f$ for R$^{2a}$, R$^{3a}$ and R$^{4a}$, R$^e$ and R$^f$ have the same meanings as above, and also the embodiments of them may be the same as above.

The embodiments of the group of —N(R$^e$)R$^f$ for R$^{2a}$, R$^{3a}$ and R$^{4a}$ may be the same as those of the group of —N(R$^e$)R$^f$ for R$^2$, R$^3$ and R$^4$ in the formula (I), "Lower alkyl group optionally having a substituent selected from a group consisting of a halogen atom, a hydroxyl group and a cyclo-lower alkyl group" and "Aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower alkyl group, a lower alkenyl group, a lower alkoxy group, a halo-lower alkoxy group and a lower alkylthio group" for R$^{2a}$, R$^{3a}$ and R$^{4a}$ have the same meanings as those of R$^2$, R$^3$ and R$^4$ in the formula (I), and also the embodiments of them may be the same as those.

T, U, V, W and Y have the same meanings as above. When T, U, W and Y each are a methine group, then the methine group may be substituted by any of R$^{1a}$, R$^{2a}$, R$^{3a}$ or R$^{4a}$.

The embodiments of T, V and W may be the same as those of them in the formula (I).

In the compound of formula (Ia), R$^{1a}$ may be at any substitutable position of the skeleton of the following:

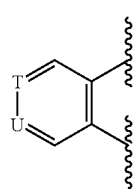

and R$^{2a}$, R$^{3a}$ and R$^{4a}$ may be at any substitutable position of the skeleton of the following:

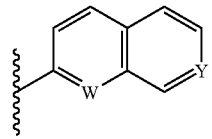

One embodiment of the compound of formula (Ia) is, for example, a compound of the following general formula (Ia-1):

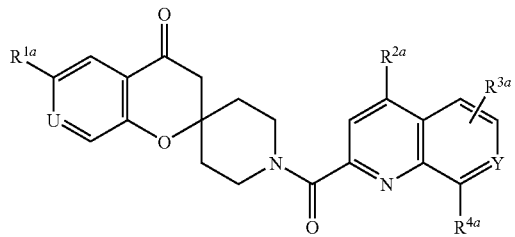

(Ia-1)

wherein R$^{1a}$, R$^{2a}$, R$^{3a}$, R$^{4a}$, U and Y have the same meanings as above.

In formula (Ia-1), embodiments of R$^{1a}$, R$^{2a}$, R$^{3a}$, R$^{4a}$, U and Y may be the same as those of R$^{1a}$, R$^{2a}$, R$^{3a}$, R$^{4a}$, U and Y in formula (I) mentioned hereinabove. In one class, R$^{2a}$ and R$^{4a}$ each are independently a hydrogen atom, a halogen atom, a cyclo-lower alkyl group, a lower alkoxy group, a phenyl group, a pyridyl group or a group of —N(R$^e$)R$^f$; in another class R$^{2a}$ is a methoxy group, an ethoxy group, a 1-pyrrolidinyl group or a phenyl group, R$^{3a}$ is a hydrogen atom, a fluorine atom, a chlorine atom or a cyano group, and R$^{4a}$ is a fluorine atom, a chlorine atom, methoxy group or a cyclopropyl group.

The terms "any substitutable position" or "unlimited substitutable positions" mean positions having substitutable hydrogen(s) on carbon, nitrogen, oxygen and/or sulfur atom(s) where the replacement or substitution of hydrogen is chemically allowed and the replacement or substitution results in a stable compound.

Depending on the type of the substituents therein and on the form of their salts, the compounds of the invention may have their stereoisomers such as optical isomers, diastereomeric isomers and geometrical isomers, or tautomers, and the compounds of the invention encompass all these stereoisomers and tautomers and their mixtures.

The invention encompasses various crystals, amorphous solids, salts, hydrates and solvates of the compounds of the invention.

Further, prodrugs of the compounds of the invention are also within the scope of the invention. In general, such prodrugs are functional derivatives of the compounds of the invention, and they can be readily converted into the compounds that are needed in bodies. Accordingly, the term "administer" as referred to herein for the method of treating various disorders includes not only the administration of a specific compound but also the administration of a compound which, after administered to patients, may be converted into the specific compound in bodies. General methods for selection and production of suitable prodrug derivatives are described, for example, in *Design of Prodrugs*, ed. H. Bundgaard, Elsevier, 1985, and its entire description is referred to and incorporated herein as a part of the specification of the present application. Metabolites of these compounds include active compounds that are produced by leaving the compounds of the invention in a biological environment, and they are within a scope of the invention.

Specific examples of the compounds of formula (I), and their salts and esters are mentioned below:

N-{1'-[(4-methoxyquinolin-2-yl)carbonyl]-4-oxospiro [chroman-2,4'-piperidin]-6-yl}acetamide,
N-{1'-[(4-methoxyquinolin-2-yl)carbonyl]-4-oxospiro [chroman-2,4'-piperidin]-6-yl}acetamide hydrochloride,
N-{1'-[(4,8-dimethoxyquinolin-2-yl)carbonyl]-4-oxospiro [chroman-2,4'-piperidin]-6-yl}acetamide,
1'-[(4,8-dimethoxyquinolin-2-yl)carbonyl]spiro[chroman-2, 4'-piperidin]-4-one,
6-amino-1'-[(4,8-dimethoxyquinolin-2-yl)carbonyl]spiro [chroman-2,4'-piperidin]-4-one,
N-{1'-[(4,8-dimethoxyquinolin-2-yl)carbonyl]-4-oxospiro [chroman-2,4'-piperidin]-6-yl}urea,
1'-[(4,8-Dimethoxyquinolin-2-yl)carbonyl]-4-oxospiro [chroman-2,4'-piperidine]-6-sulfonamide,
1'-[(4,8-dimethoxyquinolin-2-yl)carbonyl]-N-methyl-4-oxospiro[chroman-2,4'-piperidine]-6-sulfonamide,
6-bromo-1'-[(4,8-dimethoxyquinolin-2-yl)carbonyl]spiro [chroman-2,4'-piperidin]-4-one,
1'-[(4,8-dimethoxyquinolin-2-yl)carbonyl]-6-[(1-methyl-1H-pyrazol-5-yl)amino]spiro[chroman-2,4'-piperidin]-4-one,
1'-[(4,8-dimethoxyquinolin-2-yl)carbonyl]-6-[(1-ethyl-1H-pyrazol-5-yl)amino]spiro[chroman-2,4'-piperidin]-4-one,
1'-[(4,8-dimethoxyquinolin-2-yl)carbonyl]-6-pyridin-2-yl-spiro[chroman-2,4'-piperidin]-4-one,
1'-[(4,8-dimethoxyquinolin-2-yl)carbonyl]-6-pyridin-3-yl-spiro[chroman-2,4'-piperidin]-4-one,
5-{1'-[(4,8-dimethoxyquinolin-2-yl)carbonyl]-4-oxospiro [chroman-2,4'-piperidin]-6-yl}nicotinamide,
6-{1'-[(4,8-dimethoxyquinolin-2-yl)carbonyl]-4-oxospiro [chroman-2,4'-piperidin]-6-yl}nicotinamide,
1'-[(4,8-dimethoxyquinolin-2-yl)carbonyl]-4-oxospiro [chroman-2,4'-piperidine]-6-carbonitrile,
1'-[(4,8-dimethoxyquinolin-2-yl)carbonyl]-6-(1H-tetrazol-5-yl)spiro[chroman-2,4'-piperidin]-4-one,
1'-[(4,8-dimethoxyquinolin-2-yl)carbonyl]-6-(1H-tetrazol-5-yl)spiro[chroman-2,4'-piperidin]-4-one sodium salt,
1'-[(4,8-dimethoxyquinolin-2-yl)carbonyl]-6-(1-methyltetrazol-5-yl)spiro[chroman-2,4'-piperidin]-4-one,
1'-[(4,8-dimethoxyquinolin-2-yl)carbonyl]-6-(2-methyltetrazol-5-yl)spiro[chroman-2,4'-piperidin]-4-one,
(5-{1'-[(4,8-dimethoxyquinolin-2-yl)carbonyl]-4-oxospiro [chroman-2,4'-piperidin]-6-yl}-2H-tetrazol-2-yl)methyl pivalate,
(5-{1'-[(4,8-dimethoxyquinolin-2-yl)carbonyl]-4-oxospiro [chroman-2,4'-piperidin]-6-yl}-2H-tetrazol-1-yl)methyl pivalate,
1'-[(8-cyclopropyl-4-ethoxy-1,7-naphthyridin-2-yl)carbonyl]-6-(1H-tetrazol-5-yl)spiro[chroman-2,4'-piperidin]-4-one,
1'-[(4,8-dimethoxyquinolin-2-yl)carbonyl]-6-(5-oxo-4,5-dihydro-1,2,4-oxadiazol-3-yl)spiro[chroman-2,4'-piperidin]-4-one,
1'-[(4,8-dimethoxyquinolin-2-yl)carbonyl]-6-(5-oxo-4,5-dihydro-1H-1,2,4-triazol-3-yl)spiro[chroman-2,4'-piperidin]-4-one,
1'-[(4,8-dimethoxyquinolin-2-yl)carbonyl]-6-(benzyloxycarbonyl)spiro-[chroman-2,4'-piperidin]-4-one,
1'-[(4,8-dimethoxyquinolin-2-yl)carbonyl]-6-(carboxy) spiro[chroman-2,4'-piperidin]-4-one,
1'-[(4,8-dimethoxyquinolin-2-yl)carbonyl]-6-(5-oxo-4,5-dihydro-1,3,4-oxadiazol-2-yl)spiro[chroman-2,4'-piperidin]-4-one,
1'-[(4,8-dimethoxyquinolin-2-yl)carbonyl]-6-(1H-1,2,4-triazol-3-yl)-spiro[chroman-2,4'-piperidin]-4-one,
3-{1'-[(4,8-dimethoxyquinolin-2-yl)carbonyl]-4-oxospiro [chroman-2,4'-piperidin]-6-yl}-1H-1,2,4-triazole-5-carboxamide,
6-(4-acetylpiperazin-1-yl)-1'-[(4,8-dimethoxyquinolin-2-yl) carbonyl]-spiro[chroman-2,4'-piperidin]-4-one,
6-(4-acetylpiperazin-1-yl)-1'-[(4,8-dimethoxyquinolin-2-yl) carbonyl]spiro[chroman-2,4'-piperidin]-4-one,
1'-[(4,8-dimethoxyquinolin-2-yl)carbonyl]-6-[4-(methylsulfonyl)piperazin-1-yl]spiro[chroman-2,4'-piperidin]-4-one,
sodium 3-{1'-[(1-cyclopropyl-5-methoxyisoquinolin-7-yl) carbonyl]-4-oxospiro[chroman-2,4'-piperidin]-6-yl}-5-oxo-1,2,4-oxadiazol-4-ide,
1'-[4-(2-hydroxyethoxy)-8-methoxy-2-naphthoyl]-6-(5-oxo-4,5-dihydro-1,2,4-oxadiazol-3-yl)spiro[chroman-2, 4'-piperidin]-4-one,
1'-[8-methoxy-4-(1H-tetrazol-5-yl)-2-naphthoyl]-6-(1-methyl-1H-pyrazol-4-yl)spiro[chroman-2,4'-piperidin]-4-one,
3-{1'-[(8-cyclopropyl-4-methoxyquinolin-2-yl)carbonyl]-4-oxospiro[chroman-2,4'-piperidin]-6-yl}-1H-1,2,4-triazole-5-carboxamide,
5-{1'-[(8-cyclopropyl-4-methoxyquinolin-2-yl)carbonyl]-4-oxospiro[chroman-2,4'-piperidin]-6-yl}nicotinic acid,
N-(2-amino-2-oxoethyl)-1'-{[1-cyclopropyl-5-(2-hydroxyethoxy)isoquinolin-7-yl]carbonyl}-4-oxospiro[chroman-2,4'-piperidine]-6-carboxamide,
5-(1'-{[8-cyclopropyl-4-(2-hydroxyethoxy)-1,7-naphthyridin-2-yl]carbonyl}-4-oxospiro[chroman-2,4'-piperidin]-6-yl)nicotinamide,
5-{1'-[(1-cyclopropyl-5-methoxyisoquinolin-7-yl)carbonyl]-4-oxospiro[chroman-2,4'-piperidin]-6-yl}nicotinic acid sodium salt,
3-{1'-[(1-cyclopropyl-5-methoxyisoquinolin-7-yl)carbonyl]-4-oxospiro[chroman-2,4'-piperidin]-6-yl}benzoic acid,
1'-(4,8-dimethoxy-2-naphthoyl)-6-(1H-tetrazol-5-yl)spiro [chroman-2,4'-piperidin]-4-one,
1'-(8-methoxy-4-morpholin-4-yl-2-naphthoyl)-6-(1H-tetrazol-5-yl)spiro[chroman-2,4'-piperidin]-4-one,
1"-[(8-methoxy-4-phenylquinolin-2-yl)carbonyl]-6-(H-tetrazol-5-yl)spiro[chroman-2,4'-piperidin]-4-one,
1'-[(8-cyclopropyl-4-methoxyquinolin-2-yl)carbonyl]-6-(1H-tetrazol-5-yl)spiro[chroman-2,4'-piperidin]-4-one,
1'-[(4-ethoxy-8-ethylquinolin-2-yl)carbonyl]-6-(1H-tetrazol-5-yl)spiro[chroman-2,4'-piperidin]-4-one,
1'-[(4-ethoxy-8-ethylquinolin-2-yl)carbonyl]-6-(1H-tetrazol-5-yl)spiro[chroman-2,4'-piperidin]-4-one,
1"'-[(5,8-dichloro-4-ethoxyquinolin-2-yl)carbonyl]-6-(H-tetrazol-5-yl)spiro[chroman-2,4'-piperidin]-4-one,
1'-[(1,5-dimethoxyisoquinolin-7-yl)carbonyl]-6-(1H-tetrazol-5-yl)spiro[chroman-2,4'-piperidin]-4-one,
1'-[(1-cyclopropyl-5-ethoxyisoquinolin-7-yl)carbonyl]-6-(1H-tetrazol-5-yl)spiro[chroman-2,4'-piperidin]-4-one,
sodium 5-{1'-[(1-cyclopropyl-5-ethoxyisoquinolin-7-yl)carbonyl]-4-oxospiro[chroman-2,4'-piperidin]-6-yl}tetrazol-1-ide,
1'-{[1-cyclopropyl-5-(2-hydroxyethoxy)isoquinolin-7-yl] carbonyl}-6-(1H-tetrazol-5-yl)spiro[chroman-2,4'-piperidin]-4-one,
1'-[(4-cyclopropyl-8-ethoxyisoquinolin-6-yl)carbonyl]-6-(1H-tetrazol-5-yl)spiro[chroman-2,4-piperidin]-4-one, 1'-[(4-cyclopropyl-8-methoxyquinolin-6-yl)carbonyl]-6-(1H-tetrazol-5-yl)spiro[chroman-2,4'-piperidin]-4-one,
sodium 5-{1'-[(1-cyclopropyl-5-ethoxyisoquinolin-7-yl)carbonyl]-4-oxospiro[chroman-2,4'-piperidin]-6-yl}nicotinate,
sodium 5-{1'-[(8-cyclopropyl-4-methoxy-quinolin-2-yl)carbonyl]-4-oxospiro[chroman-2,4'-piperidin]-6-yl}nicotinate,
1'-[(4,8-dimethoxyquinolin-2-yl)carbonyl]-6-(1H-pyrazol-4-yl)spiro[chroman-2,4'-piperidin]-4-one,
1'-[(4,8-dimethoxyquinolin-2-yl)carbonyl]-6-(1-methyl-1H-pyrazol-4-yl)spiro[chroman-2,4'-piperidin]-4-one,
1'-[(4,8-dimethoxyquinolin-2-yl)carbonyl]-6-(1,1-dioxidothiomorpholin-4-yl)spiro[chroman-2,4'-piperidin]-4-one,
1'-[(4,8-dimethoxyquinolin-2-yl)carbonyl]-6-(3-oxopiperazin-1-yl)spiro[chroman-2,4'-piperidin]-4-one,
1'-[(4,8-dimethoxyquinolin-2-yl)carbonyl]-6-(4H-1,2,4-triazol-3-ylamino)spiro[chroman-2,4'-piperidin]-4-one,
1''-[(4-hydroxy-8-methoxyquinolin-2-yl)carbonyl]-6-(1H-tetrazol-5-yl)spiro[chroman-2,4'-piperidin]-4-one,
1'-[(8-hydroxy-4-methoxyquinolin-2-yl)carbonyl]-6-(1H-tetrazol-5-yl)spiro[chroman-2,4'-piperidin]-4-one,
1-[(8-cyclopropyl-4-methoxyquinolin-2-yl)carbonyl]-6'-(1H-tetrazol-5-yl)spiro[piperidine-4,2'-thiochroman]-4'-one,
6'-tert-butyl-1-[(4,8-dimethoxyquinolin-2-yl)carbonyl]spiro[piperidine-4,2'-pyrano[2,3-c]pyridin]-4(3'H)-one,
sodium 5-{1'-[(8-cyclopropyl-4-ethoxy-1,7-naphthyridin-2-yl)carbonyl]-4-oxospiro[chroman-2,4'-piperidin]-6-yl}nicotinate,
sodium 2-{1'-[(1-cyclopropyl-5-methoxyisoquinolin-7-yl)carbonyl]-4-oxo-spiro[chroman-2,4'-piperidin]-6-yl}isonicotinate,
sodium 2-{1'-[(1-cyclopropyl-5-ethoxyisoquinolin-7-yl)carbonyl]-4-oxospiro[chroman-2,4'-piperidin]-6-yl}isonicotinate,
4,8-dimethoxy-2-({6-[(methoxycarbonyl)amino]-4-oxospiro[chroman-2,4'-piperidin]-1'-yl}carbonyl)quinoline hydrochloride,
2-{1'-[(4,8-dimethoxyquinolin-2-yl)carbonyl]-4-oxospiro[chroman-2,4'-piperidin]-6-yl}-2-methylpropanoic acid, and
1'-[(1,5-dimethoxyisoquinolin-3-yl)carbonyl]-6-(1H-tetrazol-5-yl)spiro[chroman-2,4'-piperidin]-4-one.

In particular, the compounds of formula (I) include:
1'-[(4,8-dimethoxyquinolin-2-yl)carbonyl]-6-(1H-tetrazol-5-yl)spiro[chroman-2,4'-piperidin]-4-one,
(5-{1'-[(4,8-dimethoxyquinolin-2-yl)carbonyl]-4-oxospiro[chroman-2,4'-piperidin]-6-yl}-2H-tetrazol-2-yl)methyl pivalate,
5-{1'-[(8-cyclopropyl-4-methoxyquinolin-2-yl)carbonyl]-4-oxospiro[chroman-2,4'-piperidin]-6-yl}nicotinic acid,
1'-(8-methoxy-4-morpholin-4-yl-2-naphthoyl)-6-(1H-tetrazol-5-yl)spiro[chroman-2,4'-piperidin]-4-one, and
1'-[(4-ethoxy-8-ethylquinolin-2-yl)carbonyl]-6-(1H-tetrazol-5-yl)spiro[chroman-2,4'-piperidin]-4-one.

Methods for producing the compounds of the invention are described below. The compounds of formula (I) of the invention may be produced according to the production method mentioned below, or according to the methods shown in Examples and Reference Examples given hereinunder, or by methods readily appreciated by one of ordinary skill in the art. Moreover, by utilizing the procedures described herein, one of ordinary skill in the art can readily prepare additional compounds of the present invention claimed herein. However, the production of the compounds of formula (I) of the invention should not be restricted by these reaction examples. The compounds illustrated in the examples are not, however, to be construed as forming the only genus that is considered as the invention.

Production Method

A compound protected with a suitable group (II in the following drawing) is deprotected, and then condensed with an aromatic carboxylic acid of a formula (III):

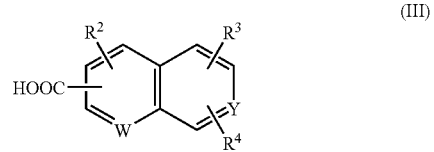

or its reactive derivative according to a chemical process well known in the field of organic chemistry.

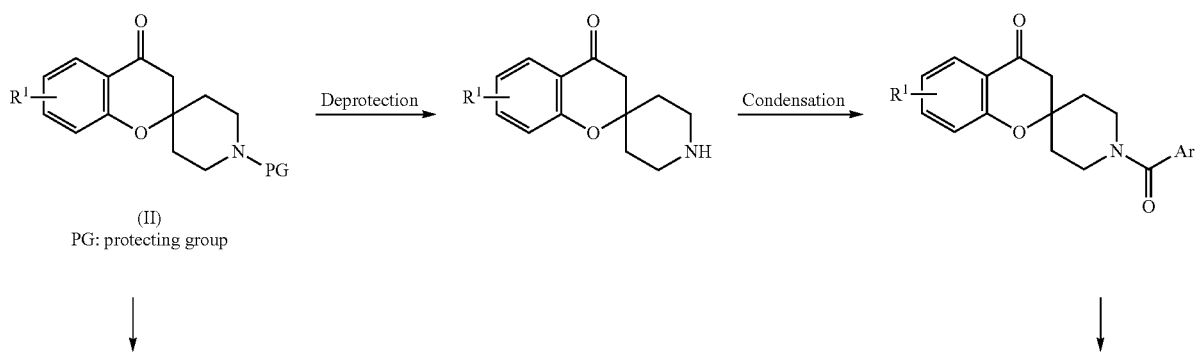

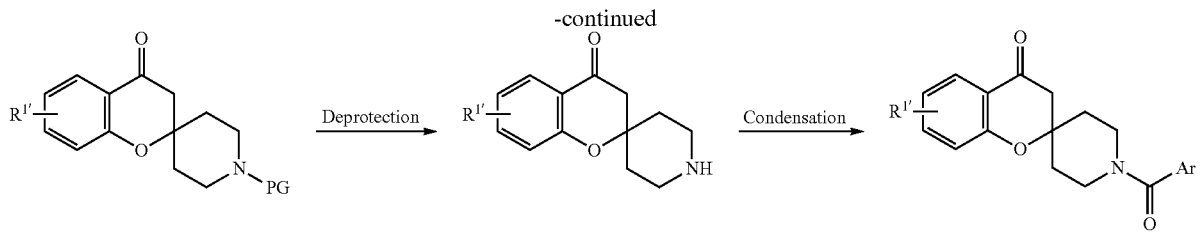

-continued

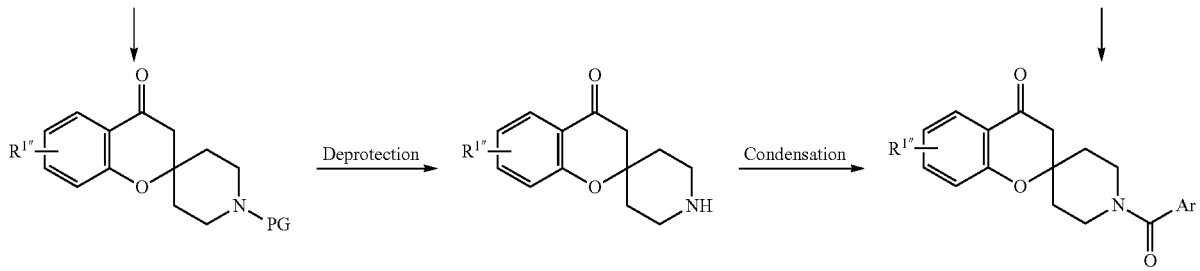

(wherein, Ar represents a group of the following:

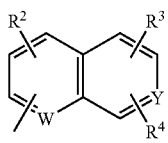

and $R^2$, $R^3$, $R^4$, W and Y have the same meanings as above.)

The protective group (PG) may be, for example, a tert-butoxycarbonyl, benzyloxycarbonyl or benzoyl group, and may also be any other known protective group. For selecting suitable protective groups and their deprotection methods, for example, refer to *Protective Groups in Organic Synthesis* (Theodora W. Greene & Peter G. M. Wuts, John Wiley & Sons, 1999).

In the above series of reactions, the functional groups such as hydroxyl group, amino group, imino group and carboxyl group may be suitably protected, if the group is uninvolved in the specific reaction step, and the protective group may be removed after the reaction step. For the introduction and the removal of the protective groups, to be referred to is the above reference.

The substituent $R^1$ may be converted into a group of any other type ($R^{1'}$, $R^{1''}$) in any suitable step according to a chemical process well known in the field of organic chemistry.

For example, when $R^1$ is a bromo group, it may be converted into a cyano group and may be further changed into a tetrazolyl group. The conversion reaction can be attained according to a chemical process well known in the field of organic chemistry.

The compounds of formulae (II) and (III) may be obtained, for example, as commercial items, or may be prepared using known methods or according to methods similar to known methods, or according to the methods shown in Examples and Reference Examples given hereinunder, optionally as combined.

The compounds of formula (I) may be administered orally or parenterally, and after formulation into preparations suitable for the intended administration route, they can be used as therapeutic agents, for example, for vascular diseases such as hypertension, cardiac angina, heart failure, cardiac infarction, stroke, claudication, diabetic nephropathy, diabetic retinopathy, eyesight failure, electrolyte abnormality and arteriosclerosis, nervous system diseases such as bulimia and diabetic neuropathy; metabolic diseases such as metabolic syndrome, obesity, diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy, sexual dysfunction; digestive tract diseases such as hepatopathy, pancreatitis, cholecystitis and gastroesophageal reflux; respiratory system diseases such as Pickwickian syndrome and sleep apnea syndrome; infectious diseases caused by bacteria, fungi or parasites; malignant neoplasm; and inflammatory diseases such as arthritis and skin ulcer.

The following "diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, ACC1/2 inhibitors may also be useful to treat hypertension associated with this condition.

One aspect of the present invention provides a method for the treatment or prevention of disorders, diseases or conditions responsive to the modulation of ACC-1 or ACC-2 in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of metabolic syndrome, fatty liver, hyperlipemia, dyslipidemia, non-alcoholic fatty liver disease, obesity, diabetes, bulimia, malignant neoplasm or an infectious disease in a subject in need thereof which comprises administering to said subject a therapeutically or prophylactically effective amount of a compound of formula (I), or a pharmaceutically acceptable salt or ester thereof.

Another aspect of the present invention provides a method for the treatment of metabolic syndrome, fatty liver, hyperlipemia, obesity, diabetes, bulimia, malignant neoplasm or infectious diseases, which comprises administering to a subject in need thereof a therapeutically effective amount of the compound or its salt or ester of claim 1.

Another aspect of the present invention provides a method for the treatment or prevention of diabetes in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of obesity in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of hyperlipemia or dyslipidemia in a subject in need thereof which comprises administering to the subject a therapeutically or prophylactically effective amount of a compound of formula (I), or a pharmaceutically acceptable salt or ester thereof.

Another aspect of the present invention provides a method for caloric intake in a subject in need thereof which comprises administering to the subject a therapeutically or prophylactically effective amount of a compound of formula (I), or a pharmaceutically acceptable salt or ester thereof. Another aspect of the present invention provides a method for reducing food intake in a subject in need thereof which comprises administering to the subject a therapeutically or prophylactically effective amount of a compound of formula (I), or a pharmaceutically acceptable salt or ester thereof. Another aspect of the present invention provides a method for increasing satiety in a subject in need thereof which comprises administering to the subject a therapeutically or prophylactically effective amount of a compound of formula (I), or a pharmaceutically acceptable salt or ester thereof. Another aspect of the present invention provides a method for reducing appetite in a subject in need thereof which comprises administering to the subject a therapeutically or prophylactically effective amount of a compound of formula (I), or a pharmaceutically acceptable salt or ester thereof.

The present invention also relates to methods for treating or preventing obesity by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing diabetes by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing hyperlipemia or dyslipidemia by administering a compound of formula (I), or a pharmaceutically acceptable salt or ester thereof, in combination with a therapeutically or prophylactically effective amount of another agent known to be useful to treat or prevent the condition.

Another aspect of the present invention provides a pharmaceutical composition comprising a compound of formula (I), or a pharmaceutically acceptable salt or ester thereof, and a pharmaceutically acceptable carrier.

Yet another aspect of the present invention relates to a compound of formula (I), or a pharmaceutically acceptable salt or ester thereof, for use in medicine.

Yet another aspect of the present invention relates to the use of a compound of formula (I), or a pharmaceutically acceptable salt or ester thereof, for the manufacture of a medicament useful for the treatment or prevention, or suppression of a disease mediated by ACC-1 or ACC-2 in a subject in need thereof.

Yet another aspect of the present invention relates to the use of a compound of formula (I), or a pharmaceutically acceptable salt or ester thereof, for the manufacture of a medicament useful for the treatment or prevention of metabolic syndrome, hyperlipemia, dyslipidemia, non-alcoholic fatty liver disease, obesity, diabetes, bulimia, malignant neoplasm or an infectious disease in a subject in need thereof.

Yet another aspect of the present invention relates to the use of a compound of formula (I), or a pharmaceutically acceptable salt or ester thereof, for the manufacture of a medicament useful for the treatment or prevention of obesity in a subject in need thereof.

Yet another aspect of the present invention relates to the use of a compound of formula (I), or a pharmaceutically acceptable salt or ester thereof, for the manufacture of a medicament useful for the treatment or prevention of diabetes in a subject in need thereof.

Yet another aspect of the present invention relates to the use of a compound of formula (I), or a pharmaceutically acceptable salt or ester thereof, for the manufacture of a medicament useful for the treatment or prevention of hyperlipemia or dyslipidemia in a subject in need thereof.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes, a diabetes related disorder, or an obesity-related disorder in a subject in need of such treatment.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, PYY3-36, and a NK-1 antagonist, or a pharmaceutically acceptable salt thereof, for the manufacture of a medicament for treatment or prevention of obesity, diabetes, a diabetes related disorder, or an obesity-related disorder which comprises an effective amount of a compound of formula (I), or a pharmaceutically acceptable salt or ester thereof, and an effective amount of the agent, together or separately.

Yet another aspect of the present invention relates to a product containing a therapeutically effective amount of a compound of formula (I), or a pharmaceutically acceptable salt or ester thereof; and and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, a diabetes related disorder, or an obesity-related disorder.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)-benzonitrile, 3-((4-chlorophenyl) {3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

In clinical use of the compounds of the invention, pharmaceutically-acceptable additives may be added thereto to formulate various preparations in accordance with the intended administration route thereof, and the preparations may be administered. Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals including humans and other mammals and plants that require the treatment with the compound. For the mammals, humans are preferred and they may be either men or women. The mammals except humans are, for example, companion animals such as dogs and cats. The compounds of the invention are effective also for obesity and obesity-related disorders of dogs and cats. Any ordinary physicians, veterinarians and clinicians may readily determine the necessity, if any, of the treatment with the compound of the invention.

When the compound of the invention is, for example, put into clinical use, then its dose and its administration frequency may vary depending on the sex, the age, the body weight and the condition of the patient and on the type and the range of the necessary treatment with the compound. In oral administration, in general, the dose of the compound may be from 0.01 to 100 mg/kg of adult/day, preferably from 0.03 to 1 mg/kg of adult/day, and the administration frequency is preferably from one to a few times; and in parenteral administration, the dose may be from 0.001 to 10 mg/kg of adult/day, preferably from 0.001 to 0.1 mg/kg of adult/day, more preferably from 0.01 to 0.1 mg/kg of adult/day, and the administration frequency is preferably from one to a few times. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing obesity and/or diabetes mellitus and/or hyperlipemia and/or dyslipidemia and/or non-alcoholic fatty liver disease, or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Ordinary physicians, veterinarians and clinicians may readily determine the effective dose of the pharmaceutical compound necessary to treat, prevent, inhibit, retard or stop the intended disease, and may readily treat the diseased patient with the compound.

The preparation may contain the compound of the invention in an amount of from 1.0 to 100% by weight, preferably from 1.0 to 60% by weight of the preparation. The preparation may contain any other therapeutically-effective compound.

In their use, the compounds of the invention may be combined with any other therapeutic agents that are useful for the treatment of disorders, for example, vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, pre-diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy and sexual dysfunction; digestive tract diseases such as liver dysfunction, pancreatitis, cholecystitis and gastroesophageal reflux; respiratory system diseases such as Pickwickian syndrome and sleep apnea syndrome; infectious diseases caused by bacteria, fungi or parasites; malignant neoplasm; and inflammatory diseases such as arthritis and skin ulcer. The individual ingredients to be combined may be administered at the same time or at different times during the treatment period, either as one preparation or as different preparations. Accordingly, the invention should be so interpreted that it encompasses any and every administration mode at the same time or at different times, and the administration in the invention should be interpreted so. The range of the combination of the compound of the invention and the other therapeutic agent useful for the above-mentioned disorders encompasses, in principle, all combinations of the compound of the invention and any and every pharmaceutical agent useful for the above-mentioned disorders.

The combination includes not only the composition of compounds of the invention and one other active substance but also the composition of compounds of the invention and two or more other active substances. There are a lot of examples of the combinations of a compound of the invention and one, two or more active substances selected from the therapeutic agents for the above-mentioned disorders. For example, for the treatment, management and prevention of metabolic syndrome, a combination of a compound of the invention and one, two or more active substances selected from hypolipidemic agents, lipid lowering agents, and antidiabetic agents is useful. In particular, a composition that also contains an anti-obesity agent and an anti-hypertension agent, in addition to an anti-diabetic agent and/or a hypolipidemic agent or lipid lowering agent, may exhibit a synergistic effect for treatment, management and prevention of metabolic syndrome.

The pharmaceutical agents that may be combined with the compound of the invention are, for example, ACAT inhibitor, α-blocker, aldose reductase inhibitor, α-amylase inhibitor, angiotensin-converting enzyme inhibitor, angiotensin receptor antagonist, anion exchange resin, anorectic, antioxidant, antiplatelet, β-blocker, biguanide agent, calcium antagonist, CB1 receptor inverse agonist/antagonist, CETP inhibitor, cholesterol absorption inhibitor, DGAT inhibitor, DP-IV inhibitor, diuretic, eicosapentaenoic acid, endothelin antagonist, FLAP inhibitor, FXR modulator, Ghrelin antagonist, GLP-1 agonist, GLP-1 secretagogue, glucagon antagonist, glucokinase activator, glucocorticoid receptor ligand, α-glucosidase inhibitor, GPAT inhibitor, histamine-H3 receptor ligand, HMG-CoA reductase inhibitor, HSD inhibitor, insulin and insulin mimetics, kinase inhibitors such as VEGF inhibitor and PDGF inhibitor, leptin, lipase inhibitor, 5-LO inhibitor, LXR ligand, melanocortin agonist, MCH antagonist, MTTP inhibitor, orexin antagonist, opioid antagonist, neuropeptide Y antagonist, nicotinic acid agonist, PPAR ligand, PTP-1B inhibitor, SCD-1 inhibitor, serotonin transporter inhibitor, SGLT inhibitor, SUR ligand, thyroid hormone agonist, UCP activator, VPAC receptor agonist.

More concretely, examples of the other active ingredients that can be combined with a compound of the invention as different or the same pharmaceutical compositions are shown below, which, however, do not restrict the invention.

(a) Anti-diabetic medicines or agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD), and PPAR-γ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and A1-3688; (8) insulin secretagogues such as linogliride, A-4166 and the like; (9) fatty acid oxidation inhibitors such as clomoxir, and etomoxir; (10) a-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (12) non-thiazolidinediones such as JT-501, farglitazar (GW-2570/GI-262579), and muraglitazar; PPAR α/δagonists, such as muraglitazar, and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118).

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agonists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTCO179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, FI6828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naftopidil, indoramin, WHIP164, and XEN010; (11) α2 agonists such as lofexidine, tiamenidine, moxonidine, rilmenidine, and guanobenz; (12) aldosterone inhibitors; and (d) anti-obesity agents, for example, (1) 5HT (serotonin) transporter inhibitors such as paroxetine, fluoxetine, fenfluramine, fluvoxamine, sertraline, and imipramine; (2) NE (norepinephrine) transporter inhibitors such as GW320659, despiramine, talsupram, nomifensine, and the like; (3) CB-1 (cannabinoid-1 receptor) antagonists/inverse agonists such as rimonabant (Sanofi Synthelabo), SR-147778 (Sanofi Synthelabo), BAY65-2520 (Bayer), SLV319 (Solvey); and the compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, WO04/048317, WO05/000809, and EPO NO. EP-658546, EP656354, EP576357; (4) ghrelin antagonists such as those disclosed in WO01/87335, WO02/08250; (5) H3 (histamine H3) antagonists/inverse agonists such as thioperamide, 3-(1H-imidazol-4-yl)propyl N-(4-pentenyl) carbamate, clobenpropit, iodophenpropit, imoproxifan, GT2394 (Gliatech), A331440, and those disclosed in WO02/15905, O-[3-(1H-imidazol-4-yl)propanol]carbamates (Kiec-Kononowicz, K. et al., *Pharmazie,* 55:349-355 (2000)), piperidine-containing histamine H3-receptor antagonists (Lazewska, D. et al., *Pharmazie,* 56:927-932 (2001)), benzophenone derivatives and related compounds (Sasse, A. et al., *Arch. Pharm.* (Weinheim) 334:45-52 (2001)), substituted N-phenylcarbamates (Reidemeister, S. et al., Pharmazie, 55:83-86 (2000)), and proxifan derivatives (Sasse, A. et al., *J. Med. Chem.,* 43:3335-3343 (2000)); (6) melanin-concentrating hormone-1 receptor (MCH1R) antagonists such as T-226296 (Takeda), SNP-7941 (Synaptic), and those disclosed in WO01/82925, WO01/87834, WO02/051809, WO02/06245, WO02/076929, WO02/076947, WO02/04433, WO02/51809, WO02/083134, WO02/094799, WO03/004027, and Japanese Patent Application No. JP13226269, JP2004-139909; (7) MCH2R (melanin-concentrating hormone 2R) agonists/antagonists; (8) NPY1 (neuropeptide Y Y1) antagonists such as BIBP3226, 2-[1-(5-chloro-3-isopropyloxycarbonylaminophenyl)ethylamino]-6-[2-(5-ethyl-4-methyl-1,3-thiazol-2-yl)ethyl]-4-morpholinopyridine, BIB03304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; (9) NPY5 (neuropeptide Y Y5) antagonists such as L-152,804, GW-569180A, GW-594884A, GW-587081×, GW-548118×, FR235,208, FR-226928, FR240662, FR252384, 1229U91, GI-264879A, CGP71683A, LY-377897, LY366377, PD-160170, SR-120562A, SR-120819A, JCF-104, H409/22, and the compounds disclosed in U.S. Pat. Nos. 6,057,335, 6,043,246, 6,140,354, 6,166,038, 6,180,653, 6,191,160, 6,258,837, 6,313,298, 6,337,332, 6,329,395, 6,340,683, 6,326,375, 6,329,395, 6,337,332, 6,335,345, 6,388,077, 6,462,053, 6,649,624, 6,723,847, EPO EP-01010691, EP-01044970, PCT WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/094789, WO02/094825, WO03/014083, WO03/10191, WO03/092889, WO2004/002986, WO2004/031175, and Norman et al., *J. Med. Chem.*, 43:4288-4312 (2000); (10) leptins such as recombinant human leptin (PEG-OB, Hoffman La Roche), and recombinant methionyl human leptin (Amgen); (11) leptin derivatives such as those disclosed in U.S. Pat. Nos. 5,552,524, 5,552,523, 5,552,522, 5,521,283, PCT WO96/23513, WO96/23514, WO96/23515, WO96/23516, WO96/23517, WO96/23518, WO96/23519, and WO96/23520; (12) opioid antagonists such as nalmefene (Revex®), 3-methoxynaltrexone, naloxone, naltrexone, and the compounds disclosed in WO00/21509; (13) orexin antagonists such as SB-334867-A, and the compounds disclosed in WO01/96302, WO01/68609, WO02/51232, WO02/51838, and WO03/023561; (14) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (15) CCK-A (cholecystokinin-A) agonists such as AR-R15849, GI181771, JMV-180, A-71378, A-71623, SR146131, and the compounds disclosed in U.S. Pat. No. 5,739,106; (16) CNTF (ciliary neurotrophic factors) such as GI-181771 (Glaxo-SmithKline), SR146131 (Sanofi Synthelabo), butabindide, and PD170292 and PD149164 (Pfizer); (17) CNTF derivatives such as axokine (Regeneron), and the compounds disclosed in WO94/09134, WO98/22128, and WO99/43813; (18) GHS (growth hormone secretagogue receptor) agonists such as NN703, hexarelin, MK-0677, SM-130686, CP-424,391, L-692,429, L-163,255, and the compounds disclosed in U.S. Pat. Nos. 5,536,716, 6,358,951, USP Application Nos. 2002/049196, 2002/022637, WO01/56592, and WO02/32888; (19) 5HT2c (serotonin receptor 2c) agonists such as BVT933, DPCA37215, IK264, PNU22394, WAY161503, R-1065, YM348, and the compounds disclosed in U.S. Pat. No. 3,914,250, WO02/36596, WO02/48124, WO02/10169, WO01/66548, WO02/44152, WO02/51844, WO02/40456, and WO02/40457; (20) Mc3r (melanocortin-3 receptor) agonists; (21) Mc4r (melanocortin-4 receptor) agonists such as CHIR86036 (Chiron), ME-10142 and ME-10145 (Melacure), PT-141 and PT-14 (Palatin), and the compounds disclosed in U.S. Pat. Nos. 6,410,548, 6,294,534, 6,350,760, 6,458,790, 6,472,398, 6,376,509, and 6,818,658, USP Application No. US2002/0137664, US2003/0236262, US2004/009751, US2004/0092501, WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847, WO04/024720, WO04/078716, WO04/078717, WO04/087159, WO04/089307 and WO05/009950; (22) monoamine reuptake inhibitors such as sibutramine (Meridia®/Reductil®) and its salts, and the compounds disclosed in U.S. Pat. Nos. 4,746,680, 4,806,570, 5,436,272, USP Publication No. 2002/0006964, and WO01/27068, and WO01/62341; (23) serotonin reuptake inhibitors such as dexfenfluramine, fluoxetine, paroxetine, sertraline, and the compounds disclosed in U.S. Pat. No. 6,365,633, and WO01/27060, and WO01/162341; (24) GLP-1 (glucagon-like peptide-1) agonists; (25) topiramate (Topimax®); (26) Phytopharm compound 57 (CP644,673); (27) ACC2 (acetyl-CoA carboxylase-2) inhibitors; (28) β3 (β-adrenergic receptor-3) agonists such as AD9677/TAK677 (Dainippon/Takeda), CL-316, 243, SB418790, BRL-37344, L-796568, BMS-196085, BRL-35135A, CGP12177A, BTA-243, GW427353, trecadrine, Zeneca D7114, SR59119A, and the compounds disclosed in USP Application No. 5,705,515, U.S. Pat. No. 5,451,677, and WO94/18161, WO95/29159, WO97/46556, WO98/04526, WO98/32753, WO01/74782 and WO02/32897; (29) DGAT1 (diacylglycerol acyltransferase-1) inhibitors; (30) DGAT2 (diacylglycerol acyltransferase-2) inhibitors; (31) FAS (fatty acid synthase) inhibitors such as cerulenin, C75; (32) PDE (phosphodiesterase) inhibitors such as theophylline, pentoxifylline, zaprinast, sildenafil, aminone, milrinone, cilostamide, rolipram, and cilomilast; (33) thyroid hormone-β agonists such as KB-2611 (KaroBioBMS), and the compounds disclosed in WO02/15845 and Japanese Patent Application No. JP2000256190; (34) UCP-1 (uncoupling protein-1), 2 and 3 activators such as phytanic acid, 4-[(E)-2-(5,6,7,8-tetrahydro-5,5,8,8-tetramethyl-2-naphthalenyl)-1-propenyl] benzoic acid (TTNPB), retinoic acid, and the compounds disclosed in WO99/00123; (35) acyl-estrogens such as oleoyl-estrones disclosed in del Mar-Grasa, M. et al., *Obesity Research,* 9:202-209 (2001); (36) glucocorticoid antagonists; (37) 11βHSD-1 (11-β-hydroxysteroid dehydrogenase type 1) inhibitors such as BVT3498, BVT2733, and the compounds disclosed in WO01/90091, WO01/90090, and WO01/90092, and U.S. Pat. No. 6,730,690 and USP Application No. 2004/0133011; (38) SCD-1 (stearoyl-CoA desaturase-1) inhibitors; (39) dipeptidyl peptidase IV (DP-IV) inhibitors such as isoleucine thiazolidide, valine pyrrolidide, NVP-DPP728, LAF237, P93/01, TSL225, TMC-2A/2B/2C, FE999011, P9310/K364, VIP0177, SDZ274-444, and the compounds disclosed in U.S. Pat. No. 6,699,871, WO03/004498, WO03/004496, EP1258476, WO02/083128, WO02/062764, WO03/000250, WO03/002530, WO03/002531, WO03/002553, WO03/002593, WO03/000180, and WO03/000181; (40) lipase inhibitors such as tetrahydrolipstatin (orlistat/Xenical®), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267, and the compounds disclosed in WO01/77094, U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; (44) phosphate transporter inhibitors; (45) melanocortin agonists such as melanotan II and the compounds described in WO99/64002, and WO00/746799; (46) melanin condensating hormone antagonists such as the compounds disclosed in WO01/21577 and WO01/21169; (47) galanin antagonists; (48) CCK agonists; (49) corticotropin-releasing hormone agonists; and (50) phosphodiesterase-3B (PDE3B) inhibitors; (51) 5HT-2 agonists; (52) histamine receptor-3 (H3) modulators; (53) β-hydroxy steroid dehydrogenase-1 inhibitors (β-HSD-1); (54) anti-obesity serotonergic agents, such as fenfluramine, dexfenfluramine, phentermine, and sibutramine; (55) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. Nos. 5,026,685, 5,604,203, 5,574,010, 5,696,093, 5,936,092, 6,046,162, 6,046,167, 6,093,692, 6,225,445, 5,604,203, 4,002,531, 4,179,337, 5,122,614, 5,349,052, 5,552,520, 6,127,355, WO 95/06058, WO 98/32466, WO 03/026591, WO 03/057235, WO 03/027637, and WO 2004/066966, which are incorporated herein by reference; (56) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (57) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (58) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (59) a minorex; (60) amphechloral; (61) amphetamine; (62) benzphetamine; (63) chlorphentermine; (64) clobenzorex; (65) cloforex; (66) clominorex; (67) clortermine; (68) cyclexedrine; (69) dextroamphetamine; (70) diphemethoxidine, (71) N-ethylamphetamine; (72) fenbutrazate; (73) fenisorex; (74) fenproporex; (75) fludorex; (76) fluminorex; (77) furfurylmethylamphetamine; (78) levamfetamine; (79) levophacetoperane; (80) mefenorex; (81) metamfepramone; (82) methamphetamine; (83) norpseudoephedrine; (84) pentorex; (85) phendimetrazine; (86) phenmetrazine; (87) picilorex; (88) zonisamide, and (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and 90) Qnexa.

The present agent may be combined with non-drug therapy such as kinesitherapy, dietetic treatment, and radiation therapy.

The compound and the combined compositions of the invention are effective for treating and preventing diabetes. The term "diabetes" as used herein includes both insulin-dependent diabetes (that is, also known as IDDM, type-1 diabetes), and insulin-independent diabetes (that is, also known as NIDDM, type-2 diabetes).

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

The compounds and compositions of the invention are useful for treatment of both type-1 diabetes and type-2 diabetes. The compounds and compositions are especially useful for treatment of type-2 diabetes. The compounds and compositions of the invention are especially useful for treatment and/or prevention of pre-diabetes. Also, the compounds and compositions of the invention are especially useful for treatment and/or prevention of gestational diabetes mellitus.

Treatment of diabetes mellitus refers to the administration of a compound or combination of the present invention to treat a diabetic subject. One outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes. Yet another outcome of treatment is to increase hepatic insulin sensitivity.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Dyslipidemia includes atherogenic dyslipidemia. Hyperlipidemia is associated with abnormally high levels of lipids, LDL and VLDL cholesterol, and/or triglycerides. An outcome of the treatment of dyslipidemia, including hyperlipemia, is to reduce an increased LDL cholesterol concentration. Another outcome of the treatment is to increase a low-concentration of HDL cholesterol. Another outcome of treatment is to decrease very low density lipoproteins (VLDL) and/or small density LDL.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "obesity" as used herein is a condition in which there is an excess of body fat, and includes visceral obesity. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians than that in Europeans and Americans. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be decreasing body fat, including visceral body fat. Another outcome of treatment may be preventing body weight gain. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The invention is described more concretely with reference to its examples mentioned below, which, however, do not restrict the invention.

Mass spectrum is determined according to an electrospray ionization (ESI) method, using Micromass ZQ (Waters).

Abbreviations in Examples have the following meanings: N is normal, M is molar; h is hour(s); Celite is the tradename for diatomaceous earth; aq is aqueous; THF is tetrahydrofuran; DMF is dimethylformamide; TEA is triethylamine; TFA is trifluoroacetic acid; HOBT is 1-hydroxy-benzotriazole; EDCI is ethyl 3-(dimethylamino)propyl carbodiimide hydrochloride; EDC-HCl is 1-(3-dimethylaminopropyl)-3-ethyl-carbodiimide hydrochloride; EtOH is ethanol; MeOH is methanol; EtOAc is ethyl acetate; $Et_3N$ is triethylamine; Pd/C is palladium-carbon catalyst; DMSO is dimethyl sulfoxide; DMAP is 4-(dimethylamino)pyridine; AcOH is acetic acid; $PPh_3$ is triphenyl phosphine; DIAD is diisopropyl azodicarboxylate; WSC is ethyl 3-dimethylaminopropyl carbodiimide hydrochloride; dppf: 1,1'-bis(diphenylphosphino)ferrocene ligand; CDI is 1,1'-carbonyldiimidazole; Ac is acetyl group; Boc is tert-butoxycarbonyl group; $Et_2O$ is diethyl ether; $Ph_2O$ is diphenyl ether; h is hour; MS 4A is molecular sieves 4A; NMO is N-methyl morpholine; TPAP is tetrapropylammonium perruthenate; and KOAc is potassium acetate.

EXAMPLE 1

N-{1'-[(4-methoxyquinolin-2-yl)carbonyl]-4-oxospiro[chroman-2,4'-piperidin]-6-yl}acetamide

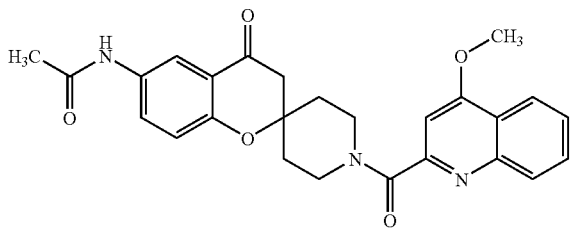

63.3 g of EDCI was added to a mixture of 16.5 g of 4-oxospiro[chroman-2,4'-piperidin]-6-ylacetamide TFA salt, 61.0 g of 4-methoxyquinoline-2-carboxylic acid, 45.9 g of HOBT, 50 mL of Et$_3$N and 90 mL DMF, at 0° C., and the resulting mixture was stirred at room temperature for 14 hours. The reaction mixture was concentrated under reduced pressure, and the residue was partitioned between ethyl acetate and water. The organic layer was washed with water and aqueous saturated sodium carbonate solution successively, then dried over sodium sulfate, and then concentrated. The residue was purified through silica gel column chromatography (eluted with 3% MeOH/CHCl$_3$), and the intended compound was obtained. $^1$H-NMR (300 MHz, CDCl$_3$) δ: 8.21 (1H, dd, J=8.5, 1.3 Hz), 7.99 (1H, dd, J=8.5, 1.0 Hz), 7.94 (1H, dd, J=8.9, 2.7 Hz), 7.73 (1H, ddd, J=8.5, 6.9, 1.3 Hz), 7.67 (1H, d, J=2.7 Hz), 7.55 (1H, ddd, J=8.5, 6.9, 1.0 Hz), 7.34 (1H, br.s), 7.09 (1H, s), 7.01 (1H, d, J=8.9 Hz), 4.65-4.55 (1H, m), 4.09 (3H, s), 4.06-3.96 (1H, m), 3.58 (1H, dt, J=2.9, 12.7 Hz), 3.36 (1H, dt, J=2.9, 12.7 Hz), 2.83-2.69 (2H, m), 2.26-2.12 (1H, m), 2.17 (3H, s), 2.10-2.00 (1H, m), 1.96-1.75 (2H, m). MS [M+H]$^+$=460.

EXAMPLE 2

N-{1'-[(4-methoxyquinolin-2-yl)carbonyl]-4-oxospiro[chroman-2,4'-piperidin]-6-yl}acetamide hydrochloride

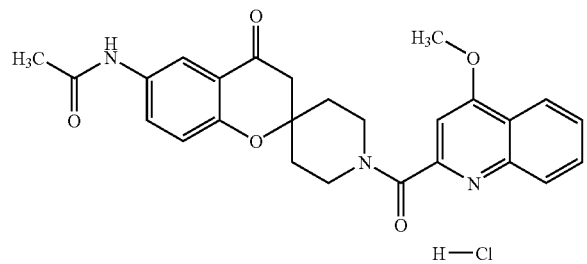

14.0 g of the compound obtained in Example 1 was dissolved in CHCl$_3$ (80 mL)-MeOH (20 mL), to which was added 4 N HCl/EtOAc (15 mL), and the resulting mixture was concentrated. The residue was dissolved in 30 mL of MeOH, and 50 mL of water was added to it at 0° C., stirred at room temperature for 18 hours. The resulting precipitate was taken out through filtration, washed with 30% MeOHaq and dried in vacuum to obtain the intended compound. $^1$H-NMR (300 MHz, DMSO-d$_6$) δ: 10.04 (1H, s), 8.24 (1H, d, J=8.5 Hz), 8.09 (1H, d, J=8.3 Hz), 8.01 (1H, d, J=2.7 Hz), 7.96-7.89 (1H, m), 7.77-7.69 (2H, m), 7.38 (1H, s), 7.06 (1H, d, J=8.9 Hz), 4.37-4.26 (1H, m), 4.18 (3H, s), 3.60-3.39 (2H, m), 3.37-3.22 (1H, m), 2.88 (2H, s), 2.13-1.98 (1H, m), 2.02 (3H, s), 1.94-1.75 (3H, m). MS [M+H]$^+$=460.

EXAMPLE 3

N-{1'-[(4,8-dimethoxyquinolin-2-yl)carbonyl]-4-oxospiro[chroman-2,4'-piperidin]-6-yl}acetamide

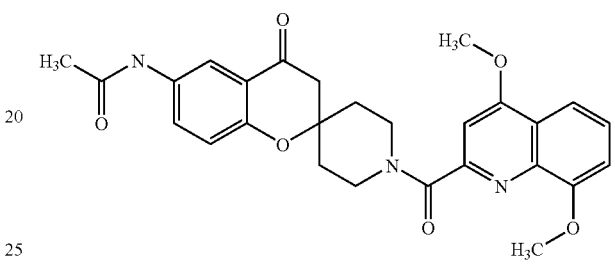

The intended compound was produced according to the method of Example 1 but using, as the starting material, 4,8-dimethoxyquinoline-2-carboxylic acid in place of 4-methoxyquinoline-2-carboxylic acid. $^1$H-NMR (300 MHz, DMSO-d$_6$) δ: 9.97 (1H, s), 8.00 (1H, d, J=2.7 Hz), 7.72 (1H, dd, J=2.7, 9.0 Hz), 7.68 (1H, d, J=8.3 Hz), 7.52 (1H, dd, J=8.3, 7.9 Hz), 7.23 (1H, d, J=7.9 Hz), 7.18 (1H, s), 7.07 (1H, d, J=9.0 Hz), 4.36-4.25 (1H, m), 4.07 (3H, s), 3.94 (3H, s), 3.68-3.57 (1H, m), 3.49-3.21 (2H, m), 2.88 (2H, s), 2.11-1.97 (1H, m), 2.02 (3H, s), 1.94-1.72 (3H, m). MS [M+H]$^+$=490.

EXAMPLE 4

1'-[(4,8-dimethoxyquinolin-2-yl)carbonyl]spiro[chroman-2,4'-piperidin]-4-one

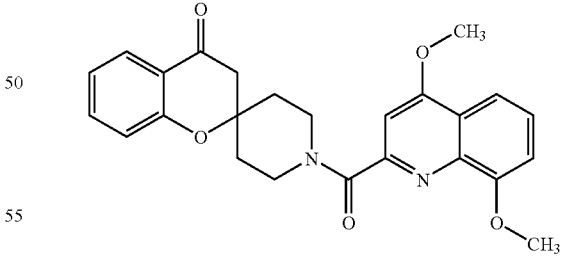

The intended compound was produced according to the method of Example 3 but using, as the starting material, spiro[chroman-2,4'-piperidin]-4-one in place of 4-oxospiro[chroman-2,4'-piperidin]-6-ylacetamide TFA salt. $^1$H-NMR (300 MHz, CDCl$_3$) δ: 7.88 (1H, dd, J=8.0, 1.7 Hz), 7.77 (1H, d, J=8.3 Hz), 7.45-7.55 (1H, m), 7.47 (1H, dd, J=8.3, 7.9 Hz), 7.18 (1H, s), 7.07 (1H, d, J=7.9 Hz), 6.95-7.05 (2H, m), 4.50-4.65 (1H, m), 4.10-4.20 (1H, m), 4.08 (3H, s), 4.03 (3H, s), 3.55-3.70 (1H, m), 3.30-3.45 (1H, m), 2.82 (1H, d, J=16.6

Hz), 2.75 (1H, d, J=16.6 Hz), 2.15-2.30 (1H, m), 2.00-2.15 (1H, m), 1.80-1.95 (2H, m). MS [M]⁺=432.

EXAMPLE 5

6-amino-1'-[(4,8-dimethoxyquinolin-2-yl)carbonyl]spiro[chroman-2,4'-piperidin]-4-one

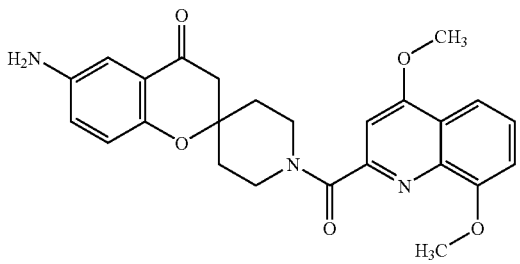

3.78 g of benzyl {1'-[(4,8-dimethoxyquinolin-2-yl)carbonyl]-4-oxospiro[chroman-24'-piperidin]-6-yl}carbamate was dissolved in 20 mL of THF and 40 mL of MeOH, and hydrogenated on 10% Pd/C at room temperature. Pd/C was removed through filtration, and the filtrate was concentrated to obtain the intended compound. $^1$H-NMR (CDCl$_3$) δ: 7.77 (1H, dd, J=8.5, 1.2 Hz), 7.47 (1H, t, J=8.0 Hz), 7.17 (1H, s), 7.15 (1H, d, J=2.9 Hz), 7.08 (1H, dd, J=7.8, 1.0 Hz), 6.91 (1H, dd, J=8.8, 2.9 Hz), 6.85 (1H, d, J=8.8 Hz), 4.56 (1H, d, J=13.2 Hz), 4.16-4.08 (1H, m), 4.08 (3H, s), 4.03 (3H, s), 3.63-3.53 (3H, m), 3.34 (1H, td, J=12.8, 3.3 Hz), 2.76 (1H, d, J=16.5 Hz), 2.70 (1H, d, J=16.5 Hz), 2.20 (1H, dd, J=13.9, 2.7 Hz), 2.05 (1H, dd, J=13.9, 2.7 Hz), 1.88-1.78 (2H, m). MS [M+H]⁺= 448.

EXAMPLE 6

N-{1'-[(4,8-dimethoxyquinolin-2-yl)carbonyl]-4-oxospiro[chroman-2,4'-piperidin]-6-yl}urea

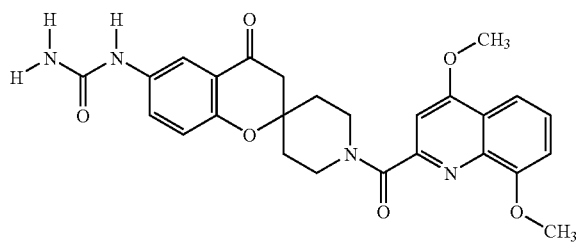

The compound of Example 5 (1.35 g) was dissolved in 15 mL of THF; and 0.505 mL of NEt$_3$ and 669 mg of 4-nitrophenyl chloroformate were added thereto in order, and stirred at room temperature. The reaction mixture was filtered, and 0.226 mL of 25% aqueous ammonia was added to the filtrate, and stirred overnight at room temperature. The reaction solution was diluted with chloroform, washed with water, dried over magnesium sulfate, and concentrated. The residue was purified through silica gel thin-layer chromatography (CHCl$_3$/MeOH=7/1) to obtain the intended compound as a yellow amorphous solid. $^1$H-NMR (400 MHz, DMSO-d$_6$) δ: 8.59 (1H, s), 7.80 (1H, d, J=2.9 Hz), 7.66 (1H, dd, J=8.5, 1.5 Hz), 7.53 (1H, dd, J=8.6, 3.0 Hz), 7.50 (1H, t, J=8.4 Hz), 7.22 (1H, dd, J=8.0, 2.0 Hz), 7.16 (1H, s), 6.99 (1H, d, J=8.8 Hz), 5.83 (2H, s), 4.21-4.36 (1H, m), 4.05 (3H, s), 3.93 (3H, s), 3.64-3.55 (1H, m), 3.46-3.32 (1H, m), 3.31-3.20 (1H, m), 2.84 (2H, s), 2.08-1.99 (1H, m), 1.91-1.84 (1H, m), 1.83-1.70 (2H, m). MS [M+H]⁺=491.

EXAMPLE 7

1'-[(4,8-Dimethoxyquinolin-2-yl)carbonyl]-4-oxospiro[chroman-2,4'-piperidine]-6-sulfonamide

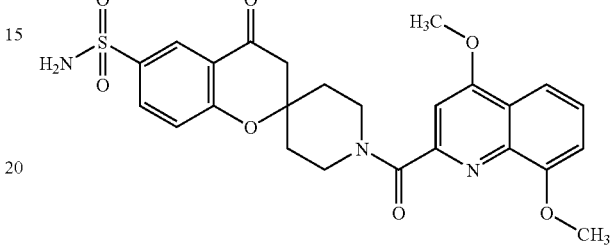

The intended compound was produced according to the method of Example 3 but using, as the starting material, 4-oxospiro[chroman-2,4'-piperidine]-6-sulfonamide HCl salt in place of 4-oxospiro[chroman-2,4'-piperidin]-6-ylacetamide TFA salt. $^1$H-NMR (300 MHz, CDCl$_3$) δ: 8.38-8.46 (1H, m), 8.07-8.00 (1H, m), 7.80-7.75 (1H, m), 7.51-7.43 (1H, m), 7.19 (1H, s), 7.17-7.04 (2H, m), 5.28 (2H, s), 4.61-4.52 (1H, m), 4.20-4.10 (1H, m), 4.08 (3H, s), 4.02 (3H, s), 3.65-3.55 (1H, m), 3.40-3.29 (1H, m), 2.90-2.78 (2H, m), 2.23-2.12 (1H, m), 2.10-1.85 (3H, m). MS [M+H]⁺=512.

EXAMPLE 8

1'-[(4,8-dimethoxyquinolin-2-yl)carbonyl]-N-methyl-4-oxospiro[chroman-2,4'-piperidine]-6-sulfonamide

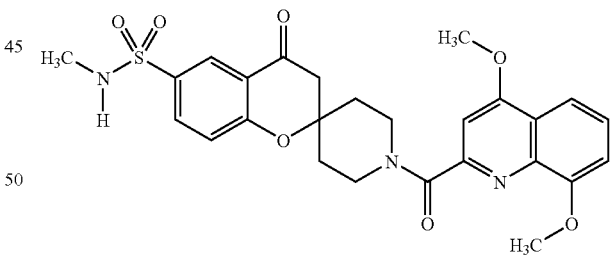

293 mg of 1'-[(4,8-Dimethoxyquinolin-2-yl)carbonyl]-4-oxospiro[chroman-2,4'-piperidine]-6-sulfonamide was dissolved in 5 mL of CHCl$_3$, and 10.7 mg of DMAP and 120 mg of EDCI were added to it, and then 0.036 mL of AcOH was added thereto and the mixture was stirred overnight at room temperature. Aqueous saturated sodium hydrogen carbonate was added to the reaction solution, and then extracted three times with ethyl acetate, and the organic layer was washed successively with aqueous saturated sodium hydrogencarbonate solution, water and saturated brine. The aqueous layers were combined, hydrochloric acid was added to it to thereby make it have a pH of 7.5, and this was then extracted with CHCl$_3$. The extract was dried over sodium sulfate and concentrated, and the resulting residue was purified through silica gel column chromatography (CHCl$_3$, 4.5% MeOH/CHCl$_3$) to obtain 317 mg of N-acetyl-1'-[(4,8-dimethoxyquinolin-2-yl)carbonyl]-4-oxospiro[chroman-2,4'-piperidine]-6-sulfonamide. 26.3 mg of the product was dissolved in 1.5 mL of THF, and 15.0 mg of PPh$_3$, 0.011 mL of DIAD and 2.7 mL of MeOH were added to it and the mixture was stirred at room temperature for one day. The reaction solution was concentrated and purified through silica gel thin-layer chromatography (n-Hexane/EtOAc=1/5) to obtain 26.3 mg of N-acetyl-1'-[(4,8-dimethoxyquinolin-2-yl)carbonyl]-N-methyl-4-oxospiro[chroman-2,4'-piperidine]-6-sulfonamide as a colorless foam substance. This was dissolved in 0.8 mL of MeOH and 0.1 mL of water, added by 0.1 mL of saturated sodium hydrogen carbonate solution, and then stirred for 2 hours. The reaction solution was diluted with water and extracted with CHCl$_3$. The organic layer was dried over sodium sulfate, and concentrated, and the residue was purified through silica gel thin-layer chromatography (CHCl$_3$/MeOH=18/1) to obtain the intended compound as a colorless foam substance. $^1$H-NMR (300 MHz, CDCl$_3$) δ: 8.40-8.38 (1H, m), 8.01-7.97 (1H, m), 7.80-7.74 (1H, m), 7.51-7.43 (1H, m), 7.20 (1H, s), 7.17-7.13 (1H, m), 7.11-7.06 (1H, m), 4.67-4.58 (2H, m), 4.28-4.18 (1H, m), 4.09 (3H, s), 4.03 (3H, s), 3.67-3.56 (1H, m), 3.44-3.33 (1H, m), 2.92-2.78 (2H, m), 2.68 (3H, d, J=5.4 Hz), 2.28-2.17 (1H, m), 2.13-1.88 (3H, m). MS [M+H]$^+$=526.

EXAMPLE 9

6-bromo-1'-[(4,8-dimethoxyquinolin-2-yl)carbonyl]spiro[chroman-2,4'-piperidin]-4-one

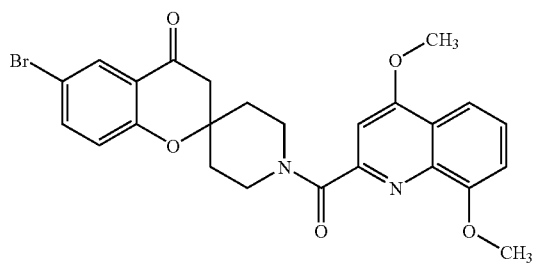

The intended compound was produced according to the method of Example 3 but using, as the starting material, 6-bromospiro[chroman-2,4'-piperidin]-4-one HCl salt in place of 4-oxospiro[chroman-2,4'-piperidin]-6-ylacetamide TFA salt. $^1$H-NMR (300 MHz, CDCl$_3$) δ: 8.00 (1H, d, J=2.5 Hz), 7.79 (1H, d, J=8.4 Hz), 7.60 (1H, dd, J=8.8, 2.5 Hz), 7.48 (1H, dd, J=8.4, 7.8 Hz), 7.20 (1H, s), 7.09 (1H, d, J=7.8 Hz), 6.94 (1H, d, J=8.8 Hz), 4.55-4.65 (1H, m), 4.10-4.25 (1H, m), 4.09 (3H, s), 4.04 (3H, s), 3.50-3.70 (1H, m), 3.30-3.45 (1H, m), 2.83 (1H, d, J=16.8 Hz), 2.75 (1H, d, J=16.8 Hz), 2.15-2.30 (1H, m), 2.00-2.15 (1H, m), 1.80-2.00 (2H, m). MS [M]$^+$=510.

EXAMPLE 10

1'-[(4,8-dimethoxyquinolin-2-yl)carbonyl]-6-[(1-methyl-1H-pyrazol-5-yl)amino]spiro[chroman-2,4'-piperidin]-4-one

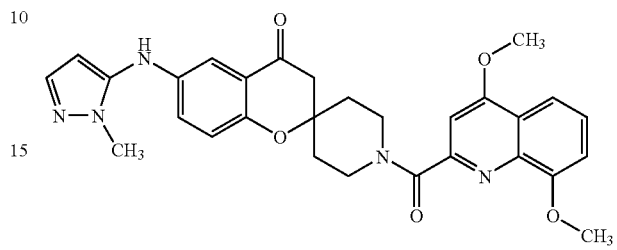

The bromide compound (2.00 g) produced in Example 9, 5-amino-1-methyl-1H-pyrazole (456 mg), palladium acetate (175 mg), 2-(di-t-butylphosphino)biphenyl (233 mg) and cesium carbonate (1.66 g) were suspended in 1,4-dioxane (20 mL), and heated under reflux at 120° C. for 40 hours. The reaction liquid was filtered through Celite, the residue on the Celite was washed with chloroform, and the filtrate was concentrated under reduced pressure. The resulting residue was purified through silica gel column chromatography (developed with solvents of ethyl acetate/acetone=6/4 and chloroform/methanol=99/1 in order) to obtain the intended compound as a yellow amorphous solid. $^1$H-NMR (400 MHz, CDCl$_3$) δ: 7.77 (1H, dd, J=8.3, 1.0 Hz), 7.49-7.43 (2H, m), 7.22 (1H, d, J=2.8 Hz), 7.17 (1H, s), 7.08 (1H, dd, J=7.8, 1.0 Hz), 6.97 (1H, dd, J=8.8, 2.8 Hz), 6.91 (1H, d, J=8.8 Hz), 5.97 (1H, d, J=2.0 Hz), 5.42 (1H, s), 4.60-4.52 (1H, m), 4.18-4.10 (1H, m), 4.07 (3H, s), 4.03 (3H, s), 3.68 (3H, s), 3.65-3.55 (1H, m), 3.40-3.29 (1H, m), 2.77 (1H, d, J=16.6 Hz), 2.71 (1H, d, J=16.6 Hz), 2.25-2.15 (1H, m), 2.10-2.02 (1H, m), 1.92-1.79 (2H, m). MS [M+H]$^+$=528.

EXAMPLE 11

1'-[(4,8-dimethoxyquinolin-2-yl)carbonyl]-6-[(1-ethyl-1H-pyrazol-5-yl)amino]spiro[chroman-2,4'-piperidin]-4-one

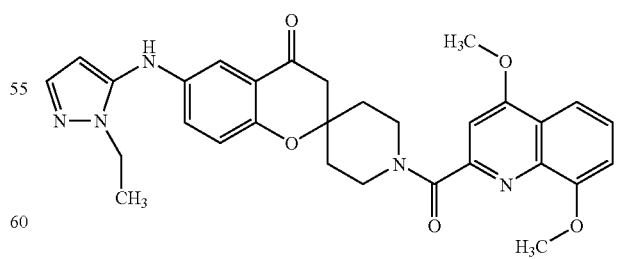

The intended compound was produced according to the method of Example 10 but using, as the starting material, 5-amino-1-ethyl-1H-pyrazole in place of 5-amino-1-methyl-1H-pyrazole. $^1$H-NMR (300 MHz, CDCl$_3$) δ: 7.77 (1H, d, J=8.4 Hz), 7.47 (1H, dd, J=8.4, 7.8 Hz), 7.46-7.50 (1H, m), 7.22 (1H, d, J=2.8 Hz), 7.17 (1H, s), 7.08 (1H, d, J=7.8 Hz), 6.88-6.98 (2H, m), 5.98 (1H, d, J=1.9 Hz), 5.17 (1H, s), 4.50-4.65 (1H, m), 4.07 (3H, s), 4.05-4.20 (1H, m), 4.05 (2H, q, J=7.3 Hz), 4.03 (3H, s), 3.50-3.65 (1H, m), 3.25-3.40 (1H, m), 2.88 (1H, d, J=16.6 Hz), 2.71 (1H, d, J=16.6 Hz), 2.15-2.25 (1H, m), 2.00-2.10 (1H, m), 1.75-1.79 (2H, m), 1.39 (3H, t, J=7.3 Hz). MS [M]$^+$=541.

EXAMPLE 12

1'-[(4,8-dimethoxyquinolin-2-yl)carbonyl]-6-pyridin-3-yl-spiro[chroman-2,4'-piperidi]-4-one

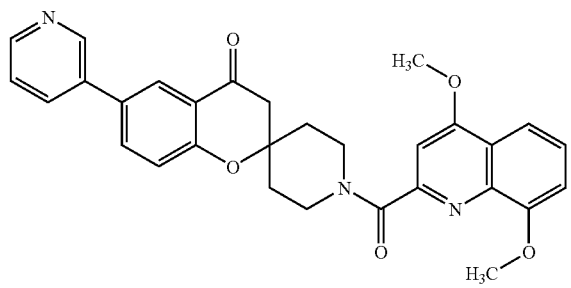

6-Bromo-1'-[(4,8-dimethoxyquinolin-2-yl)carbonyl]spiro[chroman-2,4'-piperidin]-4-one (200 mg), pyridine-3-boronic acid-1',3'-propanediol cyclic ester (76.6 mg) and Pd(PPh$_3$)$_4$ (45.2 mg) were suspended in a mixture of 1,4-dioxane (1.6 mL) and aqueous 2 M sodium carbonate solution (0.8 mL), and heated under reflux at 110° C. for 12 hours. The reaction solution was partitioned between ethyl acetate and water, extracted with ethyl acetate, washed with saturated brine, and dried with magnesium sulfate. The desiccant was removed through filtration, the filtrate was concentrated under reduced pressure, and the resulting residue was purified through thin-layer chromatography (chloroform/methanol=95/5) to obtain the intended compound. $^1$H-NMR (300 MHz, CDCl$_3$) δ: 8.83 (1H, d, J=1.7 Hz), 8.59 (1H, dd, J=4.8, 1.7 Hz), 8.10 (1H, d, J=2.4 Hz), 7.82-7.90 (1H, m), 7.77 (1H, m), 7.76 (1H, d, J=8.6, 2.4 Hz), 7.47 (1H, dd, J=8.2, 7.8 Hz), 7.36 (1H, dd, J=7.8, 4.8 Hz), 7.19 (1H, s), 7.15 (1H, d, J=8.6 Hz), 7.08 (1H, d, J=7.8 Hz), 4.55-4.65 (1H, m), 4.10-4.25 (1H, m), 4.08 (3H, s), 4.03 (3H, s), 3.55-3.70 (1H, m), 3.30-3.45 (1H, m), 2.87 (1H, d, J=16.7 Hz), 2.80 (1H, d, J=16.7 Hz), 2.20-2.30 (1H, m), 2.05-2.20 (1H, m), 1.80-2.00 (2H, m). MS [M]$^+$=509.

EXAMPLE 13

5-{1'-[(4,8-dimethoxyquinolin-2-yl) carbonyl]-4-oxospiro[chroman-2,4'-piperidin]-6-yl}nicotinamide

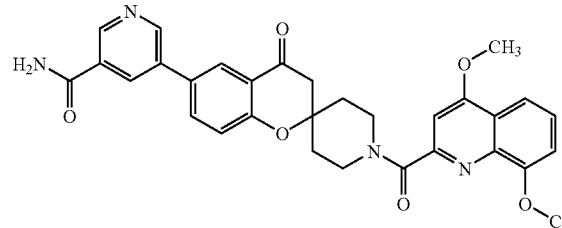

350 mg of 1'-[(4,8-dimethoxyquinolin-2-yl)carbonyl]-6-(4,4,5,5-tetramethyl-1,3,2-dioxaborolan-2-yl)spiro[chroman-2,4'-piperidin]-4-one, 151 mg of 5-bromonicotinamide, 72.5 mg of Pd(PPh$_3$)$_4$ and 1.4 mL of 2M Na$_2$CO$_3$aq were heated with 1,4-dioxane at 100° C. and stirred for 21 hours. The reaction solution was diluted with CHCl$_3$, filtered through Celite, and the filtrate was dried with magnesium sulfate and concentrated. The residue was purified through silica gel thin-layer chromatography (CHCl$_3$/MeOH=9/1) to obtain the intended compound. $^1$H-NMR (400 MHz, CDCl$_3$) δ: 8.90-9.00 (2H, m), 8.36 (1H, s), 8.15 (1H, s), 7.70-7.80 (2H, m), 7.40-7.55 (11H, m), 7.19 (1H, s), 7.17 (1H, d, J=8.8 Hz), 7.09 (1H, d, J=7.8 Hz), 6.3-6.5 (1H, br), 5.7-6.1 (1H, br), 4.50-4.60 (1H, m), 4.10-4.15 (1H, m), 4.08 (3H, s), 4.03 (3H, s), 3.55-3.70 (1H, m), 3.35-3.50 (1H, m), 2.88 (1H, d, J=16.6 Hz), 2.82 (1H, d, J=16.6 Hz), 2.20-2.30 (1H, m), 2.05-2.15 (1H, m), 1.80-2.05 (2H, m). MS [M+H]$^+$=553.

EXAMPLE 14

1'-[(4,8-dimethoxyquinolin-2-yl)carboyl]-6-pyrimidin-2-yl-spiro[chroman-2,4'-piperidin]-4-one

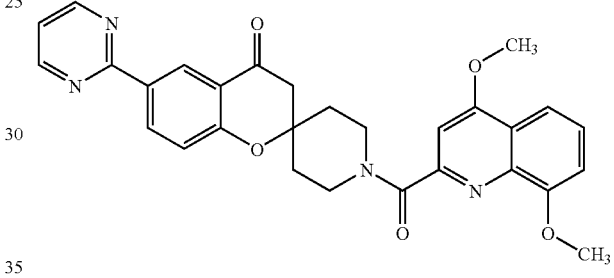

The intended compound was produced according to the method of Example 13 but using 2-bromopyrimidine in place of 5-bromonicotinamide. $^1$H-NMR (300 MHz, CDCl$_3$) δ: 9.01 (1H, d, J=2.2 Hz), 8.79 (2H, d, J=4.8 Hz), 8.62 (1H, dd, J=8.7, 2.2 Hz), 7.78 (1H, dd, J=8.4, 1.0 Hz), 7.48 (1H, dd, J=8.4, 7.8 Hz), 7.20 (1H, s), 7.18 (1H, dd, J=4.8, 4.8 Hz), 7.15 (1H, d, J=8.7 Hz), 7.08 (1H, d, J=7.8 Hz), 4.55-4.65 (1H, m), 4.10-4.25 (1H, m), 4.09 (3H, s), 4.04 (3H, s), 3.55-3.75 (1H, m), 3.35-3.50 (1H, m), 2.89 (1H, d, J=16.6 Hz), 2.81 (1H, d, J=16.6 Hz), 2.20-2.35 (1H, m), 2.05-2.20 (1H, m), 1.85-2.05 (2H, m). MS [M]$^+$=510.

EXAMPLE 15

6-{1'-[(4,8-dimethoxyquinolin-2-yl)carbonyl]-4-oxospiro[chroman-2,4'-piperidin]-6-yl}nicotinamide

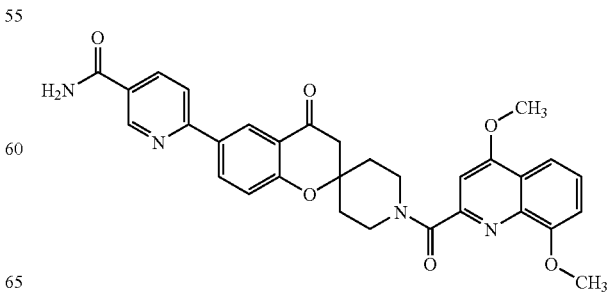

The intended compound was produced according to the method of Example 13 but using 6-chloronicotinamide in place of 5-bromonicotinamide. $^1$H-NMR (400 MHz, CDCl$_3$) δ: 9.06 (1H, s), 8.51 (1H, s), 8.34 (1H, d, J=8.8 Hz), 8.21 (1H, d, J=8.3 Hz), 7.83 (1H, d, J=8.3 Hz), 7.77 (1H, d, J=8.3 Hz), 7.47 (1H, dd, J=8.3, 7.8 Hz), 7.19 (1H, s), 7.16 (1H, d, J=8.8 Hz), 7.07 (1H, d, J=7.8 Hz), 6.1-6.4 (1H, br), 5.7-6.0 (1H, br), 4.50-4.60 (1H, m), 4.15-4.25 (1H, m), 4.08 (3H, s), 4.03 (3H, s), 3.55-3.75 (1H, m), 3.30-3.50 (1H, m), 2.88 (1H, d, J=16.6 Hz), 2.81 (1H, d, J=16.6 Hz), 2.20-2.30 (1H, m), 2.05-2.15 (1H, m), 1.85-2.05 (2H, m). MS [M+H]$^+$=553.

EXAMPLE 16

1'-[(4,8-dimethoxyquinolin-2-yl)carbonyl]-4-ox-ospiro[chroman-2,4'-piperidine]-6-carbonitrile

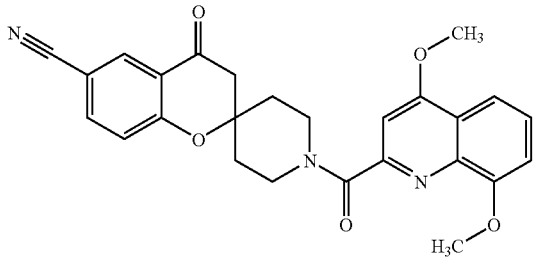

118 mg of zinc cyanide, 69.3 mg of Pd(PPh$_3$)$_4$ and 3 mL of DMF were added to 511 mg of the bromo compound obtained in Example 9, and heated under a nitrogen atmosphere at 80° C., and the reaction mixture was stirred for 39 hours. After cooled, the reaction mixture was diluted with 30 mL of ethyl acetate, washed successively with diluted aqueous ammonia, water and saturated brine, then dried over sodium sulfate, and concentrated. Ethyl ether was added to the resulting residue, and the insoluble solid thus formed was taken out through filtration. This was washed with ethyl ether and dried under reduced pressure to obtain the intended compound as a pale yellow-brown solid. $^1$H-NMR (300 MHz, CDCl$_3$) δ: 8.20 (1H, d, J=2.0 Hz), 7.71 (1H, d, J=8.2 Hz), 7.74 (1H, dd, J=8.6, 2.0 Hz), 7.42 (1H, t, J=8.2 Hz), 7.19 (1H, s), 7.13 (1H, d, J=8.6 Hz), 7.08 (1H, d, J=8.2 Hz), 4.63-4.54 (1H, m), 4.26-4.17 (1H, m), 4.08 (3H, s), 4.03 (3H, s), 3.64-3.52 (1H, m), 3.42-3.29 (1H, m), 2.88 (1H, d, J=16.8 Hz), 2.81 (1H, d, J=16.8 Hz), 2.23-2.13 (1H, m), 2.09-1.85 (3H, m). MS [M+H]$^+$=458.

EXAMPLE 17

1'-[(4,8-dimethoxyquinolin-2-yl)carbonyl]-6-(1H-tetrazol-5-yl)spiro[chroman-2,4'-piperidin]-4-one

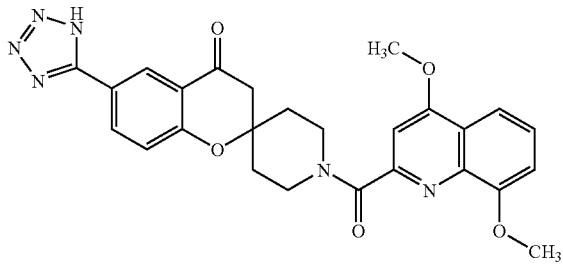

To a mixture of 4,8-Dimethoxyquinoline-2-carboxylic acid potassium salt (10.65 g, 38.5 mmol, reference Example 58) in DMF (100 mL) was added 5.5 N HCl in isopropanol (8.19 mL, 45 mmol). The mixture was aged at room temperature for 20-35 minutes, followed by the sequential addition of 6-(1H-tetrazol-5-yl)spiro[chroman-2,4'-piperidine]-4-one hydrochloride salt (11.92 g, 36.3 mmol, reference Example 59), HOBT (5.84 g, 38.1 mmol), DMF (5 mL rinse), and triethyl amine (7.59 mL, 54.5 mmol). The mixture was aged at room temperature for 20 minutes, then 26 mL of water were added while cooling with ice water to mitigate the exotherm, followed by the addition of EDC-HCl (11 g, 57.4 mmol) in several portions. The pH was adjusted to between 5.8 and 6.1, and the reaction was aged at room temperature between 75 minutes and overnight until complete. 150 mL of water was added slowly and the resulting mixture was aged between 22-26° C. for 30 minutes to 1 hour. The mixture was filtered, washed with 60 mL of water, 60 mL of 1:1 water/CH$_3$CN, and 60 mL of CH$_3$CN, and dried in vacuo to give the intended compound as a colorless solid. The product maybe further purified by dissolving in methanol, heating to 65° C., treating with 6 N HCl at 55° C., reheating to 65° C., then cooling to 25° C., at which time water is added and the mixture is cooled to 0-2° C. and aged for 1 hour. The resulting slurry may be filtered and washed with 1:1 methanol/water, then dried. The solid may be re-suspended in water, treated with 2N NaOH to slowly adjust the pH to pH 5 over several hours, then aged at room temperature for 1-2 hours, filtered, rinsed with water and methanol and dried to give the intended product.

Alternatively, 6-(1H-tetrazol-5-yl)spiro[chroman-2,4'-piperidin]-4-one hydrochloride (20.0 g, 56.5 mmol), 4,8-dimethoxyquinolin-2-carboxylic acid (13.2 g, 56.5 mmol), EDCI (11.9 g, 62.1 mmol), HOBT (9.44 g, 62.1 mmol), and TEA (23.7 mL, 170 mmol) were suspended in DMF (200 mL) at 0° C. and stirred at room temperature for 3 days. The reaction mixture was poured into H$_2$O (3 L)-1N HCl aq. (113 mL, 113 mmol) and further stirred for 1 h. The resulted precipitate was filtered and washed with H$_2$O to give crude intended compound as a pale brown solid. This solid was further washed with EtOAc/MeOH (50 mL-200 mL) to obtain the intended compound as a pale brown solid.

Alternatively, 195 mg of sodium azide, 413 mg of triethylamine hydrochloride and 5 mL of DMF were added to nitrile derivative (458 mg) produced in Example 16, and stirred at 100° C. under a nitrogen atmosphere for 20 hours. After cooled, the mixture was added by 30 mL of water and 0.60 mL of aqueous 5 N sodium hydroxide solution, then the mixture was washed five times with chloroform (10 mL each). 0.60 mL of 5 N hydrochloric acid was added to the aqueous layer, and the mixture was extracted with chloroform. The extract was washed with saturated brine, dried over sodium sulfate, and concentrated. The resulting residue was purified through silica gel chromatography (chloroform/methanol=50/1 to 30/1, chloroform/methanol/acetic acid=300/100/1), the fraction containing it was concentrated, and ethyl ether was added to the residue. The resulting insoluble material was taken out through filtration, washed with ethyl ether, and dried under reduced pressure to obtain the intended compound as a pale yellow powder. $^1$H-NMR (300 MHz, DMSO-d$_6$) δ: 8.44 (1H, d, J=2.3 Hz), 8.26 (1H, dd, J=8.6, 2.3 Hz), 7.69 (1H, dd, J=8.4, 1.1 Hz), 7.53 (1H, dd, J=8.4, 7.8 Hz), 7.38 (1H, d, J=8.6 Hz), 7.25 (1H, dd, J=7.8, 1.1 Hz), 7.21 (1H, s), 4.38-4.30 (1H, m), 4.08 (3H, s), 3.95 (3H, s), 3.70-3.62 (1H, m), 3.52-3.43 (1H, m), 3.38-3.28 (1H, m), 3.02 (2H, s), 2.15-2.08 (1H, m), 1.99-1.82 (3H, m). MS [M+H]$^+$=501.

EXAMPLE 18

1'-[(4,8-dimethoxyquinolin-2-yl)carbonyl]-6-(1H-tetrazol-5-yl)spiro[croman-2,4'-piperidin]-4-one sodium salt

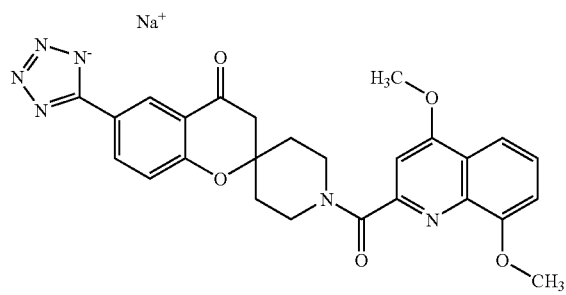

The compound obtained in Example 17 (604 mg) was suspended in 30 mL of water, and saturated sodium hydrogen carbonate solution was added thereto until the resulting mixture was clear. The thus-obtained solution was purified through octadecyl-silica gel chromatography (water:water/acetonitrile=1:1) to obtain the intended compound as a pale yellow-brown powder. $^1$H-NMR (300 MHz, DMSO-$d_6$) δ: 8.32 (1H, d, J=2.2 Hz), 8.16 (1H, dd, J=8.6, 2.2 Hz), 7.68 (1H, d, J=8.4 Hz), 7.52 (1H, dd, J=8.4, 7.9 Hz), 7.23 (1H, d, J=7.9 Hz), 7.19 (1H, s), 7.13 (1H, d, J=8.6 Hz), 4.37-4.27 (1H, m), 4.07 (3H, s), 3.95 (3H, s), 3.69-3.58 (1H, m), 3.52-3.28 (2H, m), 2.93 (2H, s), 2.16-2.05 (1H, m), 1.99-1.75 (3H, m). MS [M+H]$^+$=501.

EXAMPLE 19

1'-[(4,8-dimethoxyquinolin-2-yl)carbonl]-6-(1-methyltetrazol-5-yl)spiro[chroman-2,4'-piperidin]-4-one, and 1'-[(4,8-dimethoxyquinolin-2-yl)carbonyl]-6-(2-methyltetrazol-5-yl)spiro[chroman-2,4'-piperidin]-4-one (1-isomer)

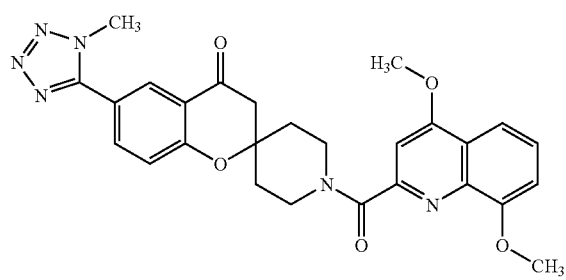

(2-isomer)

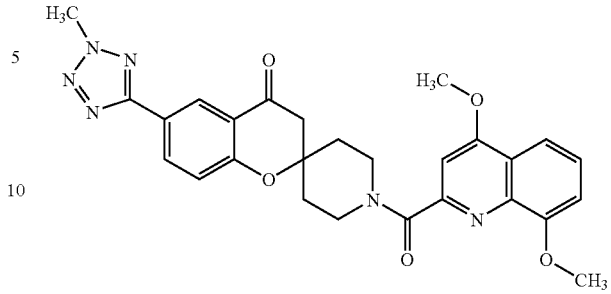

The sodium salt (15.7 mg) obtained in Example 18 was dissolved in 0.3 mL of DMF, 0.009 mL of methyl iodide was added to it, and the mixture was stirred at room temperature for 13 hours. The reaction mixture was concentrated, and the residue was diluted with ethyl acetate, washed with water and saturated brine in order, then dried over sodium sulfate, and concentrated. The residue was purified through silica gel chromatography (chloroform/methanol=10/1) to obtain 1'-[(4,8-dimethoxyquinolin-2-yl)carbonyl]-6-(1-methyltetrazol-5-yl)spiro[chroman-2,4'-piperidin]-4-one (this is referred to as 1-isomer) and 1'-[(4,8-dimethoxyquinolin-2-yl)carbonyl]-6-(2-methyltetrazol-5-yl)spiro[chroman-2,4'-piperidin]-4-one (this is referred to as 2-isomer) both as colorless powders. 1-Isomer: $^1$H-NMR (CDCl$_3$) δ: 8.20 (1H, d, J=2.3 Hz), 8.05 (1H, dd, J=8.5, 2.3 Hz), 7.78 (1H, d, J=8.4 Hz), 7.48 (1H, dd, J=8.4, 7.9 Hz), 7.25 (1H, d, J=8.5 Hz), 7.20 (1H, s), 7.09 (1H, d, J=7.9 Hz), 4.67-4.57 (1H, m), 4.29-4.18 (1H, m), 4.22 (3H, s), 4.09 (3H, s), 4.04 (3H, s), 3.69-3.58 (1H, m), 3.46-3.33 (1H, m), 2.91 (1H, d, J=16.8 Hz), 2.84 (1H, d, J=16.8 Hz), 2.30-2.20 (1H, m), 2.16-1.88 (3H, m). MS [M+H]$^+$=515.2-Isomer: $^1$H-NMR (CDCl$_3$) δ: 8.65 (1H, d, J=2.3 Hz), 8.29 (1H, dd, J=8.7, 2.3 Hz), 7.77 (1H, d, J=8.5 Hz), 7.47 (1H, dd, J=8.5, 7.6 Hz), 7.19 (1H, s), 7.15 (1H, d, J=8.7 Hz), 7.08 (1H, d, J=7.6 Hz), 4.65-4.54 (1H, m), 4.39 (3H, s), 4.23-4.13 (1H, m), 4.08 (3H, s), 4.03 (3H, s), 3.69-3.57 (1H, m), 3.46-3.33 (1H, m), 2.88 (1H, d, J=16.7 Hz), 2.80 (1H, d, J=16.7 Hz), 2.28-2.19 (1H, m), 2.15-2.05 (1H, m), 2.01-1.85 (2H, m). MS [M+H]$^+$=515.

EXAMPLE 20

(5-{1'-[(4,8-dimethoxyquinolin-2-yl)carbonyl]-4-oxospiro[chroman-2,4'-piperidin]-6-yl}-2H-tetrazol-2-yl)methyl Pivalate (2-isomer) (5-{1'-[(4,8-dimethoxyquinolin-2-yl)carbonyl]-4-oxospiro[chroman-2,4'-piperidin]-6-yl}-2H-tetrazol-1-yl)methyl Pivalate (1-isomer)

2-isomer

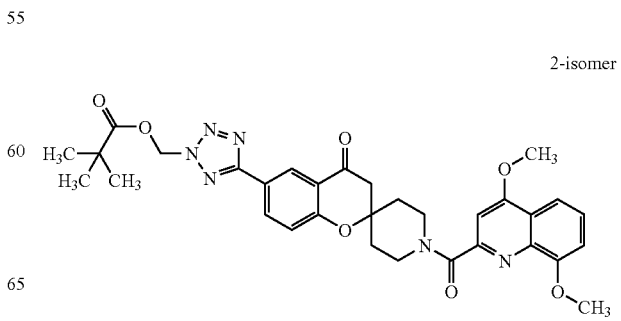

-continued 1-isomer

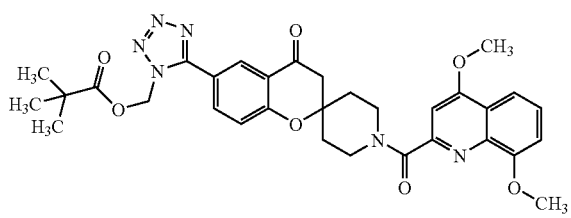

To a stirred solution of the sodium salt (105 mg) obtained in Example 18 in 1.0 mL of DMF, was added pivaloyloxymethyl chloride (35.6 μl), and the mixture was stirred at room temperature for 16 hours. The reaction mixture was diluted with 20 mL of ethyl acetate, washed with water (4 times) and aqueous saturated sodium chloride solution, then dried over sodium sulfate, and concentrated. The residue was purified through silica gel column chromatography (0.7% methanol/chloroform) to obtain the 2-isomer and 1-isomer. 2-Isomer (major product): $^1$H-NMR (CDCl$_3$) δ: 8.69 (1H, d, J=2.4 Hz), 8.32 (1H, dd, J=2.4, 8.8 Hz), 7.77 (1H, dd, J=1.0, 8.3 Hz), 7.47 (1H, dd, J=7.7, 8.3 Hz), 7.20 (1H, s), 7.16 (1H, d, J=8.8 Hz), 7.08 (1H, d, J=7.7 Hz), 6.50 (2H, s), 4.64-4.56 (1H, m), 4.24-4.17 (1H, m), 4.08 (3H, s), 4.03 (3H, s), 3.68-3.59 (1H, m), 3.40 (1H, td, J=12.9, 2.8 Hz), 2.88 (1H, d, J=16.6 Hz), 2.81 (1H, d, J=16.6 Hz), 2.28-2.20 (1H, m), 2.14-2.07 (1H, m), 2.01-1.88 (2H, m), 1.23 (9H, s). MS [M+H]$^+$=615. 1-Isomer (minor product): $^1$H-NMR (CDCl$_3$) δ: 8.30 (1H, d, J=2.4 Hz), 8.09 (1H, dd, J=8.8, 2.4 Hz), 7.78 (1H, dd, J=8.2, 1.0 Hz), 7.48 (1H, t, J=8.2 Hz), 7.25 (1H, d, J=8.2 Hz), 7.20 (1H, s), 7.08 (1H, d, J=8.8 Hz), 6.32 (1H, d, J=11.2 Hz), 6.29 (1H, d, J=11.2 Hz), 4.65-4.57 (1H, m), 4.28-4.20 (1H, m), 4.09 (3H, s), 4.04 (3H, s), 3.69-3.59 (1H, m), 3.40 (1H, td, J=12.8, 2.9 Hz), 2.90 (1H, d, J=16.6 Hz), 2.84 (1H, d, J=16.6 Hz), 2.28-2.21 (1H, m), 2.14-2.07 (1H, m), 2.06-1.89 (2H, m), 1.28 (9H, s). MS [M+H]$^+$=615.

EXAMPLE 21

1'-[(8-cyclopropyl-4-ethoxy-1,7-naphthyridin-2-yl)carbonyl]-6-(1H-tetrazol-5-yl)spiro[chroman-2,4'-piperidin]-4-one

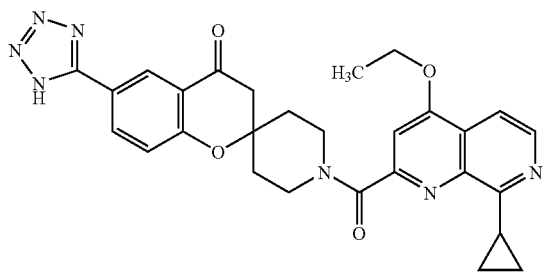

8-Cyclopropyl-4-ethoxy-1,7-naphthyridine-2-carboxylic acid (28 mg), HOBT (23 mg), WSC (32 mg) triethylamine (23 μl), DMF (0.6 mL) and water (0.2 mL) were added to the compound (45 mg) produced in Reference Example 7, and stirred at 90° C. for 30 minutes. The mixture was diluted with water at 0° C., and the resulting insoluble solid was taken out through filtration. The filter cake was suspended in and washed with methanol, and this was again taken out through filtration, and dried under reduced pressure to obtain the intended compound. $^1$H-NMR (400 MHz, DMSO-d$_6$) δ: 8.44-8.39 (2H, m), 8.24 (1H, dd, J=8.8, 2.2 Hz), 7.71 (1H, d, J=5.6 Hz), 7.37-7.33 (2H, m), 4.41-4.31 (3H, m), 3.80-3.70 (1H, m), 3.57-3.21 (3H, m), 3.01 (2H, s), 2.16-2.07 (1H, m), 2.01-1.82 (3H, m), 1.47 (3H, t, J=7.0 Hz), 1.16-1.06 (4H, m). MS [M+H]$^+$=526.

EXAMPLE 22

1'-[(4,8-dimethoxyquinolin-2-yl)carbonyl]-6-(5-oxo-4,5-dihydro-1,24-oxadiazol-3-yl)spiro[chroman-2,4'-piperidin]-4-one

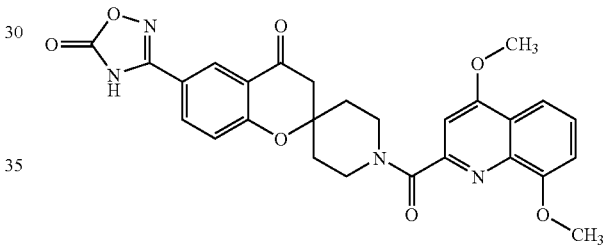

26.1 mg of hydroxylamine hydrochloride, 62.7 μl of triethylamine and 2.5 mL of EtOH were added to 1'-[(4,8-dimethoxyquinolin-2-yl)carbonyl]-4-oxospiro[chroman-2,4'-piperidine]-6-carbonitrile (115 mg) obtained in Example 16, and stirred at 60° C. for 24 hours. The reaction mixture was concentrated, and the residue was purified through silica gel column chromatography (2% MeOH/CHCl$_3$) to obtain 83.4 mg of 1'-[(4,8-dimethoxyquinolin-2-yl)carbonyl]-4-oxospiro[chroman-2,4'-piperidine]-6-carboximidamide. 49.1 mg of the product was dissolved in 1.0 mL of DMF along with 9.7 μl of pyridine therein, and 21.6 μl of 2-ethylhexyl chloroformate was added thereto at 0° C. The mixture was stirred at 0° C. for 30 minutes, then diluted with ethyl acetate (15 mL), washed with water and saturated brine, dried over sodium sulfate, and concentrated. The residue was dissolved in xylene, refluxed for 4 hours, and then concentrated, and the residue was purified through silica gel chromatography (developed with 20% MeOH/EtOAc) to obtain the intended compound. $^1$H-NMR (CDCl$_3$) δ: 8.50 (1H, d, J=2.4 Hz), 8.11 (1H, dd, J=8.8, 2.4 Hz), 7.78 (1H, dd, J=8.3, 1.0 Hz), 7.47 (1H, dd, J=8.3, 7.8 Hz), 7.21 (1H, s), 7.16 (1H, d, J=8.8 Hz), 7.07 (1H, d, J=1.0, 7.8 Hz), 4.61-4.53 (1H, m), 4.20-4.12 (1H, m), 4.10 (3H, s), 4.01 (3H, s), 3.71-3.62 (1H, m), 3.40-3.31 (1H, m), 2.95 (2H, s), 2.26-1.86 (4H, m). MS [M+H]$^+$=517.

EXAMPLE 23

1'-[(4,8-dimethoxyquinolin-2-yl)carbonyl]-6-(5-oxo-4,5-dihydro-1H-1,2,4-triazol-3-yl)spiro[chroman-2,4'-piperidin]-4-one

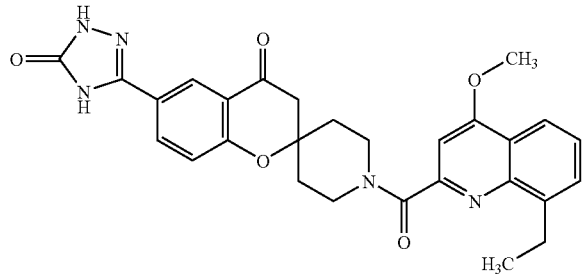

The cyano compound (22.9 mg) obtained in Example 16 was dissolved in 0.10 mL of CHCl$_3$, and 10 N HCl/EtOH (1.0 mL) was added to it, and stirred at room temperature for 22 hours. The reaction mixture was concentrated, 0.50 mL of pyridine and 4.5 mg of semicarbazide hydrochloride were added to the residue, and the mixture was stirred at 80° C. for 8 hours. The reaction mixture was concentrated, and the residue was purified through silica gel thin-layer chromatography (developed with 9% MeOH/CHCl$_3$) to obtain the intended compound. $^1$H-NMR (CDCl$_3$) δ: 10.33 (1H, br.s), 8.51 (1H, d, J=2.1 Hz), 8.30 (1H, dd, J=2.1, 8.9 Hz), 7.77 (1H, d, J=8.4 Hz), 7.47 (1H, dd, J=7.7, 8.4 Hz), 7.20 (1H, s), 7.12 (1H, d, J=8.9 Hz), 7.08 (1H, d, J=7.7 Hz), 4.66-4.55 (1H, m), 4.25-4.14 (1H, m), 4.09 (3H, s), 4.03 (3H, s), 3.68-3.55 (1H, m), 3.44-3.32 (1H, m), 2.96-2.80 (2H, m), 2.29-1.87 (4H, m). MS [M+H]$^+$=516.

EXAMPLE 24

1'-[(4,8-dimethoxyquinolin-2-yl)carbonyl]-6-(benzyloxycarbonyl)spiro-[chroman-2,4'-piperidin]-4-one

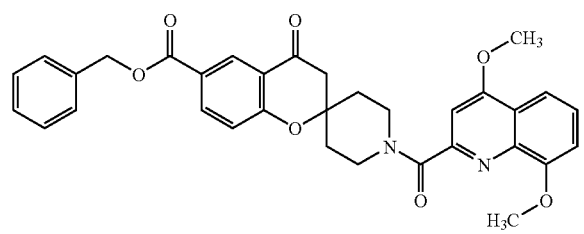

16.8 mg of palladium acetate, 83.2 mg of dppf, 0.418 mL of triethylamine, 767 mg of 1'-[(4,8-dimethoxyquinolin-2-yl)carbonyl]-6-bromospiro[chroman-2,4'-piperidin]-4-one, 0.776 mL of benzyl alcohol and 7.5 mL of DMF were stirred under a carbon monoxide atmosphere at 100° C. for 15 hours. The reaction mixture was diluted with 40 mL of ethyl acetate, and filtered through Celite. The filtrate was washed with water, dried over sodium sulfate, and concentrated. The residue was purified through silica gel chromatography (75% EtOAc/hexane) to obtain the intended compound. $^1$H-NMR (CDCl$_3$) δ: 8.60 (1H, d, J=2.2 Hz), 8.21 (1H, dd, J=8.8, 2.2 Hz), 7.77 (1H, d, J=8.3 Hz), 7.49-7.31 (6H, m), 7.19 (1H, s), 7.09-7.05 (2H, m), 5.35 (2H, s), 4.62-4.55 (1H, m), 4.24-4.16 (1H, m), 4.08 (3H, s), 4.02 (3H, s), 3.60 (1H, ddd, J=13.1, 11.8, 2.9 Hz), 3.38 (1H, td, J=13.1, 2.9 Hz), 2.85 (1H, d, J=16.6 Hz), 2.79 (1H, d, J=16.6 Hz), 2.24-2.16 (1H, m), 2.10-2.02 (1H, m), 2.00-1.86 (2H, m). MS [M+H]$^+$=567.

EXAMPLE 25

1'-[(4,8-dimethoxyquinolin-2-yl)carbonyl]-6-(carboxy)spiro[chroman-2,4'-piperidin]-4-one

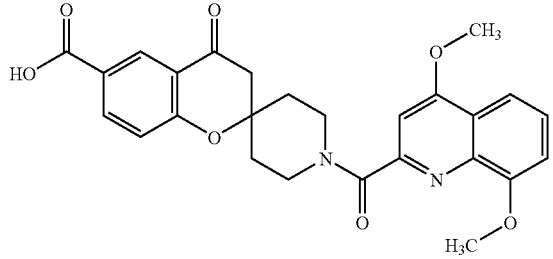

1'-[(4,8-Dimethoxyquinolin-2-yl)carbonyl]-6-(benzyloxycarbonyl)-spiro[chroman-2,4'-piperidin]-4-one (680 mg) was dissolved in 10 mL of THF and 10 mL of methanol, and vigorously stirred on 10% Pd/C under a hydrogen atmosphere for 21 hours. 1.2 mL of 1 N NaOH was added to it, and filtered through Celite, and the filtrate was concentrated. 20 mL of water was added to the residue, and extracted with ethyl acetate (3×20 mL). The aqueous layer was acidified with 1 N HCl, and extracted with ethyl acetate. The extract was washed with saturated brine, dried over sodium sulfate, and concentrated to obtain the intended compound. $^1$H-NMR (DMSO-d$_6$) δ: 8.30 (1H, d, J=2.2 Hz), 8.11 (1H, dd, J=8.7, 2.2 Hz), 7.68 (1H, dd, J=8.3, 1.2 Hz), 7.52 (1H, dd, J=8.3, 7.7 Hz), 7.23 (1H, dd, J=1.2, 7.7 Hz), 7.21 (1H, d, J=8.7 Hz), 7.18 (1H, s), 4.35-4.28 (1H, m), 4.07 (3H, s), 3.94 (3H, s), 3.69-3.62 (1H, m), 3.50-3.22 (2H, m), 2.97 (2H, s), 2.12-2.04 (1H, m), 1.96-1.80 (3H, m). MS [M+H]$^+$=477.

EXAMPLE 26

1'-[(4,8-dimethoxyquinolin-2-yl)carbonyl]-6-(5-oxo-4,5-dihydro-1,3,4-oxadiazol-2-yl)spiro[chroman-2,4'-piperidin]-4-one

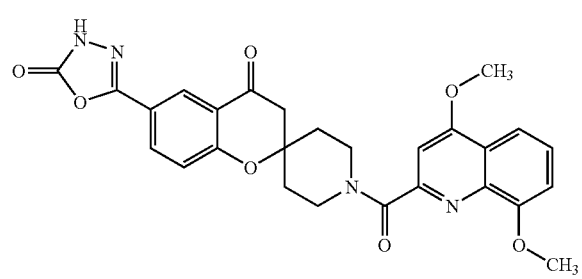

50.6 mg of EDCI was added to a mixture of 29.1 mg of Boc-hydrazine, 33.7 mg of HOBT, 105 mg of 1'-[(4,8-dimethoxyquinolin-2-yl)carbonyl]-6-(carboxy)spiro[chroman-2,4'-piperidin]-4-one and 2.2 mL of DMF, and the resulting mixture was stirred at room temperature for 14 hours. The reaction mixture was diluted with 15 mL of ethyl acetate, washed with water and aqueous saturated NaHCO$_3$ solution, and dried over sodium sulfate. The residue was purified through silica gel chromatography (2% MeOH/CHCl$_3$) to obtain 119 mg of tert-butyl 2-({1'-[(4,8-dimethoxyquinolin-2-yl)carbonyl]-4-oxospiro[chroman-2,4'-piperidin]-6-yl}carbonyl)hydrazinecarboxylate. 2 mL of 4 N HCl in dioxane was added to 59.1 mg of the product, and stirred at room temperature for 1 hour, and then concentrated. The residue was suspended in 2.5 mL of THF, and 0.049 μL of triethylamine and 24.3 mg of CDI were added thereto at 0° C., and stirred at room temperature for 14 hours. Water was added to the reaction solution, and extracted with chloroform, and the organic layer was dried over sodium sulfate and concentrated. The residue was purified through silica gel thin-layer chromatography (17% MeOH/CHCl$_3$) to obtain the intended compound. $^1$H-NMR (CDCl$_3$) δ: 8.85 (1H, br s), 8.38 (1H, d, J=2.2 Hz), 7.97 (1H, dd, J=2.2, 8.8 Hz), 7.77 (1H, dd, J=8.5, 1.0 Hz), 7.47 (1H, dd, J=7.8, 8.5 Hz), 7.20 (1H, s), 7.13 (1H, d, J=8.8 Hz), 7.08 (1H, dd, J=1.0, 7.8 Hz), 4.64-4.56 (1H, m), 4.24-4.16 (1H, m), 4.09 (3H, s), 4.03 (3H, s), 3.67-3.58 (1H, m), 3.43-3.34 (1H, m), 2.87 (1H, d, J=16.8 Hz), 2.81 (1H, d, J=16.8 Hz), 2.26-2.18 (1H, m), 2.11-2.04 (1H, m), 2.01-1.87 (2H, m). MS [M+H]$^+$=517.

EXAMPLE 27

1'-[(4,8-dimethoxyquinolin-2-yl)carbonyl]-6-(1H-1,2,4-triazol-3-yl)-spiro[chroman-2,4'-piperidin]-4-one

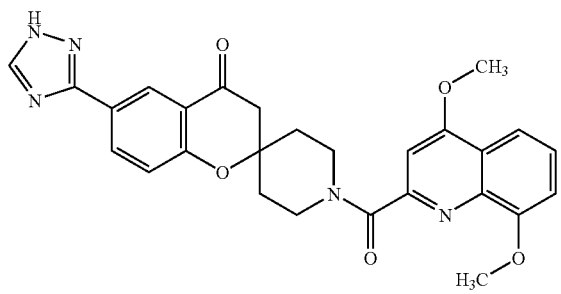

The intended compound was obtained according to the method of Example 3 but using 6-(1H-1,2,4-triazol-3-yl)spiro[chroman-2,4'-piperidin]-4-one HCl salt as the starting material. $^1$H-NMR (DMSO-d$_6$) δ: 8.41 (1H, br.s), 8.39 (1H, d, J=2.2 Hz), 8.21 (1H, dd, J=2.2, 8.5 Hz), 7.68 (1H, d, J=8.0 Hz), 7.52 (1H, t, J=8.0 Hz), 7.25 (1H, d, J=8.5 Hz), 7.24 (1H, d, J=8.0 Hz), 7.19 (1H, s), 4.37-4.26 (1H, m), 4.07 (3H, s), 3.95 (3H, s), 3.69-3.60 (1H, m), 3.52-3.37 (2H, m), 2.97 (2H, s), 2.16-2.06 (1H, m), 1.98-1.78 (3H, m). MS [M+H]$^+$=500.

EXAMPLE 28

3-{1'-[(4,8-Dimethoxyquinolin-2-yl)carbonyl]-4-oxospiro[chroman-2,4'-piperidin]-6-yl}-1H-1,2,4-triazole-5-carboxamide

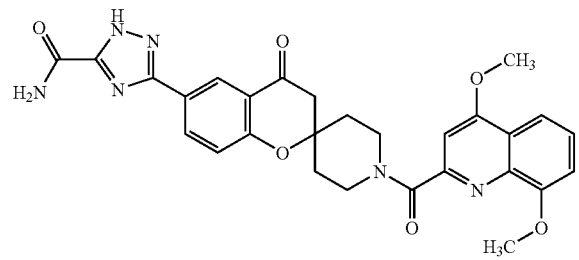

The intended compound was obtained according to the method of Example 3 but using 4-oxospiro[chroman-2,4'-piperidin]-6-yl}-1H-1,2,4-triazole-5-carboxamide as the starting material. $^1$H-NMR (300 MHz, DMSO-d$_6$) δ: 8.45 (1H, d, J=1.8 Hz), 8.23 (1H, dd, J=8.3, 1.8 Hz), 8.10 (1H, br s), 7.82 (1H, br s), 7.68 (1H, d, J=8.3 Hz), 7.52 (1H, dd, J=7.8, 8.3 Hz), 7.28 (1H, d, J=8.3 Hz), 7.24 (1H, d, J=7.8 Hz), 7.19 (1H, s), 4.37-4.29 (1H, m), 4.07 (3H, s), 3.95 (3H, s), 3.70-3.62 (1H, m), 3.52-3.23 (2H, m), 2.98 (2H, s), 2.15-2.07 (1H, m), 1.98-1.80 (3H, m). MS [M+H]$^+$=543.

EXAMPLE 29

6-(4-Carbamoylpiperazin-1-yl)-1'-[(4,8-dimethoxyquinolin-2-yl)carbonyl]-spiro[chroman-2,4'-piperidin]-4-one

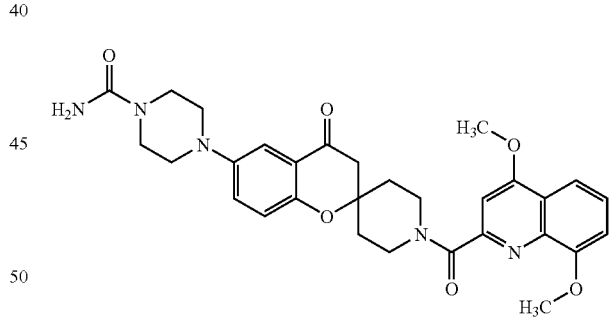

6-Bromo-1'-[(4,8-dimethoxyquinolin-2-yl)carbonyl]spiro[chroman-2,4'-piperidin]-4-one (1.00 g), 1-t-butoxycarbonylpiperazine (574 mg), palladium acetate (87.8 mg), 2-(di-t-butylphosphino)biphenyl (117 mg) and cesium carbonate (766 mg) were suspended in 1,4-dioxane (10 mL), and stirred at 110° C. for 20 hours. The reaction solution was filtered through Celite, the residue on Celite was washed with chloroform, and the filtrate was concentrated under reduced pressure. The resulting residue was subjected to silica gel column chromatography (hexane/ethyl acetate=5/5 to 0/10) to obtain a crude product of the compound, 6-(4-t-butoxycarbonylpiperazin-1-yl)-1'-[(4,8-dimethoxyquinolin-2-yl)carbonyl]spiro[chroman-2,4'-piperidin]-4-one. The resulting crude product was then dissolved in chloroform (8 mL), trifluoroacetic acid (8 mL) was added to it and stirred at room temperature for 3 hours. The reaction solution was partitioned between chloroform and aqueous 1 N sodium hydroxide solution, extracted with chloroform, and then dried with magnesium sulfate. The desiccant was removed through filtration, the filtrate was concentrated under reduced pressure, and the resulting residue was purified through thin-layer chromatography (chloroform/methanol/28% aqueous ammonia=85/15/1) to obtain 6-(piperazin-1-yl)-1'-[(4,8-dimethoxyquinolin-2-yl)carbonyl]spiro[chroman-2,4'-piperidin]-4-one. Trimethylsilyl isocyanate (100 mg, 0.870 mmol) was added to a solution of this compound (220 mg) in tetrahydrofuran (2 mL), and stirred at room temperature for 14 hours. The reaction solution was partitioned between chloroform and aqueous saturated sodium hydrogen carbonate solution, and the aqueous layer was extracted with chloroform, which was washed with saturated brine. The organic layer was dried over magnesium sulfate, the desiccant was removed through filtration, the filtrate was concentrated under a reduced pressure, and the resulting residue was purified through thin-layer chromatography (chloroform/methanol=9/1) to obtain the intended compound. $^1$H-NMR (400 MHz, CDCl$_3$) δ: 7.74 (1H, d, J=8.4 Hz), 7.44 (1H, dd, J=8.4, 7.6 Hz), 7.31 (1H, d, J=2.8 Hz), 7.17 (1H, dd, J=8.8, 2.8 Hz), 7.14 (1H, s), 7.05 (1H, d, J=7.6 Hz), 6.94 (1H, d, J=8.8 Hz), 4.72 (2H, br s), 4.50-4.60 (1H, m), 4.06 (3H, s), 4.01 (3H, s), 4.00-4.15 (1H, m), 3.50-3.65 (1H, m), 3.53 (4H, t, J=5.2 Hz), 3.30-3.40 (1H, m), 3.08 (4H, t, J=5.2 Hz), 2.77 (1H, d, J=16.4 Hz), 2.71 (1H, d, J=16.4 Hz), 2.10-2.25 (1H, m), 2.00-2.05 (1H, m), 1.75-1.90 (2H, m). MS [M+H]$^+$=560.

EXAMPLE 30

6-(4-Acetylpiperazin-1-yl)-1'-[(4,8-dimethoxyquinolin-2-yl)carbonyl]spiro[chroman-2,4'-piperidin]-4-one

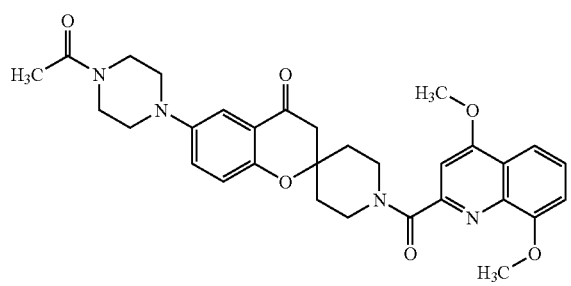

To a solution of 165 mg of 6-(piperazin-1-yl)-1'-[(4,8-dimethoxyquinolin-2-yl)carbonyl]spiro[chroman-2,4'-piperidin]-4-one in 2 mL of CHCl$_3$ was added 0.165 mL of Ac2O and 0.33 ml of triethylamine and the mixture was stirred for 4 hrs. The mixture was partitioned between CHCl3 and 1N NaOHaq, and the organic layer was separated, washed with brine, dried over MgSO$_4$, and concentrated. The residue was purified on preparative TLC (SiO$_2$, CHCl$_3$/MeOH=9/1) to afford the intended compound as a yellow powder. $^1$H-NMR (400 MHz, CDCl$_3$) δ7.74 (1H, d, J=8.4 Hz), 7.45 (1H, ddd, J=8.4, 8.0, 0.8 Hz), 7.32-7.34 (1H, m), 7.18 (1H, dd, J=8.8, 1.4 Hz), 7.16 (1H, s), 7.06 (1H, d, J=8.0 Hz), 6.95 (1H, d, J=8.8 Hz), 4.50-4.60 (1H, m), 4.00-4.20 (1H, m), 4.06 (3H, s), 4.02 (3H, s), 3.70-3.80 (2H, m), 3.50-3.70 (3H, m), 3.33-3.40 (1H, m), 3.00-3.20 (4H, m), 2.78 (1H, d, J=16.8 Hz), 2.72 (1H, d, J=16.8 Hz), 2.21-2.30 (1H, m), 2.10-2.20 (1H, m), 1.70-2.95 (2H, m). MS [M+H]$^+$=559.

EXAMPLE 31

1'-[(4,8-Dimethoxyquinolin-2-yl)carbonyl]-6-[4-(methylsulfonyl)piperazin-1-yl]spiro[chroman-2,4'-piperidin]-4-one

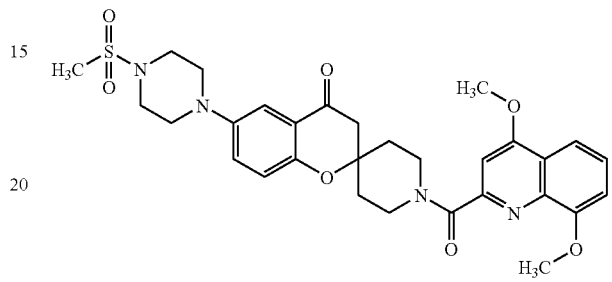

The compound was prepared according to the procedure described in Example 30, using methanesulfonyl chloride instead of Ac$_2$O. $^1$H-NMR (400 MHz, CDCl$_3$) δ7.75 (1H, d, J=8.4 Hz), 7.45 (1H, dd, J=8.4, 7.6 Hz), 7.36 (1H, d, J=1.4 Hz), 7.18 (1H, dd, J=8.4, 1.4 Hz), 7.16 (1H, s), 7.06 (1H, d, J=7.6 Hz), 6.97 (1H, d, J=8.8 Hz), 4.50-4.62 (1H, m), 4.00-4.20 (1H, m), 4.07 (3H, s), 4.02 (3H, s), 3.50-3.70 (3H, m), 3.35-3.45 (5H, m), 3.10-3.30 (4H, m), 2.82 (3H, s), 2.79 (1H, d, J=16.8 Hz), 2.73 (1H, d, J=16.8 Hz), 2.20-2.30 (1H, m), 2.10-2.20 (1H, m), 1.75-2.00 (2H, m). MS: [M+H]$^+$=595.

EXAMPLE 32

Sodium 3-{1'-[(1-cyclopropyl-5-methoxyisoquinolin-7-yl)carbonyl]-4-oxospiro[chroman-2,4'-piperidin]-6-yl}-5-oxo-1,2,4-oxadiazol-4-ide

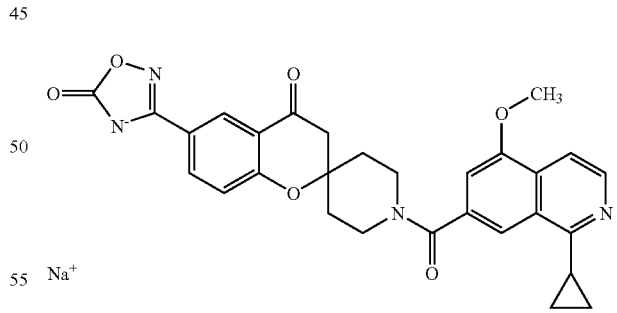

The compound was prepared according to the procedure described in the Example 1, using 1-cyclopropyl-4-methoxyisoquinoline-7-carboxylic acid instead of 4,8-dimethoxyquinoline-2-carboxylic acid, and 3-[4-oxospiro(chroman-2,4'-piperidin)-6-yl]-5-oxo-1,2,4-oxadiazole instead of 4-oxospiro(chroman-2,4'-piperidin)-6-yl acetamide. Na salt $^1$H-NMR (400 MHz, DMSO-d$_6$) δ: 8.35 (1H, d, J=5.9 Hz), 8.13-8.11 (1H, m), 8.06 (1H, br s), 7.95 (1H, dd, J=8.5, 2.2 Hz), 7.73 (1H, d, J=5.9 Hz), 7.18 (1H, br s), 7.09 (1H, d, J=8.5

Hz), 4.31 (1H, br s), 4.00 (3H, s), 3.50 (1H, br s), 3.36-3.26 (2H, m), 2.95-2.86 (3H, m), 2.12-1.77 (4H, m), 1.14-1.04 (4H, m). MS [M+H]+=527.

EXAMPLE 33

1'-[4-(2-Hydroxyethoxy)-8-methoxy-2-naphthoyl]-6-(5-oxo-4,5-dihydro-1,2,4-oxadiazol-3-yl)spiro[chroman-2,4'-piperidin]-4-one

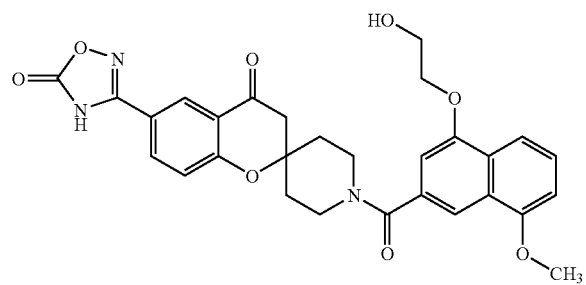

The compound was prepared according to the procedure described in the Example 1, using 4-(2-hydroxyethoxy)-8-methoxy-2-naphthoic acid instead of 4,8-dimethoxyquinoline-2-carboxylic acid, and 3-[4-oxospiro(chroman-2,4'-piperidin)-6-yl]-5-oxo-1,2,4-oxadiazole instead of 4-oxospiro(chroman-2,4'-piperidin)-6-yl acetamide. $^1$H-NMR (400 MHz, DMSO-$d_6$) δ; 8.24 (1H, d, J=4.0 Hz), 8.04 (1H, dd, J=4.0, 8.0 Hz), 7.86 (1H, d, J=8.0 Hz), 7.75 (1H, s), 7.51 (1H, t, J=8.0 Hz), 7.34 (1H, d, J=8 Hz), 7.09 (1H, d, J=8 Hz), 7.00 (1H, s), 4.40-4.22 (1H, m), 4.20 (2H, t, J=4.0 Hz), 4.01 (3H, s), 3.92-3.89 (2H, m), 3.75-3.30 (3H; m), 3.03 (2H, s), 2.12-1.75 (4H, m). MS [M+H]+=546.

EXAMPLE 34

1'-[8-Methoxy-4-(1H-tetrazol-5-yl)-2-naphthoyl]-6-(1-methyl-1H-pyrazol-4-yl)spiro[chroman-2,4'-piperidin]-4-one

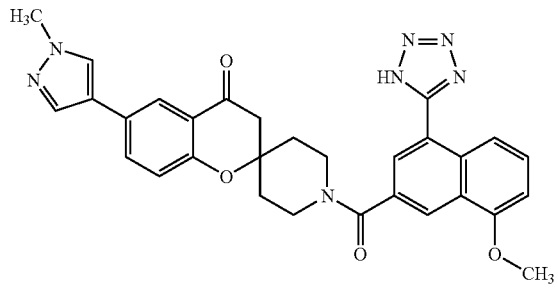

The compound is synthesized according to the procedure described in Example 1, using 6-(1-methyl-1H-pyrazol-4-yl)spiro[chroman-2,4'-piperidin]-4-one instead of 4-oxospiro(chroman-2,4'-piperidin)-6-yl acetamide, and 8-methoxy-4-(1H-tetrazol-5-yl)-2-naphthoic acid instead of 4,8-dimethoxyquinoline-2-carboxylic acid. $^1$H-NMR (400 MHz, DMSO-$d_6$) δ: 8.39 (1H, s), 8.21 (1H, d, J=8.0 Hz), 8.12 (1H, s), 8.01 (1H, d, J=2.0 Hz), 7.83-7.77 (3H, m), 7.63 (1H, t, J=8 Hz), 7.15 (1H, d, J=8 Hz), 7.11 (1H, d, J=8.0 Hz), 4.40-4.22 (1H, m), 4.02 (3H, s), 3.83 (3H, s), 3.70-3.30 (3H, m), 2.89 (2H, s), 2.12-1.75 (4H, m). MS [M+H]+=550.

EXAMPLE 35

3-{1'-[(8-Cyclopropyl-4-methoxyquinolin-2-yl)carbonyl]-4-oxospiro[chroman-2,4'-piperidin]-6-yl}-1H-1,2,4-triazole-5-carboxamide

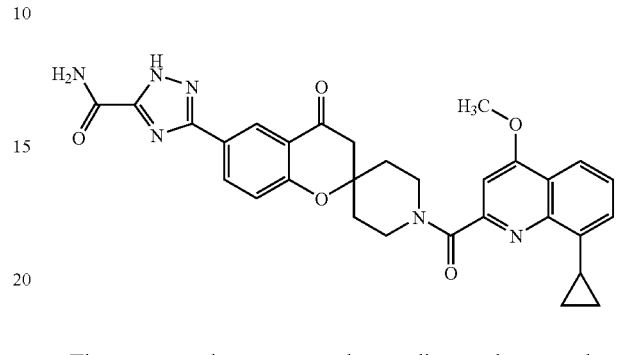

The compound was prepared according to the procedure described in Example 28, using 8-cyclopropyl-4-methoxyquinoline-2-carboxylic acid instead of 4,8-dimethoxyquinoline-2-carboxylic acid. $^1$H-NMR (400 MHz, DMSO-$d_6$) δ: 8.43 (1H, d, J=4.0 Hz), 8.21 (1H, dd, J=4.0, 8.0 Hz), 7.94 (1H, dd, J=2.0, 8.0 Hz), 7.51-7.47 (1H, m), 7.28-7.24 (2H, m), 7.20 (1H, s), 4.37-4.32 (1H, m), 4.07 (3H, s), 3.92-3.85 (1H, m), 3.56-3.46 (1H, m), 3.37-3.27 (1H, m), 3.09-3.05 (1H, m), 2.98 (2H, s), 2.16-1.83 (4H, m), 1.08-1.06 (2H, m), 0.85-0.74 (2H, m). MS [M+H]+=553 (ESI).

EXAMPLE 36

5-{1'-[(8-Cyclopropyl-4-methoxyquinolin-2-yl)carbonyl]-4-oxospiro[chroman-2,4'-piperidin]-6-yl}nicotinic acid

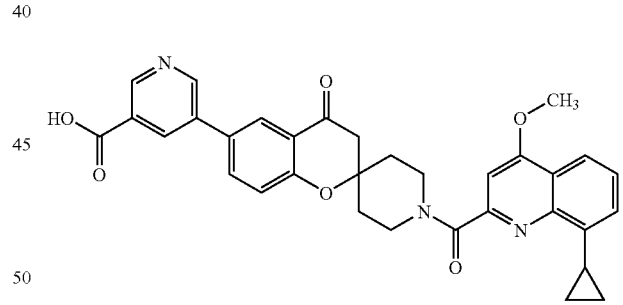

5-{4-oxospiro[chroman-2,4'-piperidin]-6-yl}nicotinic acid di-hydrochloride (4.93 g, 12.0 mmol), TEA (5.14 mL, 36.9 mmol) were suspended in DMF (49 mL) and (8-cyclopropyl-4-methoxy-quinolin-2-yl)-imidazol-1-yl-methanone (2.70 g, 9.22 mmol) was added thereto at room temperature, and the reaction mixture was stirred at 70° C. for 19 h. After cooled to room temperature, the mixture was poured into 1N HCl aq. (27.7 mL, 27.7 mmol) in H$_2$O (367 mL) solution and the suspension was stirred for 2 h. The resulting precipitate was filtered, washed with H$_2$O to give crude intended compound as a pale brown solid. This solid was washed with EtOAc-MeOH (1:1), then EtOH, and dried to afford the intended compound as a colorless solid. $^1$H-NMR (400 MHz, DMSO-$d_6$) δ: 9.08 (1.0H, d, J=2.4 Hz), 9.03 (1.0H, d, J=2.0 Hz), 8.41 (1.0H, dd, J=2.0, 2.4 Hz), 8.07-8.03 (2.0H, m), 7.94

(1.0H, dd, J=8.3, 1.5 Hz), 7.49 (1.0H, dd, J=8.3, 7.6 Hz), 7.30-7.23 (2.0H, m), 7.20 (1.0H, s), 4.40-4.33 (1.0H, m), 4.07 (3.0H, s), 3.94-3.87 (1.0H, m), 3.57-3.48 (1.0H, m), 3.39-3.24 (1.0H, m), 3.11-3.04 (1.0H, m), 2.98 (2.0H, s), 2.15-2.07 (1.0H, m), 2.03-1.79 (3.0H, m), 1.10-1.04 (2.0H, m), 0.87-0.72 (2.0H, m). MS [M+H]+=564.

EXAMPLE 37

N-(2-Amino-2-oxoethyl)-1'-{[1-cyclopropyl-5-(2-hydroxyethoxy)isoquinolin-7-yl]carbonyl}-4-oxospiro[chroman-2,4'-piperidine]-6-carboxamide

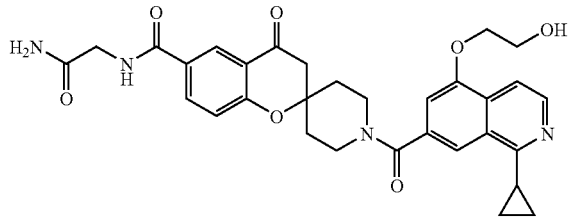

The intended compound was produced according to the procedure described in reference Example 37 but using 4-oxospiro(chroman-2,4'-piperidin)-6-yl-carboxylicacidcarbamoylmethyl amide hydrochloride and 1-cyclopropyl-5-(2-hydroxy-ethoxy)-isoquinoline-7-carboxylic acid in place of methyl 5"-{4-oxospiro[chroman-2,4'-piperidin]-6-yl}nicotinate di-hydrochloride and 1-cyclopropyl-5-methoxy-isoquinoline-7-carboxylic acid. $^1$H-NMR (400 MHz, DMSO-$d_6$) δ: 8.75 (1.0H, t, J=5.7 Hz), 8.36 (1.0H, d, J=5.7 Hz), 8.31 (1.0H, d, J=2.4 Hz), 8.09 (1.0H, dd, J=8.8, 2.4 Hz), 8.05 (1.0H, s), 7.85 (1.0H, d, J=5.9 Hz), 7.34 (1.0H, s), 7.22-7.14 (2.0H, m), 6.99 (1.0H, s), 5.00 (1.0H, t, J=5.7 Hz), 4.39-4.25 (1.0H, m), 4.21 (2.0H, t, J=4.8 Hz), 3.84 (2.0H, q, J=4.8 Hz), 3.78 (2.0H, d, J=5.9 Hz), 3.62-3.17 (3.0H, m), 2.95 (2.0H, s), 2.93-2.85 (1.0H, m), 2.15-1.77 (4.0H, m), 1.15-0.99 (4.0H, m). MS [M]+572.

EXAMPLE 38

5-(1'-{[8-Cyclopropyl-4-(2-hydroxyethoxy)-1,7-naphthyridin-2-yl]carbonyl}-4-oxospiro[chroman-2,4'-piperidin]-6-yl)nicotinamide

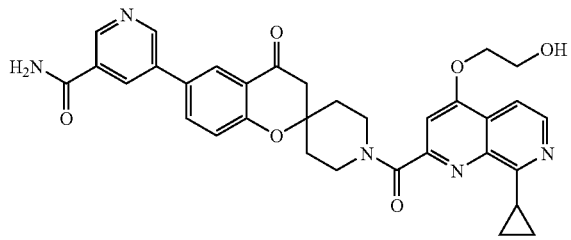

The intended compound was produced according to the procedure described in reference Example 37 but using 5-{4-oxospiro[chroman-2,4'-piperidin]-6-yl}nicotinamide di-hydrochloride and 8-cyclopropyl-4-(2-hydroxy-ethoxy)-[1,7]naphthyridine-2-carboxylic acid in place of methyl 5-{4-oxospiro[chroman-2,4'-piperidin]-6-yl}nicotinate di-hydrochloride and 1-cyclopropyl-5-methoxyisoquinoline-7-carboxylic acid. $^1$H-NMR (400 MHz, DMSO-$d_6$) δ: 8.99 (2.0H, dd, J=10.6, 2.1 Hz), 8.48-8.45 (1.0H, m), 8.42 (1.0H, d, J=5.6 Hz), 8.28 (1.0H, br s), 8.11 (1.0H, d, J=2.4 Hz), 8.06 (1.0H, dd, J=8.5, 2.4 Hz), 7.81 (1.0H, d, J=5.6 Hz), 7.64 (1.0H, br s), 7.38 (1.0H, s), 7.29 (1.0H, d, J=8.5 Hz), 5.06 (1.0H, t, J=5.6 Hz), 4.39-4.30 (3.0H, m), 3.90-3.81 (2.0H, m), 3.80-3.70 (1.0H, m), 3.58-3.39 (2.0H, m), 3.37-3.27 (1.0H, m), 2.98 (2.0H, s), 2.17-2.06 (1.0H, m), 2.02-1.80 (3.0H, m), 1.19-1.02 (4.0H, m). MS [M+H]+=594.

EXAMPLE 39

5-{1'-[(1-Cyclopropyl-5-methoxyisoquinolin-7-yl)carbonyl]-4-oxospiro[chroman-2,4'-piperidin]-6-yl}nicotinic Acid Sodium Salt

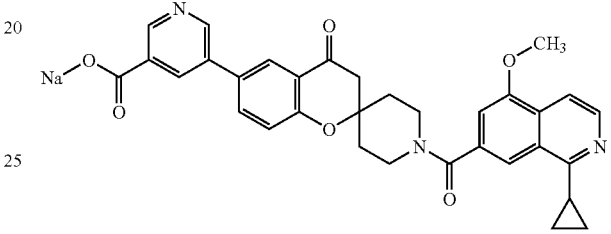

5-{1'-[(1-Cyclopropyl-5-methoxy-isoquinolin-7-yl)carbonyl]-4-oxospiro[chroman-2,4'-piperidin]-6-yl}nicotinic acid methyl ester (1.80 g, 3.11 mmol) was suspended in MeOH (18 mL) and THF (9 mL), and 1N NaOH (9.34 mL) was added thereto. After stirred at room temperature for 5 h, 1N HCl aq. (6.23 mL) was added to the reaction mixture and the solvents was removed in vacuo. The residue was purified by ODS column chromatography (H$_2$O/MeOH=100/0 to 60/40) to obtain the intended compound as a colorless solid. $^1$H-NMR (400 MHz, DMSO-$d_6$) δ: 8.92 (1H, d, J=1.7 Hz), 8.76 (1H, d, J=2.4 Hz), 8.36 (1H, d, J=5.6 Hz), 8.31-8.28 (1H, m), 8.08 (1H, s), 8.00-7.96 (2H, m), 7.74 (1H, d, J=5.6 Hz), 7.23 (1H, d, J=9.3 Hz), 7.19 (1H, s), 4.41-4.26 (1H, br m), 4.01 (3H, s), 3.60-3.46 (1H, br m), 3.39-3.27 (2H, br m), 2.97-2.87 (1H, m), 2.95 (2H, s), 2.19-2.02 (1H, br m), 2.02-1.72 (3H, m), 1.15-1.04 (4H, m). ESI-MS [M+Na]+=586.

EXAMPLE 40

3-{1'-[(1-cyclopropyl-5-methoxyisoquinolin-7-yl)carbonyl]-4-oxospiro[chroman-2,4'-piperidin]-6-yl}benzoic acid

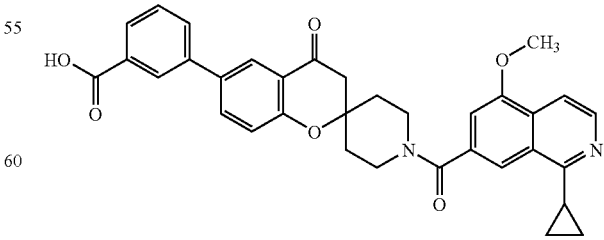

3-{1'-[(1-Cyclopropyl-5-methoxy-isoquinolin-7-yl)carbonyl]-4-oxospiro[chroman-2,4'-piperidin]-6-yl}benzoic acid methyl ester (2.00 g, 3.47 mmol) was dissolved in MeOH (20 mL), THF (10 mL) and 1N NaOH aq. (6 mL) was added thereto. After stirred at room temperature for 3 days, the reaction mixture was diluted with CHCl₃, MeOH and 1N HCl aq. (6 mL). The aqueous layer was extracted with CHCl₃ and the combined organic layer was dried over MgSO₄. The desiccant was removed through filtration and the filtrate was concentrated under reduced pressure. The residue was purified by silica gel column chromatography (hexane/EtOAc=5/5 to 0/10, then CHCl₃/MeOH=10/0 to 88/12) to obtain the intended compound as a colorless solid. ¹H-NMR (400 MHz, DMSO-d₆) δ: 8.36 (1.0H, d, J=5.9 Hz), 8.13 (1.0H, s), 8.07 (1.0H, s), 7.99-7.94 (2.0H, m), 7.93-7.85 (2.0H, m), 7.74 (1.0H, d, J=5.9 Hz), 7.60-7.53 (1.0H, m), 7.23 (1.0H, d, J=9.0 Hz), 7.19 (1.0H, s), 4.43-4.25 (1.0H, br m), 4.01 (3.0H, s), 3.67-3.13 (3.0H, m), 2.98-2.87 (1.0H, m), 2.95 (2.0H, s), 2.18-2.05 (1.0H, br m), 2.00-1.78 (3.0H, m), 1.16-1.01 (4.0H, m). MS [M+H]+=563.

EXAMPLE 41

1'-(4,8-Dimethoxy-2-naphthoyl)-6-(1H-tetrazol-5-yl)spiro[chroman-2,4'-piperidin]-4-one

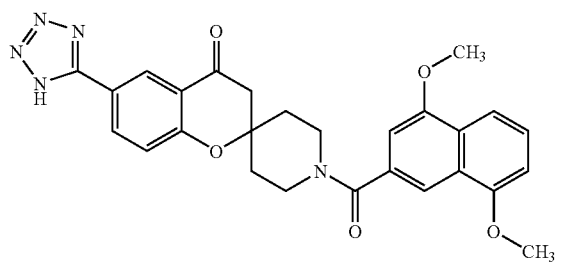

The compound was synthesized according to the procedure described in Example 21, using 4,8-dimethoxy-2-naphthoic acid instead of 8-cyclopropyl-4-ethoxy-1,7-naphthyridine-2-carboxylic acid. ¹H-NMR (400 MHz, DMSO-d₆) δ: 8.41 (1H, d, J=2.2 Hz), 8.23 (1H, dd, J=8.8, 2.2 Hz), 7.71 (1H, br s), 7.70 (1H, d, J=8.0 Hz), 7.46 (1H, t, J=8.0 Hz), 7.34 (1H, d, J=8.8 Hz), 7.05 (1H, d, J=8.0 Hz), 6.96 (1H, br s), 4.39-4.19 (1H, m), 3.98 (3H, s), 3.96 (3H, s), 3.63-3.20 (3H, m), 2.99 (2H, s), 2.13-1.73 (4H, m). MS [M+H]+=500.

EXAMPLE 42

1'-(8-Methoxy-4-morpholin-4-yl-2-naphthoyl)-6-(1H-tetrazol-5-yl)spiro[chroman-2,4'-piperidin]-4-one

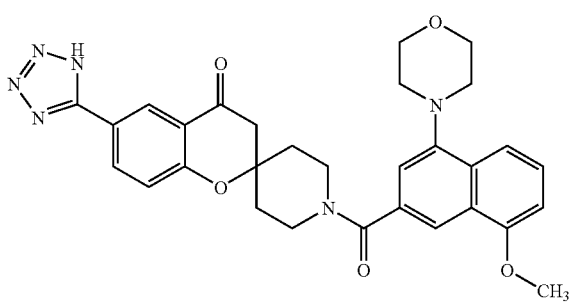

The compound was synthesized according to the procedure described in Example 21, using 4-morpholino-8-methoxy-2-naphthoic acid instead of 8-cyclopropyl-4-ethoxy-1,7-naphthyridine-2-carboxylic acid. ¹H-NMR (400 MHz, DMSO-d₆) δ: 8.42 (1H, d, J=2.4 Hz), 8.24 (1H, dd, J=8.7 Hz, 2.4 Hz), 7.89 (1H, s), 7.71 (1H, d, J=8.7 Hz), 7.49 (1H, t, J=8.3 Hz), 7.36 (1H, d, J=8.3 Hz), 7.11 (1H, d, J=1.5 Hz), 7.02 (1H, d, J=8.3 Hz), 4.33-4.31 (1H, m), 3.96 (3H, s), 3.85 (4H, s), 3.47-3.37 (4H, m), 3.03-2.99 (6H, m), 2.01-1.81 (4H, m). MS [M−H]−=553.

EXAMPLE 43

1'-[(8-Methoxy-4-phenylquinolin-2-yl)carbonyl]-6-(1H-tetrazol-5-yl)spiro[chroman-2,4'-piperidin]-4-one

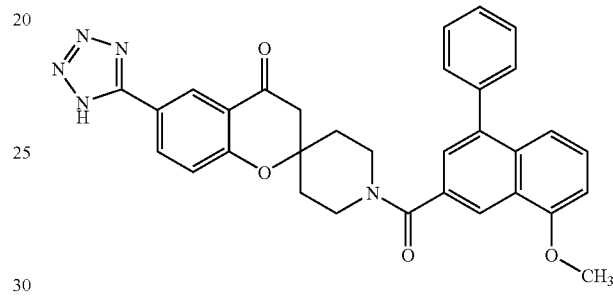

The compound was synthesized according to the procedure described in Example 21, using 4-phenyl-8-methoxy-2-quinolinecarboxylic acid instead of 8-cyclopropyl-4-ethoxy-1,7-naphthyridine-2-carboxylic acid. ¹H-NMR (400 MHz, DMSO-d₆) δ: 8.42 (1H, d, J=2.0 Hz), 8.24 (1H, dd, J=9.0, 2.0 Hz), 7.59-7.54 (7H, m), 7.39 (1H, d, J=9.0 Hz), 7.35 (1H, d, J=9.0 Hz), 7.28 (1H, d, J=8.0 Hz), 4.35 (1H, d, J=12.0 Hz), 3.99 (3H, s), 3.78 (1H, d, J=12.0 Hz), 3.53 (1H, t, J=12.0 Hz), 3.38-3.27 (1H, m), 3.00 (2H, s), 2.10 (1H, d, J=13.2 Hz), 2.00-1.82 (3H, m). MS [M+H]+=547.

EXAMPLE 44

1'-[(8-Cyclopropyl-4-methoxyquinolin-2-yl)carbonyl]-6-(1H-tetrazol-5-yl)spiro[chroman-2,4'-piperidin]-4-one

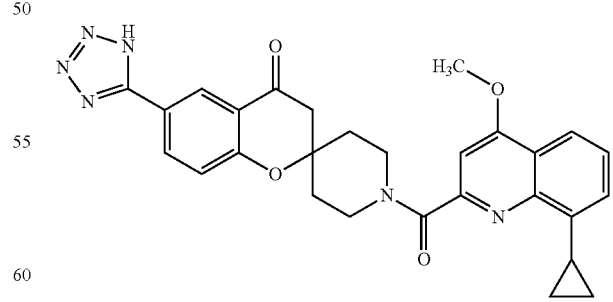

The compound was synthesized according to the procedure described in Example 21, using 8-cyclopropyl-4-methoxyquinoline-2-carboxylic acid instead of 8-cyclopropyl-4-ethoxy-1,7-naphthyridine-2-carboxylic acid. ¹H-NMR (400 MHz, DMSO-d₆) δ: 8.42 (1H, d, J=2.0 Hz), 8.24 (1H, dd, J=8.5 Hz, 2.0 Hz), 7.94 (1H, d, J=8.0 Hz), 7.49 (1H, t, J=8.0 Hz), 7.36 (1H, d, J=8.5 Hz), 7.25 (1H, d, J=7.3 Hz), 7.20 (1H, s), 4.37-4.34 (1H, m), 4.07 (3H, s), 3.91-3.88 (1H, m), 3.53-3.50 (1H, m), 3.07-3.01 (3H, m), 2.12-2.09 (1H, m), 2.00-1.85 (3H, m), 1.08-1.05 (2H, m), 0.81-0.78 (2H, m). MS [M−H]−=509.

EXAMPLE 45

1'-[(4-Ethoxy-8-ethylquinolin-2-yl)carbonyl]-6-(1H-tetrazol-5-yl)spiro[chroman-2,4'-piperidin]-4-one

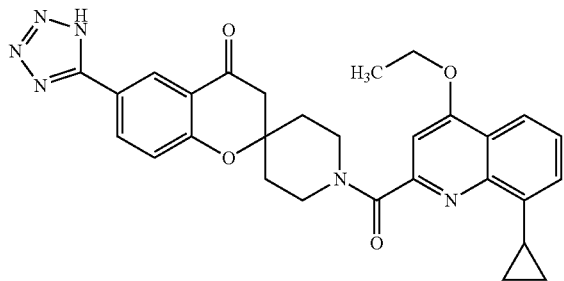

The compound was prepared according to the procedure described in Example 21, using 8-cyclopropyl-4-ethoxyquinoline-2-carboxylic acid instead of 8-cyclopropyl-4-ethoxy-1,7-naphthyridine-2-carboxylic acid. $^1$H-NMR (400 MHz, DMSO-d$_6$) δ: 8.42 (1H, d, J=2.1 Hz), 8.23 (1H, dd, J=8.4 Hz, 2.1 Hz), 7.95 (1H, dd, J=8.4 Hz, 2.6 Hz), 7.48 (1H, t, J=8.3 Hz), 7.35 (1H, d, J=8.3 Hz), 7.24 (1H, d, J=2.3 Hz), 7.17 (1H, s), 4.35-4.33 (3H, m), 3.89-3.85 (1H, m), 3.52-3.49 (1H, m), 3.32-3.30 (1H, m), 3.09-3.05 (1H, m), 2.12-2.09 (1H, m), 1.98-1.87 (3H, m), 1.48 (3H, t, J=7.1 Hz), 1.07 (2H, dd, J=8.0 Hz, 2.7 Hz), 0.85-0.76 (2H, m). MS [M−H]−=523.

EXAMPLE 46

1'-[(4-Ethoxy-8-ethylquinolin-2-yl)carbonyl]-6-(1H-tetrazol-5-yl)spiro[chroman-2,4'-piperidin]-4-one

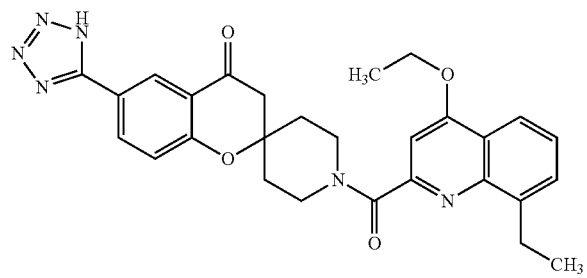

The compound was prepared according to the procedure described in Example 21, using 4-ethoxy-8-ethylquinoline-2-carboxylic acid instead of 8-cyclopropyl-4-ethoxy-1,7-naphthyridine-2-carboxylic acid. $^1$H-NMR (400 MHz, DMSO-d$_6$) δ: 8.42 (1H, d, J=1.8 Hz), 8.23 (1H, dd, J=8.8 Hz, 1.8 Hz), 8.01 (1H, d, J=8.8 Hz), 7.63 (1H, d, J=8.3 Hz), 7.52 (1H, t, J=8.3 Hz), 7.36 (1H, d, J=8.3 Hz), 7.15 (1H, s), 4.36-4.31 (3H, m), 3.88-3.84 (1H, m), 3.53-3.47 (1H, m), 3.36-3.30 (2H, m), 3.21-3.10 (2H, m), 2.12-2.08 (1H, m), 2.00-1.85 (3H, m), 1.48 (3H, t, J=7.1 Hz), 1.25 (3H, t, J=7.8 Hz). MS [M−H]−=511.

EXAMPLE 47

1'-[(5,8-Dichloro-4-ethoxyquinolin-2-yl)carbonyl]-6-(1H-tetrazol-5-yl)spiro[chroman-2,4'-piperidin]-4-one

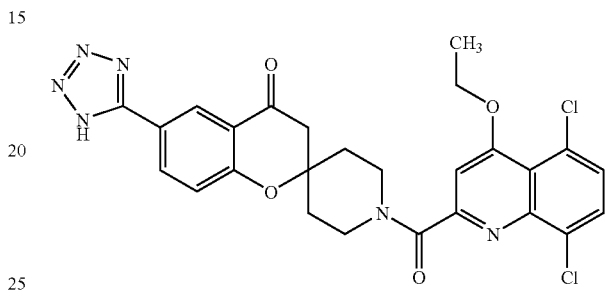

The compound was prepared according to the procedure described in Example 21, using 5,8-dichloro-4-ethoxyquinoline-2-carboxylic acid instead of 8-cyclopropyl-4-ethoxy-1,7-naphthyridine-2-carboxylic acid. $^1$H-NMR (400 MHz, DMSO-d$_6$): 8.42 (1H, d, J=2.5 Hz), 8.36 (1H, dd. J=8.8 Hz, 2.5 Hz), 7.91 (1H, d, J=8.3 Hz), 7.63 (1H, d, J=8.3 Hz), 7.36 (1H, d, J=8.8 Hz), 4.40-4.30 (3H, m), 3.85-3.75 (1H, m), 3.55-3.25 (2H, m), 3.01 (2H, s), 2.15-1.85 (4H, m), 1.48 (3H, t, J=6.8 Hz). MS [M+H]+=553.

EXAMPLE 48

1'-[(1,5-Dimethoxyisoquinolin-7-yl)carbonyl]-6-(1H-tetrazol-5-yl)spiro[chroman-2,4'-peridin]-4-one

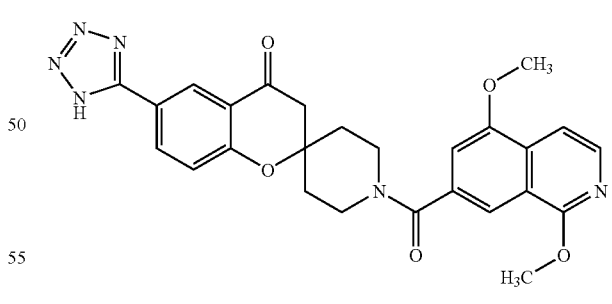

The compound was prepared according to the procedure described in Example 21, using 1,5-dimethoxyisoquinoline-7-carboxylic acid instead of 8-cyclopropyl-4-ethoxy-1,7-naphthyridine-2-carboxylic acid. $^1$H-NMR (400 MHz, DMSO-d$_6$) δ: 8.42 (1H, d, J=2.0 Hz), 8.24 (1H, dd, J=8.0, 2.0 Hz), 8.05 (1H, d, J=6.0 Hz), 7.72 (1H, s), 7.51 (1H, d, J=6.0 Hz), 7.33 (1H, d, J=8.0 Hz), 7.20 (1H, s), 5.00 (1H, br s), 4.32 (1H, br s), 4.05 (3H, s), 4.00 (3H, s), 3.58-3.21 (3H, m), 2.99 (2H, s), 2.15-1.80 (4H, m). MS [M+H]+=501.

EXAMPLE 49

1'-[(1-Cyclopropyl-5-ethoxyisoquinolin-7-ethoxyisoquinolin-7-yl)carbonyl]-6-(1H-tetrazol-5-yl)spiro[chroman-2,4'-piperidin]-4-one

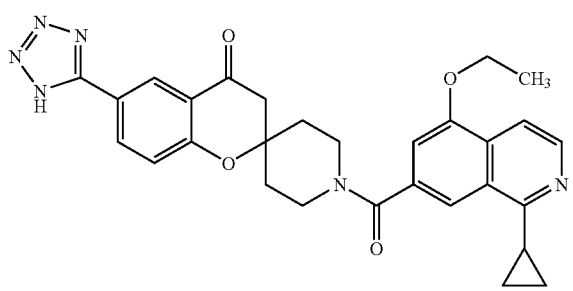

The compound was prepared according to the procedure described in Example 21, using 1-cyclopropyl-5-ethoxyisoquinoline-7-carboxylic acid instead of 8-cyclopropyl-4-ethoxy-1,7-naphthyridine-2-carboxylic acid. $^1$H-NMR (400 MHz, DMSO-$d_6$) δ: 8.43-8.40 (1H, m), 8.35 (1H, dd, J=6.0, 2.0 Hz), 8.24 (1H, dd, J=8.8, 2.0 Hz), 8.05 (1H, br s), 7.75 (1H, d, J=6.0 Hz), 7.33 (1H, dd, J=8.8, 2.0 Hz), 7.16 (1H, br s), 4.32 (1H, br s), 4.26 (2H, q, J=6.8 Hz), 3.59-3.19 (3H, m), 2.99 (2H, s), 2.94-2.86 (1H, m), 2.14-1.80 (4H, m), 1.46 (3H, t, J=6.8 Hz), 1.13-1.03 (4H, m). MS [M+H]+=525.

EXAMPLE 50

Sodium 5-{1'-[(1-cyclopropyl-5-ethoxyisoquinolin-7-yl)carbonyl]-4-oxospiro[chroman-2,4'-piperidin]-6-yl}tetrazol-1-ide

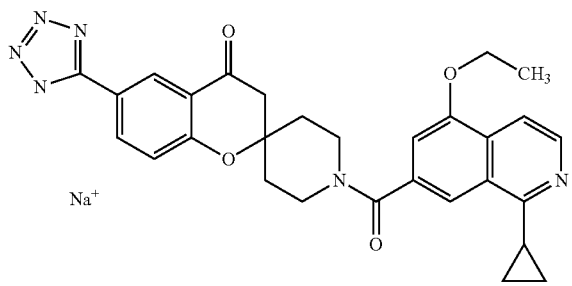

The compound of Example 49 was converted to its salt according to the procedure described in Example 18. $^1$H-NMR (DMSO-$d_6$) δ: 8.38 (1H, d, J=5.6 Hz), 8.34 (1H, d, J=2.2 Hz), 8.19 (1H, dd, J=8.5 Hz, 2.2 Hz), 8.08 (1H, s), 7.77 (1H, d, J=5.6 Hz), 7.20 (1H, s), 7.13 (1H, d, J=8.5 Hz), 4.40-4.29 (3H, m), 3.61-3.27 (4H, m), 2.93 (2H, s), 2.18-1.78 (4H, m), 1.49 (3H, t, J=7.0 Hz), 1.18-1.05 (4H, m). ESI-MS Found: m/z: 525 [M+H]+.

EXAMPLE 51

1'-{[1-Cyclopropyl-5-(2-hydroxyethoxy)isoquinolin-7-yl]carbonyl}-6-(1H-tetrazol-5-yl)spiro[chroman-2,4'-piperidin]-4-one

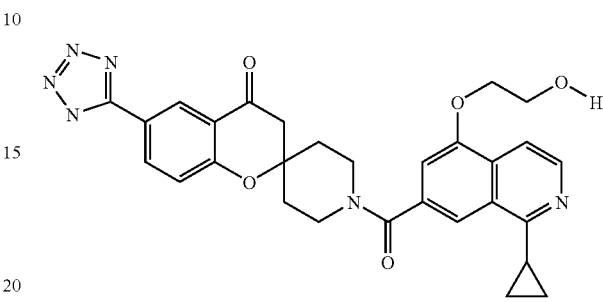

The compound was prepared according to the procedure described in Example 21, using 1-cyclopropyl-5-(2-hydroxyethoxy)isoquinoline-7-carboxylic acid instead of 8-cyclopropyl-4-ethoxy-1,7-naphthyridine-2-carboxylic acid. $^1$H-NMR (400 MHz, DMSO-$d_6$) δ: 8.42 (1H, d, J=2.0 Hz), 8.36 (1H, d, J=6.0 Hz), 8.24 (1H, dd, J=8.8, 2.0 Hz), 8.05 (1H, s), 7.85 (1H, d, J=6.0 Hz), 7.33 (1H, d, J=8.8 Hz), 7.18 (1H, s), 5.00 (1H, br s), 4.32 (1H, br s), 4.24-4.18 (2H, m), 3.88-3.80 (2H, m), 3.58-3.21 (3H, m), 2.99 (2H, s), 2.90 (1H, br s), 2.15-1.80 (4H, m), 1.15-1.03 (4H, m). MS [M+H]+=541.

EXAMPLE 52

1'-[(4-Cyclopropyl-8-ethoxyisoquinolin-6-yl)carbonyl]-6-(1H-tetrazol-5-yl)spiro[chroman-2,4'-piperidin]-4-one

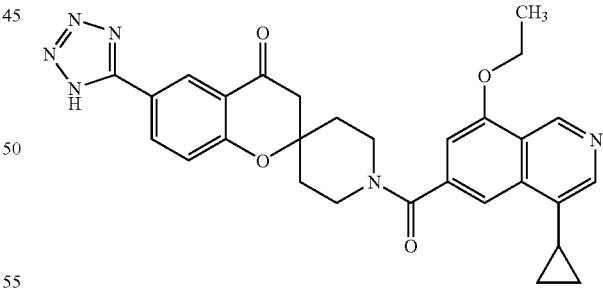

The compound was prepared according to the procedure described in Example 21, using 4-cyclopropyl-8-ethoxyisoquinolin-6-carboxylic acid instead of 8-cyclopropyl-4-ethoxy-1,7-naphthyridine-2-carboxylic acid. $^1$H-NMR (400 MHz, DMSO-$d_6$) δ: 9.37 (1H, s), 8.42 (1H, d, J=2.2 Hz), 8.32 (1H, s), 8.23 (1H, dd, J=8.8 Hz, 2.2 Hz), 7.84 (1H, s), 7.33 (1H, d, J=8.8 Hz), 7.09 (1H, s), 4.4-4.2 (3H, m), 3.6-3.1 (3H, m), 3.00 (2H, s), 2.35-2.25 (1H, m), 2.15-1.80 (4H, m), 1.47 (3H, t, J=6.83 Hz), 1.10-1.00 (2H, m), 0.80-0.70 (2H, m). MS [M+H]+=525.

EXAMPLE 53

1'-[(4-Cyclopropyl-8-methoxyquinolin-6-yl)carbonyl]-6-(1H-tetrazol-5-yl)spiro[chroman-2,4'-piperidin]-4-one

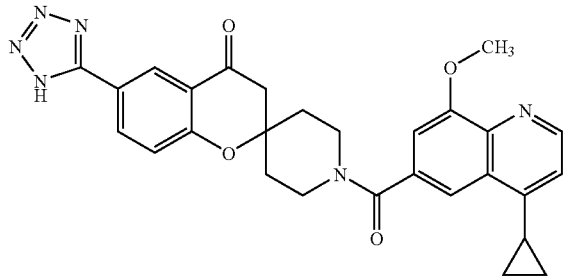

The compound was prepared according to the procedure described in Example 21, using 4-cyclopropyl-8-methoxyquinoline-6-carboxylic acid instead of 8-cyclopropyl-4-ethoxy-1,7-naphthyridine-2-carboxylic acid. $^1$H-NMR (400 MHz, DMSO-$d_6$) δ: 8.72 (1H, d, J=4.6 Hz), 8.42 (1H, d, J=2.3 Hz), 8.24 (1H, dd, J=8.7, 2.3 Hz), 7.94 (1H, d, J=1.2 Hz), 7.34 (1H, d, J=8.7 Hz), 7.19 (1H, d, J=4.6 Hz), 7.17 (1H, d, J=1.2 Hz), 4.33 (1H, br s), 3.97 (3H, s), 3.65-3.16 (3H, m), 3.00 (2H, s), 2.57-2.45 (1H, m), 2.16-1.79 (4H, m), 1.18-1.12 (2H, m), 0.89-0.81 (2H, m). MS [M+H]+=511.

EXAMPLE 54

Sodium 5-{1'-[(1-cyclopropyl-5-ethoxisoquinolin-7-yl)carbonyl]-4-oxospiro[chroman-2,4'-piperidin]-6-yl}nicotinate

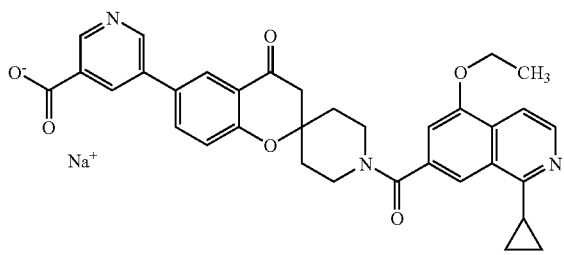

The compound was prepared according to the procedure described in "reference Example 37" and "Example 39". 1-Cyclopropyl-5-ethoxy-isoquinoline-7-carboxylic acid was used in place of 1-cyclopropyl-5-methoxy-isoquinoline-7-carboxylic acid. $^1$H-NMR (400 MHz, DMSO-$d_6$) δ: 8.90 (1H, d, J=1.7 Hz), 8.74 (1H, d, J=2.4 Hz), 8.35 (1H, d, J=5.9 Hz), 8.29-8.27 (1H, m), 8.05 (1H, br s), 7.99-7.95 (2H, m), 7.74 (1H, d, J=5.9 Hz), 7.23 (1H, d, J=9.0 Hz), 7.17 (1H, br s), 4.32 (1H, br s), 4.26 (2H, q, J=7.0 Hz), 3.59-3.44 (1H, m), 3.35-3.23 (2H, m), 2.95-2.86 (1H, m), 2.95 (2H, s), 2.16-1.78 (4H, m), 1.46 (3H, t, J=7.0 Hz), 1.15-1.02 (4H, m). MS [M+H]+=578, [M+Na]+=600.

EXAMPLE 55

Sodium 5-{1'-[(8-cyclopropyl-4-methoxy-quinolin-2-yl)carbonyl]-4-oxospiro[chroman-2,4'-piperidin]-6-yl}nicotinate

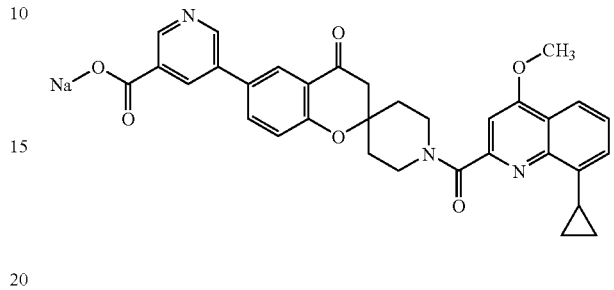

5-{1'-[(8-Cyclopropyl-4-methoxy-quinolin-2-yl)carbonyl]-4-oxospiro[chroman-2,4'-piperidin]-6-yl}nicotinic acid (3.53 g, 6.26 mmol) was suspended in H$_2$O (35 mL) and 1N NaOH (6.26 mL) was added at 0° C. The resulted solution was purified by ODS column chromatography (eluent: H$_2$O/MeOH=10/0 to 40/60) to afford sodium 5-{1'-[(8-Cyclopropyl-4-methoxy-quinolin-2-yl)carbonyl]-4-oxospiro[chroman-2,4'-piperidin]-6-yl}nicotinate as a colorless solid. $^1$H-NMR (400 MHz, DMSO-$d_6$) δ: 8.91 (1.0H, d, J=1.7 Hz), 8.74 (1.0H, d, J=2.4 Hz), 8.30-8.28 (1.0H, m), 7.98-7.93 (3.0H, m), 7.49 (1.0H, dd, J=8.5, 7.3 Hz), 7.27-7.23 (2.0H, m), 7.20 (1.0H, s), 4.43-4.30 (1.0H, m), 4.07 (3.0H, s), 3.94-3.85 (1.0H, m), 3.61-3.46 (1.0H, m), 3.35-3.27 (1.0H, m), 3.12-3.03 (1.0H, m), 2.97 (2.0H, s), 2.17-2.06 (1.0H, m), 2.04-1.79 (3.0H, m), 1.15-1.03 (2.0H, m), 0.89-0.69 (2.0H, m). MS [M+Na]+=586.

EXAMPLE 56

1'-[(4,8-Dimethoxyquinolin-2-yl)carbonyl]-6-(1H-pyrazol-4-yl)spiro[chroman-2,4'-piperidin]-4-one

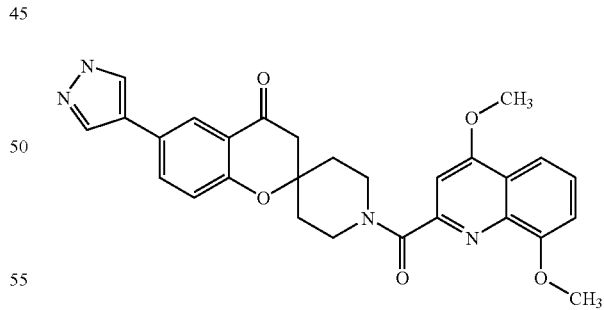

The compound was prepared according to the procedure described in Example 12 but using pyrazole-4-boronic acid pinacol ester in place of pyridine-3-boronic acid 1',3'-propanediol cyclic ester. $^1$H-NMR (400 MHz, CDCl$_3$) δ: 7.97 (1H, d, J=2.0 Hz), 7.83 (2H, s), 7.75 (1H, d, J=8.4 Hz), 7.64 (1H, dd, J=8.4, 2.0 Hz), 7.45 (1H, dd, J=8.4, 8.0 Hz), 7.16 (1H, s), 7.07 (1H, d, J=8.0 Hz), 7.02 (1H, d, J=8.4 Hz), 4.55-4.62 (1H, m), 4.07 (3H, s), 4.03 (3H, s), 4.00-4.20 (1H, m), 3.50-3.70 (1H, m), 3.30-3.45 (1H, m), 2.82 (1H, d, J=16.8

Hz), 2.76 (1H, d, J=16.8 Hz), 2.18-2.30 (1H, m), 2.00-2.12 (1H, m), 1.75-2.00 (2H, m). MS [M+H]⁺=499.

EXAMPLE 57

1'-[(4,8-Dimethoxyquinolin-2-yl)carbonyl]-6-(1-methyl-1H-pyrazol-4-yl)spiro[chroman-2,4'-piperidin]-4-one

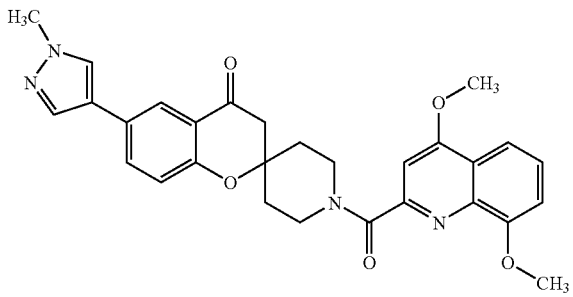

The compound was prepared according to the procedure described in Example 12 but using 1-methylpyrazole-4-boronic acid pinacol ester in place of pyridine-3-boronic acid 1',3'-propanediol cyclic ester. ¹H-NMR (400 MHz, CDCl₃) δ: 7.93 (1H, d, J=2.0 Hz), 7.75 (1H, d, J=8.0 Hz), 7.71 (1H, s), 7.62 (1H, dd, J=8.8, 1.2 Hz), 7.58 (1H, s), 745. (1H, dd, J=8.0, 8.0 Hz), 7.17 (1H, s), 7.06 (1H, d, J=8.0 Hz), 7.01 (1H, d, J=8.8 Hz), 4.50-4.62 (1H, m), 4.00-4.20 (1H, m), 4.07 (3H, s), 4.02 (3H, s), 3.93 (3H, s), 3.50-3.70 (1H, m), 3.30-3.45 (1H, m), 2.83 (1H, d, J=16.8 Hz), 2.76 (1H, d, J=16.8 Hz), 2.15-2.30 (1H, m), 2.00-2.15 (1H, m), 1.70-1.95 (2H, m). MS [M+H]⁺=513.

EXAMPLE 58

1'-[(4,8-Dimethoxyquinolin-2-yl)carbonyl]-6-(1,1-dioxidothiomorpholin-4-yl)spiro[chroman-2,4'-piperidin]-4-one

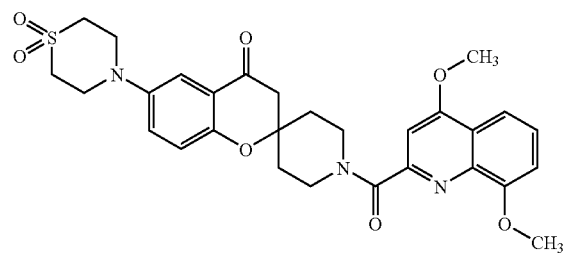

The compound was prepared according to the procedure described in Example 10 but using thiomorpholine-1,1-dioxide in place of 5-amino-1-methyl-1H-pyrazole. ¹H-NMR (400 MHz, CDCl₃) δ: 7.76 (1H, dd, J=8.4, 1.2 Hz), 7.46 (1H, dd, J=8.4, 8.0 Hz), 7.37 (1H, d, J=2.8 Hz), 7.17 (1H, s), 7.17 (1H, dd, J=8.8, 2.8 Hz), 7.07 (1H, dd, J=8.0, 1.2 Hz), 6.98 (1H, d, J=8.8 Hz), 4.50-4.65 (1H, m), 4.10-4.20 (1H, m), 4.08 (3H, s), 4.03 (3H, s), 3.70-3.80 (4H, m), 3.50-3.70 (1H, m), 3.30-3.40 (1H, m), 3.10-3.20 (4H, m), 2.80 (1H, d, J=16.8 Hz), 2.74 (1H, d, J=16.8 Hz), 2.20-2.30 (1H, m), 2.10-2.20 (1H, m), 1.80-1.95 (2H, m). MS [M+H]⁺=566.

EXAMPLE 59

1'-[(4,8-Dimethoxyquinolin-2-yl)carbonyl]-6-(3-oxopiperazin-1-yl)spiro[chroman-2,4'-piperidin]-4-one

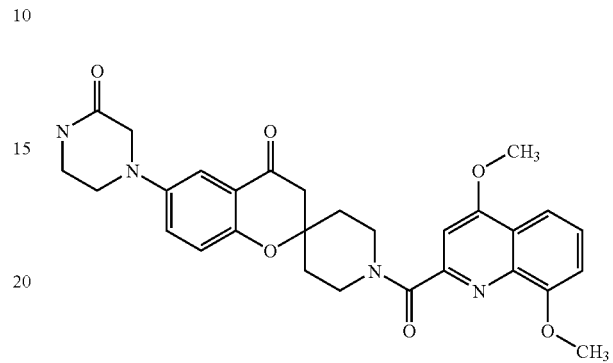

1'-[(4,8-dimethoxyquinolin-2-yl)carbonyl]-6-[(4-hydroxymethyl)-3-oxopiperazin-1-yl)]spiro[chroman-2,4'-piperidin]-4-one (220 mg, 0.393 mmol) was dissolved in MeOH (10 mL) and 28% NH₃ aq. (5 mL) was added thereto. After stirred for 11 h, the solvents were removed in vacuo. The residue was purified by silica gel thin-layer chromatography (EtOAc only, then CHCl₃/MeOH=9/1) to obtain the intended compound as a yellow foam. ¹H-NMR (400 MHz, CDCl₃) δ: 7.77 (1H, dd, J=8.8, 1.2 Hz), 7.46 (1H, dd, J=8.8, 8.0 Hz), 7.36 (1H, d, J=3.2 Hz), 7.19 (1H, s), 7.15 (1H, dd, J=8.8, 3.2 Hz), 7.08 (1H, dd, J=8.0, 1.2 Hz), 6.99 (1H, d, J=8.8 Hz), 6.14 (1H, br s), 4.50-4.65 (1H, m), 4.10-4.20 (1H, m), 4.08 (3H, s), 4.03 (3H, s), 3.82 (2H, s), 3.50-3.60 (1H, m), 3.45-3.50 (2H, m), 3.30-3.45 (3H, m), 2.79 (1H, d, J=16.8 Hz), 2.74 (1H, d, J=16.8 Hz), 2.10-2.20 (1H, m), 2.00-2.10 (1H, m), 1.80-1.95 (2H, m). MS [M+H]⁺=531.

EXAMPLE 60

1'-[(4,8-Dimethoxyquinolin-2-yl)carbonyl]-6-(4H-1,2,4-triazol-3-ylamino)spiro[chroman-2,4'-piperidin]-4-one

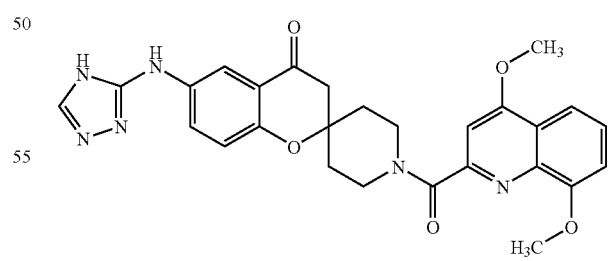

1'-[(4,8-dimethoxyquinolin-2-yl)carbonyl]-6-[1-(2-trimethylsilanylethoxymethyl)-1H-[1,2,4]triazol-3-ylamino] spiro[chroman-2,4'-piperidin]-4-one (27.0 mg, 0.0419 mmol) was dissolved in CHCl₃ (1 mL), and TFA (1 mL) and ethane-1,2-diamine (35.0 mg, 0.583 mmol) was added thereto. After stirring at room temperature for 16 h, the reaction mixture was diluted with CHCl₃ and 1N NaOH aq. The aqueous layer was extracted with CHCl₃ and combined organic layer was washed with brine, dried over MgSO₄. The desiccant was removed through filtration and the filtrate was concentrated under reduced pressure. The residue was purified by silica gel thin-layer chromatography (CHCl₃/MeOH=9/1) to obtain the intended compound as a yellow foam. ¹H-NMR (400 MHz, CDCl₃) δ7.95 (1H, d, J=2.8 Hz), 7.93 (1H, s), 7.76 (1H, dd, J=8.4, 1.2 Hz), 7.61 (1H, dd, J=8.8, 2.8 Hz), 7.46 (1H, dd, J=8.4, 8.4 Hz), 7.19 (1H, br s), 7.11 (1H, s), 7.08 (1H, d, J=8.4, 1.2 Hz), 6.93 (1H, d, J=8.8 Hz), 4.50-4.60 (1H, m), 4.08 (3H, s), 4.03 (3H, s), 3.90-4.10 (1H, m), 3.50-3.65 (1H, m), 3.25-3.40 (1H, m), 2.73 (1H, d, J=16.8 Hz), 2.68 (1H, d, J=16.8 Hz), 2.15-2.30 (1H, m), 1.95-2.10 (1H, m), 1.50-1.90 (2H, m). MS [M+H]⁺=515.

EXAMPLE 61

1'-[(4-Hydroxy-8-methoxyquinolin-2-yl)carbonyl]-6-(1H-tetrazol-5-yl)spiro[chroman-2,4'-piperidin]-4-one

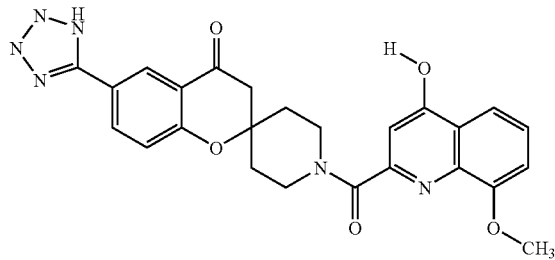

The compound was prepared according to the procedure described in Example 17, using 4-hydroxy-8-methoxyquinoline-2-carboxylic acid instead of 4,8-dimethoxyquinoline-2-carboxylic acid. ¹H-NMR (400 MHz, DMSO-d₆) δ: 11.59 (1H, s), 8.42 (1H, d, J=2.0 Hz), 8.24 (1H, dd, J=8.5 Hz, J=2.0 Hz) 7.67-7.58 (1H, m), 7.33 (1H, d, J=8.5 Hz), 7.30-7.23 (2H, m), 6.02 (1H, m), 4.27-4.14 (1H, m), 3.98 (3H, s), 3.48-3.15 (3H, m), 2.96 (2H, s), 2.14-2.03 (1H, m), 2.01-1.78 (3H, m). MS [M+H+]=487.

EXAMPLE 62

1'-[(8-Hydroxy-4-methoxyquinolin-2-yl)carbonyl]-6-(1H-tetrazol-5-yl)spiro[chroman-2,4'-piperidin]-4-one

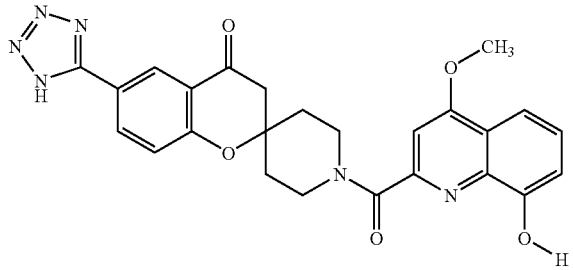

The compound was prepared according to the procedure described in Example 17, using 8-hydroxy-4-methoxyquinoline-2-carboxylic acid instead of 4,8-dimethoxyquinoline-2-carboxylic acid. ¹H-NMR (400 MHz, DMSO-d₆) δ: 9.51 (1H, br s), 8.43 (1H, d, J=2.3 Hz), 8.30 (1H, d, J=2.3 Hz), 8.24 (1H, dd, J=8.0, 2.3 Hz), 7.55 (1H, d, J=8.0 Hz), 7.42 (1H, t, J=8.0 Hz), 7.34 (1H, d, J=8.0 Hz), 7.14 (1H, s), 7.11 (1H, d, J=8.0 Hz), 4.36-4.33 (1H, m), 4.06 (3H, s), 3.58-3.55 (1H, m), 3.48-3.26 (2H, m), 3.00 (2H, s), 2.14-2.10 (1H, m), 2.00-1.81 (3H, m).

EXAMPLE 63

1-[(8-Cyclopropyl-4-methoxyquinolin-2-yl)carbonyl]-6'-(1H-tetrazol-5-yl)spiro[piperidine-4,2'-thiochroman]-4'-one

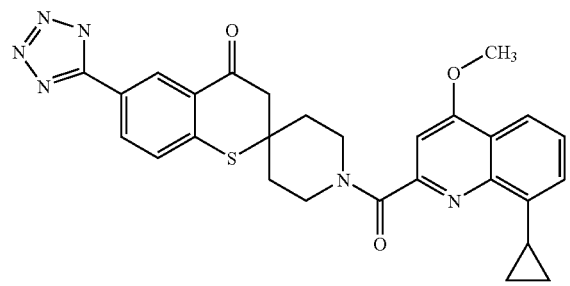

The compound was prepared according to the procedure described in Example 45 but using 6'-(1H-tetrazol-5-yl)spiro[piperidine-4,2'-thiochroman]-4'(3'H)-one instead of 6'-(1H-tetrazol-5-yl)spiro[piperidine-4,2'-chroman]-4'(3'H)-one. ¹H-NMR (400 MHz, DMSO-d₆) δ: 8.62-8.60 (1.0H, m), 8.14 (1.0H, dd, J=8.3, 2.0 Hz), 7.94 (1.0H, d, J=8.3 Hz), 7.64 (1.0H, dd, J=8.3, 1.5 Hz), 7.51-7.46 (1.0H, m), 7.25 (1.0H, d, J=7.3 Hz), 7.21 (1.0H, d, J=1.5 Hz), 4.36-4.28 (1.0H, m), 4.07 (3.0H, s), 3.94-3.85 (1.0H, m), 3.52-3.42 (1.0H, m), 3.40-3.25 (1.0H, m), 3.19 (1.0H, d, J=17.0 Hz), 3.15 (1.0H, d, J=17.0 Hz), 3.11-3.01 (1.0H, m), 2.10-1.81 (4.0H, m), 1.10-1.03 (2.0H, m), 0.88-0.72 (2.0H, m). _MS [M+H]+=527.

EXAMPLE 64

6'-tert-Butyl-1-[(4,8-dimethoxyquinolin-2-yl)carbonyl]spiro[piperidine-4,2'-pyrano[2,3-c]pyridin]-4'(3'H)-one

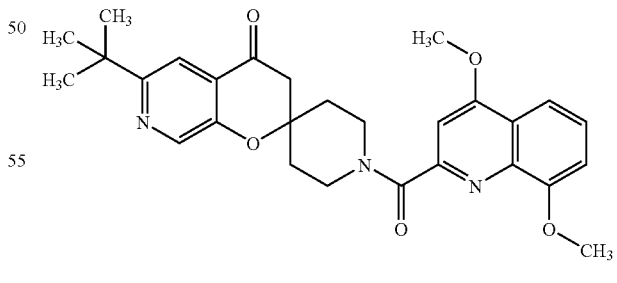

The compound was prepared according to the procedure described in Example 1, using 6'-tert-butylspiro[piperidine-4,2'-pyrano[2,3-c]pyridin]-4'(3'H)-one instead of N-(4-oxospiro[chroman-2,4'-piperidin]-6-yl)acetamide and using 4,8-dimethoxyquinoline-2-carboxylic acid in place of 4-methoxyquinoline-2-carboxylic acid. ¹H-NMR (400 MHz, CDCl₃) δ: 8.49 (1H, d, J=1.0 Hz), 7.77 (1H, dd, J=8.0, 1.1

Hz), 7.64 (1H, d, J=1.0 Hz), 7.47 (1H, t, J=8.0 Hz), 7.19 (1H, s), 7.08 (1H, dd, J=8.0, 1.1 Hz), 4.65-4.57 (1H, m), 4.23-4.15 (1H, m), 4.08 (3H, s), 4.03 (3H, s), 3.66-3.33 (2H, m), 2.90-2.76 (2H, m), 2.24-1.83 (4H, m), 1.36 (9H, s). MS (M+H)⁺= 490.

EXAMPLE 65

Sodium 5-{1'-[(8-cyclopropyl-4-ethoxy-1,7-naphthyridin-2-yl)carbonyl]-4-oxospiro[chroman-2,4'-piperidin]-6-yl}nicotinate

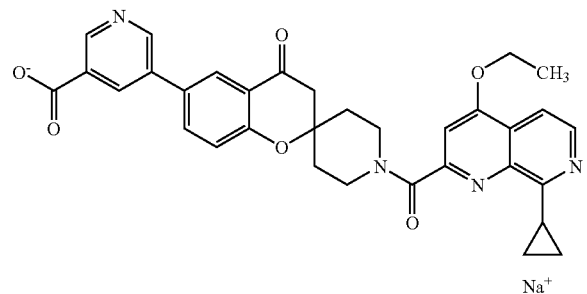

The compound was prepared according to the procedure described in "reference Example 37" and "Example 39". 8-Cyclopropyl-4-ethoxy-1,7-naphtyridine-2-carboxylic acid was used in place of 1-cyclopropyl-5-methoxy-isoquinoline-7-carboxylic acid. ¹H-NMR (400 MHz, DMSO-d₆) δ: 8.91 (1H, d, J=1.5 Hz), 8.75 (1H, d, J=2.4 Hz), 8.41 (1H, d, J=5.6 Hz), 8.30-8.28 (1H, m), 8.00-7.96 (2H, m), 7.71 (1H, d, J=5.6 Hz), 7.36 (1H, s), 7.25 (1H, d, J=9.3 Hz), 4.41-4.31 (1H, m), 4.37 (2H, q, J=7.0 Hz), 3.79-3.71 (1H, m), 3.58-3.40 (2H, m), 3.39-3.27 (1H, m), 2.97 (2H, s), 2.16-2.09 (1H, m), 2.03-1.79 (3H, m), 1.47 (3H, t, J=7.0 Hz), 1.14-1.07 (4H, m). MS [M+Na]+=601.

EXAMPLE 66

Sodium 2-1'-[(1-cyclopropyl-5-methoxyisoquinolin-7-yl)carbonyl]-4-oxo-spiro[chroman-2,4'-piperidin]-6-yl}isonicotinate

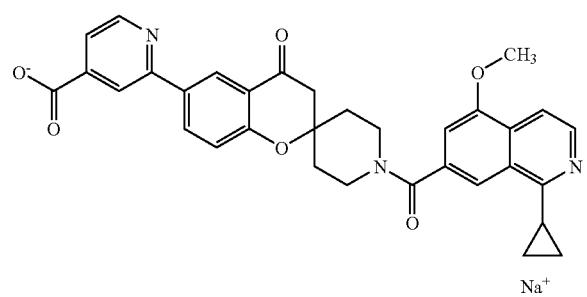

The compound was prepared according to the procedure described in Reference Example 37 and Example 39. Methyl 2-[4-oxo-spiro(chromane-2,4'-piperidin)-6-yl]isonicotinate was used in place of methyl 5-[4-oxo-spiro(chromane-2,4'-piperidin)-6-yl]nicotinate. ¹H-NMR (400 MHz, DMSO-d₆) δ: 8.54 (1H, dd, J=4.9, 0.7 Hz), 8.41 (1H, d, J=2.4 Hz), 8.35 (1H, d, J=5.9 Hz), 8.31 (1H, dd, J=8.8, 2.4 Hz), 8.15 (1H, s), 8.07 (1H, s), 7.73 (1H, dd, J=5.9, 0.7 Hz), 7.59 (1H, dd, J=4.9, 1.2 Hz), 7.22-7.18 (2H, m), 4.42-4.23 (1H, br m), 4.01 (3H, s), 3.64-3.43 (1H, br m), 3.38-3.23 (2H, m), 2.95-2.87 (1H, br m), 2.95 (2H, s), 2.16-2.04 (1H, br m), 2.01-1.80 (3H, m), 1.15-1.04 (4H, m). MS [M+Na]+=586.

EXAMPLE 67

Sodium 2-{1'-[(1-cyclopropyl-5-ethoxyisoquinolin-7-yl)carbonyl]-4-oxospiro[chroman-2,4'-piperidin]-6-yl}isonicotinate

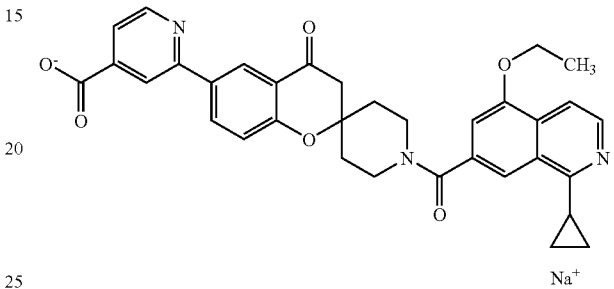

The compound was prepared according to the procedure described in "reference Example 37" and "Example 39". Methyl 2-[4-oxo-spiro(chromane-2,4'-piperidine)-6-yl]isonicotinate and 1-cyclopropyl-5-ethoxy-isoquinoline-7-carboxylic acid were used in place of methyl 5-[4-oxo-spiro(chromane-2,4'-piperidin)-6-yl]nicotinate and 1-cyclopropyl-5-methoxy-isoquinoline-7-carboxylic acid, respectively. ¹H-NMR (400 MHz, DMSO-d₆) δ: 8.54 (1H, dd, J=4.9, 0.7 Hz), 8.41 (1H, d, J=2.2 Hz), 8.35 (1H, d, J=5.9 Hz), 8.31 (1H, dd, J=8.8, 2.2 Hz), 8.16-8.14 (1H, m), 8.05 (1H, s), 7.74 (1H, dd, J=5.9, 0.7 Hz), 7.59 (1H, dd, J=4.9, 1.2 Hz), 7.20 (1H, d, J=8.8 Hz), 7.17 (1H, s), 4.38-4.24 (1H, m), 4.26 (2H, q, J=7.1 Hz), 3.60-3.44 (1H, br m), 3.33-3.31 (2H, m), 2.95-2.86 (1H, m), 2.95 (2H, s), 2.18-2.05 (1H, br m), 2.00-1.80 (3H, m), 1.46 (3H, t, J=7.1 Hz), 1.16-1.03 (4H, m). MS [M+Na]+=600.

EXAMPLE 68

4,8-Dimethoxy-2-({6-[(methoxycarbonyl)amino]-4-oxospiro[chroman-2,4'-piperidin]-1'-yl}carbonyl) quinoline hydrochloride

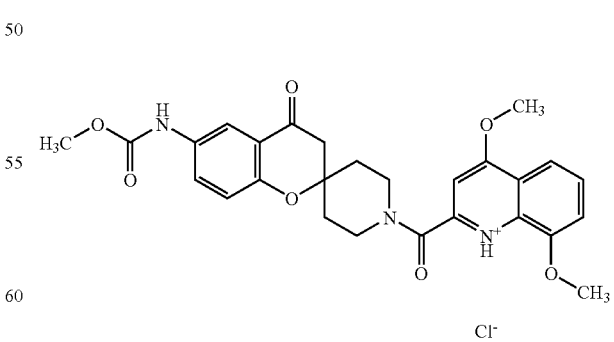

The free form of the compound was prepared according to the procedure described in Example 30 but using 6-amino-1'-[(4,8-dimethoxyquinolin-2-yl)carbonyl]spiro[chroman-2,4'-piperidin]-4-one and methyl chloroformate instead of 6-(piperazin-1-yl)-1'-[(4,8-dimethoxyquinolin-2-yl)carbonyl] spiro[chroman-2,4'-piperidin]-4-one and Ac$_2$O. Then the material was converted to HCl salt according to the procedure described in Example 2. $^1$H-NMR (400 MHz, DMSO-d$_6$) δ: 9.65 (1H, s), 7.84 (1H, s), 7.73-7.53 (3H, m), 7.36-7.25 (2H, m), 7.06 (1H, d, J=9.0 Hz), 4.34-4.18 (1H, m), 4.10 (3H, s), 3.97 (3H, s), 3.69-3.26 (3H, m), 3.64 (3H, s), 2.86 (2H, s), 2.10-1.71 (4H, m). MS [M+H]+=506.

EXAMPLE 69

2-{1'-[(4,8-Dimethoxyquinolin-2-yl)carbonyl]-4-oxospiro[chroman-2,4'-piperidin]-6-yl}-2-methyl-propanoic acid

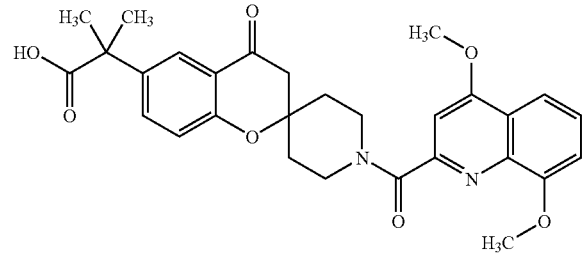

2-{1'-[(4,8-dimethoxyquinolin-2-yl)carbonyl]-4-oxospiro[chromane-2,4'-piperidin]-6-yl}-2-methylpropanoic acid benzyl ester (830 mg) was dissolved in 25 mL of MeOH and hydrogenated at 1.5 atmosphere over 100 mg of 10% Pd/C for 5 hrs. The mixture was filtered and the filtrate was concentrated and purified on preparative SiO$_2$ PTC (CHCl$_3$/MeOH=10:1) to give the intended compound as a colorless amorphous solid. $^1$H-NMR (400 MHz, CD$_3$OD), 7.93 (1H, s), 7.88 (1H, d, J=2.3 Hz), 7.81 (1H, d, J=8.8 Hz), 7.65 (1H, dd, J=8.8 Hz, 2.3 Hz), 7.55 (1H, t, J=8.2 Hz), 7.27 (1H, J=8.2 Hz), 7.17 (1H, s), 7.10 (1H, d, J=8.2 Hz), 4.5-4.6 (1H, m), 4.15 (3H, s), 4.06 (3H, s), 3.3-3.7 (3H, m), 2.90 (1H, d, J=16.5 Hz), 2.84 (1H, d, J=16.5 Hz), 1.9-2.3 (4H, m). MS [M+H]+=519.

EXAMPLE 70

1'-[(1,5-Dimethoxyisoquinolin-3-yl)carbonyl]-6-(1H-tetrazol-5-yl)spiro[chroman-2,4'-piperidin]-4-one

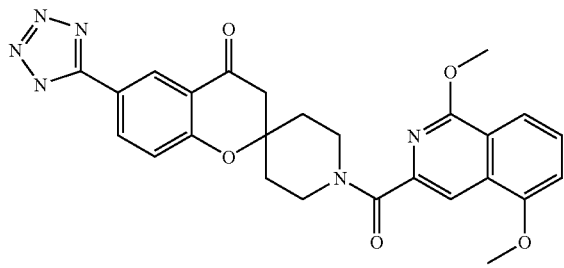

The compound was prepared according to the Example 17, using 1,5-dimethoxyisoquinoline-3-carboxylic acid instead of 4,8-dimethoxyquinoline-2-carboxylic acid.

$^1$H-NMR (400 MHz, DMSO-d$_6$) δ: 8.42 (1H, d, J=2.2 Hz), 8.23 (1H, dd, J=8.8, 2.2 Hz), 7.80 (1H, d, J=0.7 Hz), 7.73 (1H, dt, J=8.2, 0.7 Hz), 7.61 (1H, t, J=8.2 Hz), 7.35 (1H, d, J=8.8 Hz), 7.29 (1H, d, J=8.2 Hz), 4.30 (1H, d, J=12.4 Hz), 4.05 (3H, s), 3.99 (3H, s), 3.90 (1H, d, J=12.4 Hz), 3.49 (1H, t, J=12.4 Hz), 3.30-3.28 (1H, m), 3.00 (2H, s), 2.05-1.89 (4H, m). MS [M+H]+=501.

EXAMPLE 71

5-{1'-[(1-Cyclopropyl-5-methoxyisoquinolin-7-yl)carbonyl]-4-oxo-spiro[chromane-2,4'-piperidin]-6-yl}nicotinic acid The compound was prepared according to the procedure described in Example 36 but using 1-(1-cyclopropyl-5-methoxy-isoquinolin-7-carbonyl)-1H-imidazole instead of (8-cyclopropyl-4-methoxy-quinolin-2-yl)-imidazol-1-yl-methanone. $^1$H-NMR (400 MHz, DMSO-d$_6$) δ: 9.03-8.99 (2H, m), 8.40-8.37 (1H, m), 8.36 (1H, d, J=5.9 Hz), 8.08-8.02 (3H, m), 7.73 (1H, d, J=5.9 Hz), 7.25 (1H, d, J=9.5 Hz), 7.19 (1H, s), 4.40-4.28 (1H, br m), 4.01 (3H, s), 3.64-3.18 (3H, m), 3.00-2.86 (1H, m), 2.96 (2H, s), 2.17-2.03 (1H, br m), 1.99-1.79 (3H, m), 1.16-1.01 (4H, m). MS [M+H]+=564.

The following compounds in Examples 72-74 were prepared according to the procedure described in Example 17.

EXAMPLE 72

1'-{[4-(Difluoromethoxy)-8-methoxyquinolin-2-yl]carbonyl}-6-(1H-tetrazol-5-yl)spiro[chromane-2,4'-piperidin]-4(3H)-one

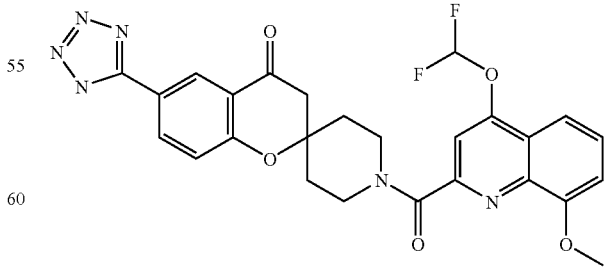

$^1$H-NMR (400 MHz, DMSO-d$_6$) δ: 8.42 (1H, s), 8.25 (1H, dd, J=8.8, 2.2 Hz), 7.71 (1H, t, J=72.4 Hz), 7.66-7.62 (2H, m), 7.48 (1H, s), 7.37-7.32 (2H, m), 4.32 (1H, m), 3.97 (3H, s), 3.75 (1H, m), 3.50 (1H, m), 3.37-3.34 (1H, m), 3.01 (2H, s), 2.11 (1H, m), 1.97-1.84 (3H, m).

EXAMPLE 73

1'-[4-(2-Hydroxyethoxy)-8-methoxy-2-naphthoyl]-6-(1H-tetrazol-5-yl)spiro[chromane-2,4'-piperidin]-4(3H)-one

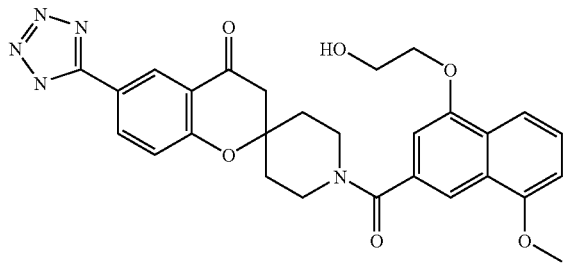

$^1$H-NMR (400 MHz, DMSO-d$_6$) δ: 8.42 (1H, d, J=2.2 Hz), 8.23 (1H, dd, J=8.8, 2.2 Hz), 7.81 (1H, d, J=8.5 Hz), 7.71 (1H, s), 7.46 (1H, t, J=8.0 Hz), 7.34 (1H, d, J=8.8 Hz), 7.04 (1H, d, J=7.6 Hz), 6.96-6.96 (1H, s), 4.37-4.24 (1H, m), 4.17 (2H, t, J=4.8 Hz), 3.96 (3H, s), 3.84 (2H, t, J=4.9 Hz), 3.69-3.23 (3H, m), 2.99 (2H, s), 2.14-1.74 (4H, m).

EXAMPLE 74

1'-{[2-(3,4-Dimethoxyphenyl)quinolin-4-yl]carbonyl}-6-(2H-tetrazol-5-yl)spiro[chromane-2,4'-piperidin]-4(3H)-one

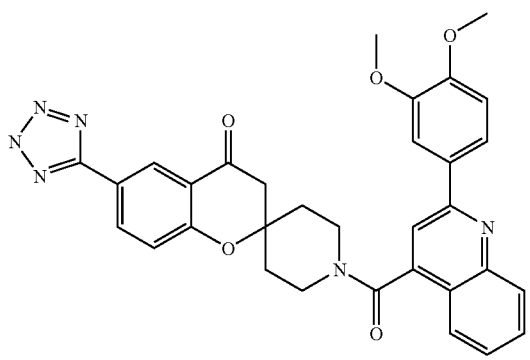

$^1$H-NMR (400 MHz, DMSO-d$_6$) δ: 8.41 (1H, d, J=2.2 Hz), 8.23 (1H, d, J=8.5 Hz), 8.13-8.11 (2H, m), 7.86-7.80 (4H, m), 7.62 (1H, t, J=7.4 Hz), 7.34 (1H, t, J=9.0 Hz), 7.13 (1H, t, J=9.0 Hz), 4.48 (1H, d, J=11.5 Hz), 3.89-3.86 (6H, m), 3.39-3.36 (2H, m), 3.20-3.16 (1H, m), 3.01-2.99 (2H, m), 2.16 (1H, d, J=13.9 Hz), 1.90-1.85 (3H, m). MS [M+H]+=577.

EXAMPLE 75

Methyl 5-{1'-[(1-cyclopropyl-5-methoxyisoquinolin-7-yl)carbonyl]-4-oxo-spiro[chromane-2,4'-piperidin]-6-yl}nicotinate

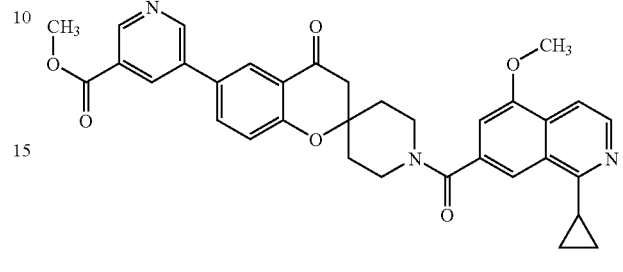

1-Cyclopropyl-5-methoxy-isoquinoline-7-carboxylic acid (900 mg, 3.70 mmol), 5"-{4-oxospiro-[chroman-2,4'-piperidin]-6-yl}nicotinic acid methyl ester di-hydrochloride (1.89 g, 4.44 mmol), EDCI (852 mg, 4.44 mmol), HOBT (675 mg, 4.44 mmol), and TEA (2.06 mL, 14.8 mmol) were suspended in DMF (500 mL) and stirred at room temperature for 16 h. After removal of the solvent, the residue was diluted with CHCl$_3$ and H$_2$O. The aqueous layer was extracted with CHCl$_3$ and the combined organic layer was washed with saturated NaHCO$_3$ aq. and brine, dried over MgSO$_4$. The desiccant was removed through filtration and the filtrate was concentrated under reduced pressure. The residue was purified by silica gel column chromatography (hexane/EtOAc=10/0 to 0/10) to obtain the intended compound as a pale yellow foam. $^1$H-NMR (400 MHz, CDCl$_3$) δ: 9.19 (1.0H, d, J=2.2 Hz), 8.99 (1.0H, d, J=2.2 Hz), 8.48 (1.0H, dd, J=2.2, 2.2 Hz), 8.41 (1.0H, d, J=5.9 Hz), 8.16 (1.0H, d, J=2.2 Hz), 8.01 (1.0H, s), 7.83-7.79 (2.0H, m), 7.19 (1.0H, d, J=8.5 Hz), 7.01 (1.0H, s), 4.75-4.51 (1.0H, br m), 4.04 (3.0H, s), 3.99 (3.0H, s), 3.91-3.30 (3.0H, m), 2.85 (2.0H, s), 2.69-2.63 (1.0H, m), 2.37-2.03 (2.0H, m), 1.93-1.54 (2.0H, m), 1.29-1.22 (2.0H, m), 1.16-1.09 (2.0H, m). MS [M+H]+=578.

EXAMPLE 76

Sodium 5-{1'-[(8-cyclopropyl-4-methoxyquinolin-2-yl)carbonyl]-4-oxo-spiro[chromane-2,4'-piperidin]-6-yl}nicotinate 1-oxide

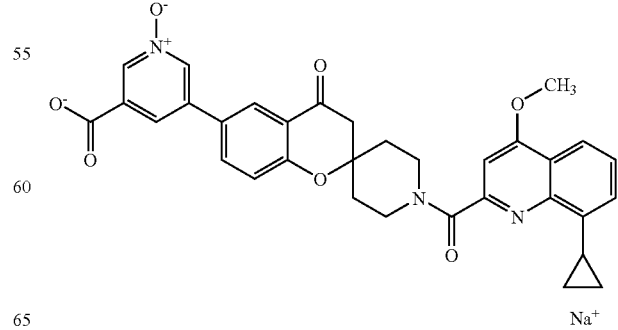

The compound was prepared according to Example 39 using 8-cyclopropyl-4-methoxyquinoline-2-carboxylic acid and methyl 4-oxo-spiro[chromane-2,4'-piperidin]-6-yl}nicotinate 1-oxide instead. ¹H-NMR (400 MHz, DMSO-d₆) δ: 8.47 (1H, dd, J=1.7, 1.7 Hz), 8.30 (1H, dd, J=1.7, 1.0 Hz), 8.00-7.97 (2H, m), 7.94 (1H, dd, J=8.2, 1.7 Hz), 7.84 (1H, dd, J=1.7, 1.0 Hz), 7.49 (1H, dd, J=8.2, 7.6 Hz), 7.27-7.22 (2H, m), 7.20 (1H, s), 4.40-4.31 (1H, m), 4.07 (3H, s), 3.93-3.84 (1H, m), 3.57-3.46 (1H, m), 3.38-3.27 (1H, m), 3.12-3.03 (1H, m), 2.97 (2H, s), 2.15-2.07 (1H, m), 2.02-1.79 (3H, m), 1.14-1.03 (2H, m), 0.87-0.71 (2H, m). MS [M+Na]+= 602.

EXAMPLE 77

Sodium 5-{1'-[(8-cyclopropyl-4-methoxyquinolin-2-yl)carbonyl]-4-oxo-spiro[chromane-2,4'-piperidin]-6-yl}-1-methyl-2-oxo-1,2-dihydropyridine-3-carboxylate

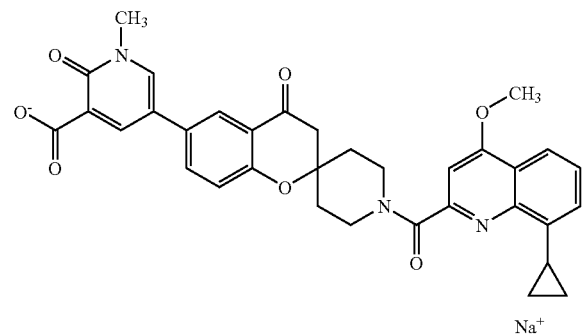

Methyl 5-{1'-[(8-cyclopropyl-4-methoxyquinolin-2-yl)carbonyl]-4-oxo-spiro[chromane-2,4'-piperidin]-6-yl}-1-methyl-2-oxo-1,2-dihydropyridine-3-carboxylate. (210 mg, 0.345 mmol) was suspended in MeOH (2 ml) and THF (2 ml), and 1N NaOH (0.5 ml) was added thereto. After stirred at room temperature for 20 h, the resulting solid was filtered, washed with THF and dried to obtain the intended compound as a pale yellow solid. ¹H-NMR (400 MHz, DMSO-d₆) δ: 8.08 (1H, d, J=2.4 Hz), 7.96 (1H, d, J=2.4 Hz), 7.94 (1H, d, J=8.4 Hz), 7.83 (1H, d, J=2.4 Hz), 7.79 (1H, dd, J=8.4, 2.4 Hz), 7.49 (1H, dd, J=8.4, 7.3 Hz), 7.25 (1H, d, J=7.3 Hz), 7.21-7.17 (2H, m), 4.40-4.31 (1H, m), 4.07 (3H, s), 3.93-3.83 (1H, m), 3.56-3.46 (1H, m), 3.49 (3H, s), 3.38-3.25 (1H, m), 3.12-3.03 (1H, m), 2.94 (2H, s), 2.14-2.06 (1H, m), 2.01-1.78 (3H, m), 1.14-1.02 (2H, m), 0.88-0.72 (1H, m). MS [M+H]+= 594.

The following compounds in Example 78-82 were prepared according to the procedure described in Example 39.

EXAMPLE 78

Sodium 5-{1'-[(1-cyclopropyl-5-methoxyisoquinolin-7-yl)carbonyl]-4-oxo-spiro[chromane-2,4'-piperidin]-6-yl}-2-fluorobenzoate

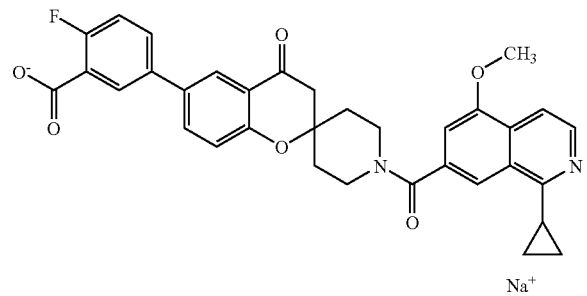

¹H-NMR (400 MHz, DMSO-d₆) δ: 8.35 (1H, d, J=5.9 Hz), 8.07 (1H, s), 7.88 (1H, d, J=2.4 Hz), 7.85 (1H, dd, J=8.5, 2.4 Hz), 7.75-7.70 (2H, m), 7.48-7.42 (1H, m), 7.20-7.16 (2H, m), 7.04 (1H, dd, J=9.8, 8.5 Hz), 4.33 (1H, br s), 4.01 (3H, s), 3.62-3.44 (2H, br m), 3.33-3.31 (1H, m), 2.95-2.87 (1H, m), 2.93 (2H, s), 2.16-2.05 (1H, br m), 2.00-1.77 (3H, m), 1.15-1.04 (4H, m). MS [M+Na]+=603.

EXAMPLE 79

Sodium 4-{1'-[(8-cyclopropyl-4-ethoxyquinolin-2-yl)carbonyl]-4-oxo-spiro[chromane-2,4'-piperidin]-6-yl}pyridine-2-carboxylate

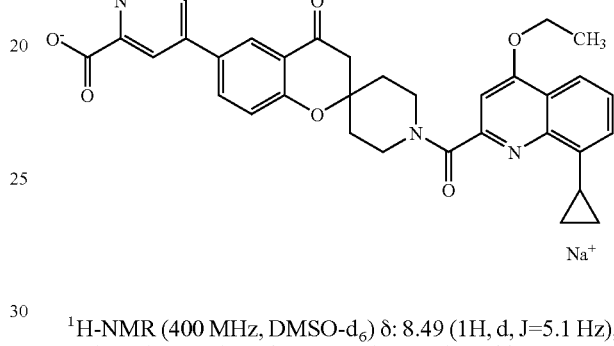

¹H-NMR (400 MHz, DMSO-d₆) δ: 8.49 (1H, d, J=5.1 Hz), 8.19 (1H, s), 8.08 (1H, d, J=2.4 Hz), 8.05 (1H, dd, J=8.5, 2.4 Hz), 7.95 (1H, dd, J=8.3, 1.2 Hz), 7.62 (1H, dd, J=5.1, 2.0 Hz), 7.48 (1H, dd, J=8.3, 7.3 Hz), 7.27 (1H, d, J=8.5 Hz), 7.24 (1H, dd, J=7.3, 1.2 Hz), 7.17 (1H, s), 4.39-4.32 (1H, m), 4.34 (2H, q, J=7.0 Hz), 3.92-3.81 (1H, m), 3.56-3.47 (1H, m), 3.41-3.26 (1H, m), 3.12-3.04 (1H, m), 2.98 (2H, s), 2.15-2.08 (1H, m), 2.02-1.80 (3H, m), 1.47 (3H, t, J=7.0 Hz), 1.12-1.03 (2H, m), 0.88-0.71 (2H, m). MS [M+Na]+=600.

EXAMPLE 80

Sodium 2-{1'-[(8-cyclopropyl-4-ethoxyquinolin-2-yl)carbonyl]-4-oxo-spiro[chromane-2,4'-piperidin]-6-yl}isonicotinate

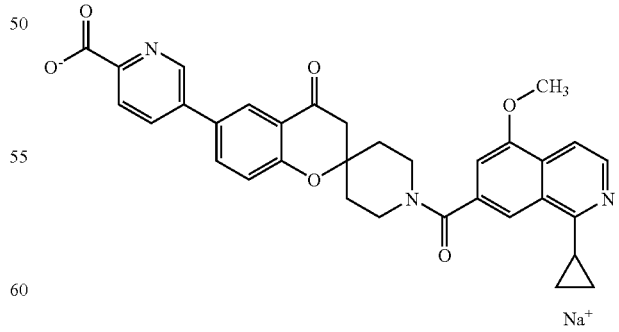

¹H-NMR (400 MHz, DMSO-d₆) δ: 8.69 (1H, d, J=1.7 Hz), 8.36 (1H, d, J=5.9 Hz), 8.07 (1H, s), 8.02-7.90 (4H, m), 7.73 (1H, d, J=5.9 Hz), 7.24 (1H, d, J=8.3 Hz), 7.19 (1H, s), 4.40-4.29 (1H, br m), 4.01 (3H, s), 3.64-3.44 (2H, br m), 3.32-3.30 (1H, m), 2.95-2.87 (1H, m), 2.95 (2H, s), 2.17-2.04 (1H, br m), 2.01-1.79 (3H, m), 1.16-1.04 (4H, m). MS [M+Na]+=586.

EXAMPLE 81

Sodium 2-{1'-[(8-cyclopropyl-4-ethoxyquinolin-2-yl)carbonyl]-4-oxo-spiro[chromane-2,4'-piperidin]-6-yl}isonicotinate

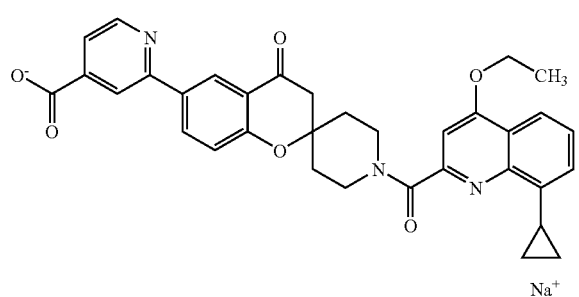

$^1$H-NMR (400 MHz, DMSO-d$_6$) δ: 8.54 (1H, d, J=4.9 Hz), 8.41 (1H, d, J=2.4 Hz), 8.30 (1H, dd, J=8.7, 2.4 Hz), 8.16 (1H, s), 7.95 (1H, dd, J=8.7, 1.0 Hz), 7.60 (1H, d, J=4.9 Hz), 7.48 (1H, dd, J=7.8, 7.8 Hz), 7.26-7.20 (2H, m), 7.17 (1H, s), 4.40-4.30 (1H, m), 4.34 (2H, q, J=6.9 Hz), 3.91-3.82 (1H, m), 3.56-3.47 (1H, m), 3.34-3.30 (1H, m), 3.12-3.03 (1H, m), 2.97 (2H, s), 2.16-2.07 (1H, m), 2.03-1.79 (3H, m), 1.47 (3H, t, J=6.9 Hz), 1.13-1.03 (2H, m), 0.86-0.73 (2H, m). MS [M+Na]+=600.

EXAMPLE 82

Sodium 4-{1'-[(1-cyclopropyl-5-methoxyisoquinolin-7-yl)carbonyl]-4-oxo-spiro[chromane-2,4'-piperidin]-6-yl}pyridine-2-carboxylate

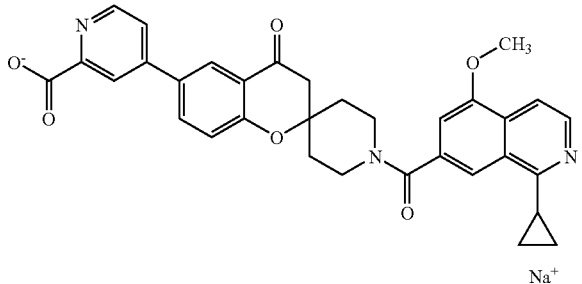

$^1$H-NMR (400 MHz, DMSO-d$_6$) δ: 8.48 (1H, dd, J=5.4, 0.7 Hz), 8.35 (1H, d, J=5.4 Hz), 8.15 (1H, d, J=1.2 Hz), 8.09-8.07 (2H, m), 8.05 (1H, dd, J=8.8, 2.4 Hz), 7.73 (1H, dd, J=5.4, 0.7 Hz), 7.60 (1H, dd, J=5.4, 2.4 Hz), 7.25 (1H, d, J=8.8 Hz), 7.19 (1H, s), 4.39-4.28 (1H, br m), 4.01 (3H, s), 3.62-3.45 (1H, br m), 3.34-3.31 (2H, m), 2.96-2.87 (1H, m), 2.96 (2H, s), 2.17-2.05 (1H, br m), 2.00-1.80 (3H, m), 1.15-1.03 (4H, m). MS [M+Na]+=586.

EXAMPLE 83

5-(1'-{[8-cyclopropyl-4-(2-hydroxyethoxy)quinolin-2-yl]carbonyl}-4-oxo-spiro[chromane-2,4'-piperidin]-6-yl)nicotinic acid

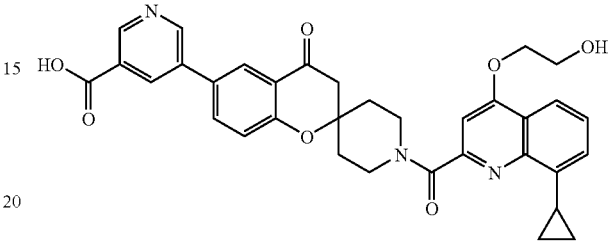

The compound was prepared according to Example 40 but using 5-(1'-{[8-cyclopropyl-4-(2-hydroxyethoxy)quinolin-2-yl]carbonyl}-4-oxo-spiro[chromane-2,4'-piperidin]-6-yl) nicotinic acid methyl ester instead of 3-{1'-[(1-cyclopropyl-5-methoxy-isoquinolin-7-yl)carbonyl]-4-oxospiro [chroman-2,4'-piperidin]-6-yl}benzoic acid methyl ester. $^1$H-NMR (400 MHz, DMSO-d$_6$) δ: 9.08 (1H, d, J=2.2 Hz), 9.02 (1H, d, J=2.2 Hz), 8.41 (1H, dd, J=2.2, 2.2 Hz), 8.07-8.02 (3H, m), 7.49 (1H, dd, J=7.8, 7.8 Hz), 7.29-7.23 (2H, m), 7.18 (1H, s), 5.04 (1H, br s), 4.37-4.28 (3H, m), 3.90-3.82 (3H, m), 3.57-3.46 (1H, m), 3.37-3.27 (1H, m), 3.11-3.04 (1H, m), 2.98 (2H, s), 2.13-1.73 (4H, m), 1.09-1.05 (2H, m), 0.87-0.73 (2H, m). MS [M+H]+=594.

EXAMPLE 84

4-(1'-{[8-cyclopropyl-4-(2-hydroxyethoxy)quinolin-2-yl]carbonyl}-4-oxo-spiro[chromane-2,4'-piperidin]-6-yl)pyridine-2-carboxylic acid

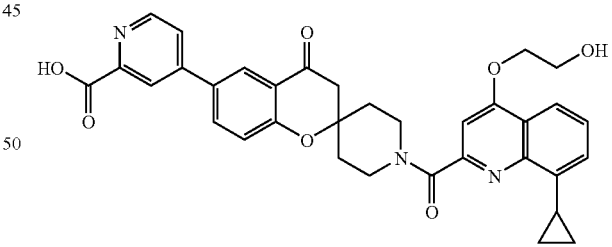

The compound was prepared according to Example 40 but using 4-(1'-{[8-cyclopropyl-4-(2-hydroxyethoxy)quinolin-2-yl]carbonyl}-4-oxo-spiro[chromane-2,4'-piperidin]-6-yl) pyridine-2-carboxylic acid methyl ester instead of 3-{1'-[(1-cyclopropyl-5-methoxy-isoquinolin-7-yl)carbonyl]-4-oxospiro[chroman-2,4'-piperidin]-6-yl}benzoic acid methyl ester. $^1$H-NMR (400 MHz, DMSO-d$_6$) δ: 8.71 (1H, d, J=5.1 Hz), 8.26-8.23 (1H, br m), 8.14-8.12 (2H, br m), 8.04 (1H, d, J=8.3 Hz), 7.93 (1H, d, J=5.1 Hz), 7.51-7.46 (1H, m), 7.30 (1H, d, J=9.0 Hz), 7.24 (1H, d, J=7.3 Hz), 7.18 (1H, s), 5.04 (1H, br s), 4.39-4.31 (1H, m), 4.31-4.26 (2H, m), 3.89-3.82 (3H, br a m), 3.63-3.41 (1H, m), 3.42-3.19 (1H, m), 3.12-3.03

(1H, m), 2.99 (2H, s), 2.17-1.72 (4H, m), 1.10-1.02 (2H, m), 0.87-0.72 (2H, m). MS [M+H]+=594.

EXAMPLE 85

6-tert-butyl-1'-[(4,8-dimethoxyquinolin-2-yl)carbonyl]spiro[chromane-2,4'-piperidin]-4(3H)-one

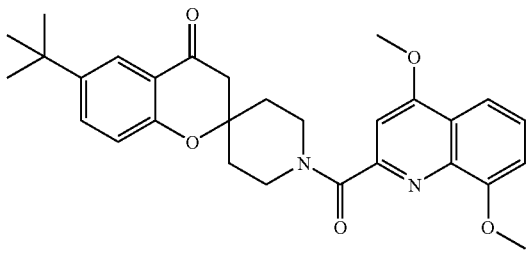

The compound was prepared according to Example 1 but using 6-tert-butylspiro[chromene-2,4'-piperidin]-4(3H)-one TFA salt and 4,8-dimethoxyquinoline-2-carboxylic acid instead of 4-oxospiro[chroman-2,4'-piperidin]-6-ylacetamide TFA salt and 4-methoxyquinoline-2-carboxylic acid. $^1$H-NMR (400 MHz, CDCl$_3$) δ: 7.87 (1H, d, J=2.7 Hz), 7.77 (11H, dd, J=8.5, 1.2 Hz), 7.56 (1H, dd, J=8.7, 2.6 Hz), 7.46 (1H, dd, J=8.3, 7.8 Hz), 7.18 (1H, s), 7.07 (1H, dd, J=7.8, 1.0 Hz), 6.95 (1H, d, J=8.5 Hz), 4.62-4.54 (1H, m), 4.19-4.08 (1H, m), 4.08 (3H, s), 4.03 (3H, s), 3.68-3.56 (1H, m), 3.42-3.33 (1H, m), 2.84-2.69 (2H, m), 2.25-2.17 (1H, m), 2.10-2.02 (1H, m), 1.91-1.82 (2H, m), 1.29 (9H, s). MS [M+H]+=489.

REFERENCE EXAMPLE 1

N-{4-oxospiro[chroman-2,4'-piperidin]-6-yl}acetamide TFA Salt

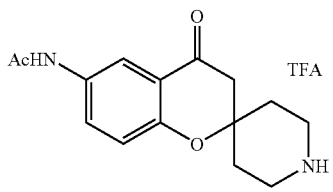

A mixture of 24.8 g of 4-methoxyacetanilide, 37.3 mL of acetyl chloride and 250 mL of CH$_2$Cl$_2$ was refluxed until the insoluble solid was dissolved, and then cooled to 0° C. 70.0 g of AlCl$_3$ was gradually added thereto, and then the mixture was heated under reflux for 5 hours. The reaction mixture was poured into 500 mL of water with ice, and stirred for 30 minutes. The resulting precipitate was collected through filtration, washed with water and dried under vacuum to obtain 23.5 g of 5-acetylamino-2-hydroxyacetophenone. 9.96 g of N-Boc-piperidin-4-one, 4.17 mL of pyrrolidine and 75 mL of MeOH were added to 9.66 g of the product, and heated under reflux for 13 hours. The reaction mixture was concentrated, cold MeOH was added to the residue, and the insoluble solid was taken out through filtration and dried under vacuum to obtain 16.3 g of N-{1'-[(tert-butoxy)carbonyl]-4-oxospiro[chroman-2,4'-piperidin]-6-yl}acetamide. TFA (43 mL) cooled at 0° C. was gradually added to 16.1 g of the product, and stirred at room temperature for 1 hour. The reaction mixture was concentrated, and TFA still remaining therein was removed through codistillation with toluene added thereto, and 50 mL of Et$_2$O was added to the residue. The resulting insoluble solid was taken out through filtration, washed with Et$_2$O/EtOAc (1/2), and dried under vacuum to obtain N-{4-oxospiro[chroman-2,4'-piperidin]-6-yl}acetamide TFA salt.

REFERENCE EXAMPLE 2

4,8-Dimethoxyquinoline-2-carboxylic Acid 145.6 g of dimethyl acetylenedicarboxylate was dropwise added to a solution of 123.15 g of 2-methoxyaniline in MeOH (600 mL) at 0° C. over 30 minutes. The mixture was stirred at room temperature overnight, and the resulting solution was added to 700 mL of Ph$_2$O heated at 235° C. (inner temperature) over 30 minutes. This was then heated for an additional 30 minutes. After cooled to room temperature, the reaction mixture was diluted with 700 mL of toluene and 700 mL of n-hexane, and stirred at 0° C. for 3 hours. The resulting precipitate was taken out through filtration, washed with MeOH, and 134 g of 4-hydroxy-8-methoxyquinoline-2-carboxylic acid methyl ester was obtained as an off-white solid.

19.76 g of potassium carbonate and 100 mL of DMF were added to 22.2 g of the product, and then 8.90 mL of methyl iodide was added thereto and stirred overnight at room temperature. The reaction mixture was diluted with 200 mL of water, and stirred at 0° C. for 1 hour. The resulting precipitate was taken out through filtration, and dried in vacuum at 70° C. to obtain 21.0 g of 4,8-dimethoxyquinoline-2-carboxylic acid methyl ester.

15.3 g of the product was dissolved in 400 mL of MeOH, and 24.7 mL of 5 N NaOHaq was dropwise added thereto at 0° C., and the mixture was stirred overnight at room temperature. This was cooled to 0° C., and 20.7 mL of 6 N HClaq was dropwise added thereto, and the reaction solution was concentrated. Water and mixed chloroform/MeOH were added to the residue, and shaken, and the organic layer was separated and dried on sodium sulfate. After concentrated, MeOH and n-hexane were added to the residue, and the insoluble solid was taken out through filtration to obtain the intended compound as a pale yellow solid.

REFERENCE EXAMPLE 3

6-bromo-1'-(tert-butoxycarbonyl)spiro[chroman-2,4'-piperidin]-4-one 60 mL of MeOH, 7.97 g of N-Boc-piperidin-4-one, and 3.34 mL of pyrrolidine were added to 8.60 g of 5-bromo-2-hydroxyacetophenone put in a 200-mL flask equipped with a condenser, and the mixture was overnight heated under reflux. The reaction mixture was cooled to room temperature, and concentrated. The residue was purified through silica gel column chromatography (eluted with n-hexane/EtOAc=6/1) to obtain the intended compound as a pale yellow solid.

REFERENCE EXAMPLE 4

6-bromospiro[chroman-2,4'-piperidin]-4-one hydrochloride

A mixture of 25.0 g of 5-bromo-2-hydroxyacetophenone, 25.0 g of N-Boc-piperidin-4-one, 9.68 mL of pyrrolidine and 250 mL of MeOH was heated under reflux overnight. The reaction mixture was cooled to room temperature and concentrated. The residue was put into 300 mL of 1,4-dioxane, and 100 mL of concentrated hydrochloric acid was added thereto and stirred at room temperature for 4 hour. The reaction solution was poured into water, and stirred overnight. The resulting precipitate was taken out through filtration, washed with water and n-hexane, and dried under reduced pressure to obtain the intended compound as an yellow solid.

REFERENCE EXAMPLE 5 tert-butyl 6-cyano-4-oxospiro[chroman-2,4'-piperidine]-1'-carboxylate

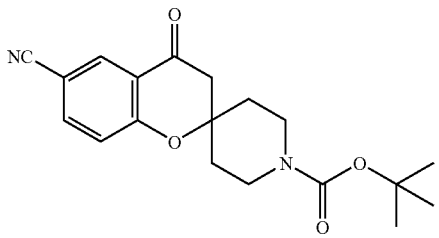

A mixture of tert-butyl 6-bromo-4-oxospiro[chroman-2,4'-piperidine]-1'-carboxylate (143 g, 0.36 mol), $Zn(CN)_2$ (84.7 g, 0.72 mol), $Pd(PPh_3)_4$ (20 g, 17 mmol) and dry DMF (1 liter) was stirred under an argon atmosphere at 90° C. for 6 hours. The resulting mixture was, after cooled, diluted with ethyl acetate (1 liter), and washed with aqueous 12% ammonia, water, and saturated brine in order. The organic layer was dried over sodium sulfate, and concentrated, and the residue was treated with methanol, and the resulting insoluble solid was taken out through filtration, and dried under a reduced pressure to obtain tert-butyl 6-cyano-4-oxospiro[chroman-2,4'-piperidine]-1'-carboxylate as a colorless solid.

REFERENCE EXAMPLE 6 tert-butyl 4-oxo-6-(1H-tetrazol-5-yl)spiro[chroman-2,4'-piperidine]-1'-carboxylate

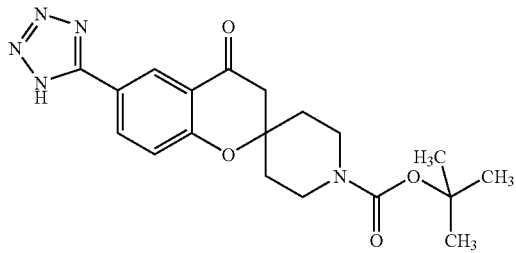

67.5 g of sodium azide, 143 g of triethylamine hydrochloride, and 1.2 liters of dry DMF were added to the cyano compound (119 g) produced in Reference Example 5, and the mixture was stirred under a nitrogen atmosphere at 100° C. for 12 hours. After cooled, the reaction mixture was partitioned between 1 N hydrochloric acid (200 mL), water and ethyl acetate. The aqueous layer was further extracted three times with ethyl acetate, and the combined organic layers were washed with water and brine, dried over sodium sulfate and concentrated. The residue was triturated with methanol, and the insoluble solid was collected through filtration and dried under reduced pressure to obtain tert-butyl 4-oxo-6-(1H-tetrazol-5-yl)spiro[chroman-2,4'-piperidine]-1'-carboxylate as a colorless solid.

REFERENCE EXAMPLE 7

6-(1H-tetrazol-5-yl)spiro[chroman-2,4'-piperidine]-4-one

4 N HCl-1,4-dioxane (200 mL) was added to 40.6 g tert-butyl 4-oxo-6-(1H-tetrazol-5-yl)spiro[chroman-2,4'-piperidine]-1'-carboxylate produced in Reference Example 6, and stirred at room temperature for 5 hours. The reaction mixture was concentrated, and the residue was triturated with methanol. The insoluble solid was collected through filtration, and dried under reduced pressure to obtain 6-(1H-tetrazol-5-yl)-spiro[chroman-2,4'-piperidine]-4-one as a colorless solid.

REFERENCE EXAMPLE 8

1'-[(4,8-dimethoxyquinolin-2-yl)carbonyl]-6-(4,4,5,5-tetramethyl-1,3,2-dioxaborolan-2-yl)spiro[chroman-2,4'-piperidin]-4-one

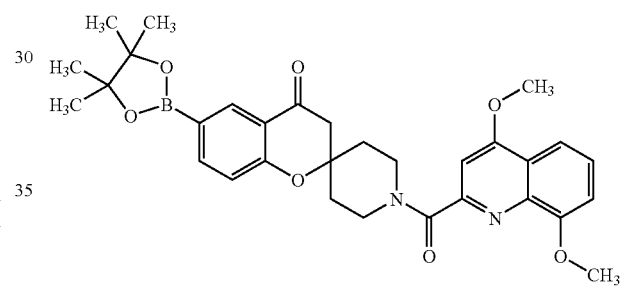

1.09 g of 4,4,4',4',5,5,5',5'-octamethyl-2,2'-bi-1,3,2-dioxaborolane, 319 mg of $PdCl_2(dppf)$, 433 mg of DPPF and 418 mg of KOAc were added to 6-bromo-1'-[(4,8-dimethoxyquinolin-2-yl)carbonyl]-spiro[chroman-2,4'-piperidin]-4-one (2.00 g) obtained in Example 9, and heated in 1,4-dioxane at 100° C. After cooled, the reaction solution was concentrated and partitioned between $CHCl_3$ and water. The organic layer was washed with saturated brine, and dried over magnesium sulfate, and the solvent was evaporated. The resulting residue was purified through silica gel column chromatography (n-hexane/AcOEt=–8/2, 1/1) to obtain the intended compound.

REFERENCE EXAMPLE 9

Methyl 4,8-dimethoxyquinoline-2-carboxylate 400 mL of DMF and 34.55 g (250 mmol) of $K_2CO_3$ was added to 10.26 g (50.0 mmol) of xanthurenic acid placed in a 1 L-flask at room temperature, and then 18.7 mL (300 mmol) of $CH_3I$ was added thereto. The mixture was stirred overnight at room temperature. The mixture was concentrated in vacuo, and partitioned between 0.8 L of EtOAc and 0.3 L of $H_2O$. The aqueous layer was extracted with EtOAc (0.8 L). The organic layers were combined, dried over $Na_2SO_4$, and concentrated. The residue was triturated with 50 mL of $Et_2O$ at room temperature. The insoluble material was collected, washed with Et$_2$O, and dried in vacuo to afford methyl 4,8-dimethoxyquinoline-2-carboxylate as a pale brown powder.

REFERENCE EXAMPLE 10

Methyl 4-hydroxy-8-cyclopropylquinoline-2-carboxylate

A solution of 21.8 mL of acetylenedicarboxylate (0.18 mol) in 50 mL of MeOH was added dropwise to a solution of 22.5 g of 2-cyclopropylaniline (0.17 mol) in 150 mL of MeOH over 1 hr and the mixture was stirred at room temperature for 2 hr. The reaction mixture was concentrated and the residue was taken up into 30 mL of diphenyl ether. The solution was added dropwise to 200 mL of diphenyl ether heated at 250 C and the mixture was stirred at the temperature for 30 min. The reaction mixture was concentrated in vacuo and the residue was purified on a SiO$_2$ column chromatography (eluted with n-Hex/AcOEt=1/1) to give methyl 4-hydroxy-8-cyclopropylquinoline-2-carboxylate as a pale yellow solid.

REFERENCE EXAMPLE 11

Methyl 4-ethoxy-8-cyclopropylquinoline-2-carboxylate

To a stirred solution of 1.04 g (4.28 mmol) of methyl 4-hydroxy-8-cyclopropylquinoline-2-carboxylate in 11 mL of DMF was added 1.18 g of K$_2$CO$_3$ and 0.68 mL of ethyl iodide successively and the mixture was stirred at 60 deg C. for 12 hr. The mixture was partitioned between AcOEt and H$_2$O and the organic layer was washed with H$_2$O and satd. brine, dried over anhydrous Na$_2$SO$_4$, and then concentrated. The residue was purified on SiO$_2$ column chromatography (eluted with n-Hex/AcOEt=19/1) to yield methyl 4-ethoxy-8-cyclopropylquinoline-2-carboxylate as a pale yellow solid.

REFERENCE EXAMPLE 12

4-ethoxy-8-cyclopropylquinoline-2-carboxylic Acid 2.0 mL of 5N NaOHaq was added to a solution of 1.10 g of methyl 4-ethoxy-8-cyclopropylquinoline-2-carboxylate in 5 mL of CHCl$_3$/MeOH (1:1) and the mixture was stirred at room temperature for 3 hr. After the addition of 3.0 mL of 5N HCl aq, the mixture was extracted by CHCl$_3$. The organic layer was washed by satd. brine, dried over NaSO$_4$, then concentrated to afford 4-ethoxy-8-cyclopropylquinoline-2-carboxylic acid as a colorless solid.

REFERENCE EXAMPLE 13

4-methoxy-8-cyclopropylquinoline-2-carboxylic Acid

The compound was prepared according to the procedures described in the reference Example 12 and 13, using methyl iodide instead of ethyl iodide.

REFERENCE EXAMPLE 14

5-Bromo-nicotinic acid tert-butyl ester

5-Bromo-nicotinic acid (20.2 g, 100 mmol) was dissolved in CHCl$_3$ (200 mL) and tert-BuOH (40 mL); and WSC (21.1 g, 110 mmol) and DMAP (21.1 g, 110 mmol) was added thereto in order, and stirred at room temperature over night. The reaction mixture was diluted with chloroform, washed with 0.5N HCl aq. (220 mL), 0.5N NaOH aq. (100 mL), brine and dried over MgSO$_4$ and silica gel. After filtration, the solvents were removed in vacuo to afford 5-Bromo-nicotinic acid tert-butyl ester as a colorless solid. This solid was used for the next step without further purification.

REFERENCE EXAMPLE 15

5-{1'-tert-butoxycarbonyl]-4-oxospiro[chroman-2,4'-piperidin]-6-yl}nicotinic acid tert-butyl ester tert-butyl-6-bromo-4-oxospiro[chroman-2,4'-piperidine]-1'-carboxylate (19.8 g, 50.0 mmol), bis(pinacolato)diboran (14.0 g, 55.0 mmol), Pd(OAc)$_2$ (560 mg, 2.50 mmol), DPPF (2.77 g, 5.00 mmol), and AcOK (5.82 g, 60.0 mmol) were suspended in dioxane (250 mL) and heated at 100° C. for 10 hours. After cooling down to room temperature, 5-bromo-nicotinicacid tert-butyl ester (14.2 g, 55.0 mmol), Pd(PPh$_3$)$_4$ (5.78 g, 5.00 mmol) and 2M Na$_2$CO$_3$ aq. (125 mL, 250 mmol) were added to the reaction mixture; and then heated at 100° C. for 15 hours. The reaction mixture was diluted with EtOAc and H$_2$O, organic layer was washed with brine and dried over MgSO$_4$. After filtration, the solvents were removed in vacuo and the residue was purified by silica gel column chromatography (hexane/EtOAc=10/0 to 6/4) and the obtained brown solid was crystallized from EtOAc/hexane (1/1) to afford 5-{1'-tert-butoxycarbonyl]-4-oxospiro[chroman-2,4'-piperidin]-6-yl}nicotinic acid tert-butyl ester as a pale yellow solid.

REFERENCE EXAMPLE 16

5-{4-oxospiro[chroman-2,4'-piperidin]-6-yl}nicotinic Acid Di-Hydrochloride

5-{1'-tert-butoxycarbonyl]-4-oxospiro[chroman-2,4'-piperidin]-6-yl}nicotinic acid tert-butyl ester (14.0 g, 28.3 mmol) was dissolved in CHCl$_3$ (70 mL) and 4N HCl in dioxane (210 mL) was added thereto, and stirred at room temperature for 20 h. The resulted precipitate was filtered and washed with CHCl$_3$ and Et$_2$O to afford 5-{4-oxospiro[chroman-2,4'-piperidin]-6-yl}nicotinic acid di-hydrochloride as a colorless solid.

REFERENCE EXAMPLE 17

(8-Cyclopropyl-4-methoxy-quinolin-2-yl)imidazol-1-yl-methanone

8-Cyclopropyl-4-methoxy-quinoline-2-carboxylic acid (2.70 g, 11.1 mmol) was dissolved in DMF (27 mL) and carbonyldiimidazole (2.33 g, 14.4 mmol) was added thereto portionwise. After the mixture was stirred at room temperature for 4 h, H$_2$O (135 mL) was added dropwise thereto at 0° C. for 1 h. The resulted precipitate was filtered and washed with H$_2$O to afford (8-cyclopropyl-4-methoxy-quinolin-2-yl)-imidazol-1-yl-methanone as a colorless solid.

REFERENCE EXAMPLE 18 tert-butyl 6-cyano-4-hydroxy-3,4-dihydro-1'H-spiro[chromene-2,4'-piperidine]-1'-carboxylate To a solution of 15 g of tert-butyl 6-cyano-3,4-dihydro-4-oxospiro[chromene-2,4'-piperidine]-1'-carboxylate in 250 mL of EtOH-THF(1:4) at 0° C. was added NaBH$_4$ portionwise, and the reaction mixture was allowed to warm up to rt. After stirring for 1 h, NH₄Claq was added to the reaction mixture and the aqueous mixture was extracted with AcOEt twice. The combined organic layers were washed with brine, dried over Na₂SO₄, filtered, and concentrated in reduced pressure to give the intended compound as a pale yellow solid.

REFERENCE EXAMPLE 19 tert-butyl 4-{[tert-butyl(dimethyl)silyl]oxy}-6-cyano-3,4-dihydro-1'H-spiro[chromene-2,4'-piperidine]-1'-carboxylate To a solution of 15.1 g of tert-butyl 6-cyano-4-hydroxy-3,4-dihydro-1'H-spiro[chromene-2,4'-piperidine]-1'-carboxylate in DMF were added 3.6 g of imidazole and 7.95 g of TBSCl at rt, and the reaction mixture was stirred at rt for 1d. To this reaction mixture was added 598 mg of imidazole and 1.3 g of TBSCl at rt, and the reaction mixture was stirred at rt for 1d. The reaction mixture was poured into ice-cold brine, and the aqueous mixture was extracted with AcOEt twice. The combined organic layers were washed with H₂O and brine, dried over Na₂SO₄, filtered, and concentrated in reduced pressure. The residue was purified by column chromatography on silica gel using a mixture of hexane and AcOEt (100/0-80/20) as eluent to give the intended compound.

REFERENCE EXAMPLE 20 tert-butyl 6-[amino(hydroxyimino)methyl]-4-{[tert-butyl(dimethyl)silyl]oxy}-3,4-dihydro-1'H-spiro[chromene-2,4'-piperidine]-1'-carboxylate To a suspension of 18.2 g of tert-butyl 4-{[tert-butyl(dimethyl)silyl]oxy}-6-cyano-3,4-dihydro-1'H-spiro[chromene-2,4'-piperidine]-1'-carboxylate in EtOH was added 16.3 mL of Et₃N and 8.12 g of hydroxyamine hydrochloride at rt, and the reaction mixture was stirred at 85° C. for 1d. The resultant solution was cooled to rt, and concentrated in reduced pressure. To the residue was added H₂O, the resultant white solid was filtered, washed with H₂O, and dried in vacuo to give a crude product, which was used in the next step without further purification.

REFERENCE EXAMPLE 21 tert-butyl 6-{amino[({[(2-ethylhexyl)oxy]carbonyl}oxy)-imino]methyl}-4-{[tert-butyl(dimethyl)silyl]oxy}-3,4-dihydro-1'H-spiro[chromene-2,4'-piperidine]-1'-carboxylate To a solution of tert-butyl 6-[amino(hydroxyimino)methyl]-4-{[tert-butyl(dimethyl)silyl]oxy}-3,4-dihydro-1'H-spiro[chromene-2,4'-piperidine]-1'-carboxylate in 80 mL of DMF were added 3.78 mL of pyridine and 8.4 mL of 2-Ethylhexyl chloroformate at 0° C., and the reaction mixture was stirred at 0° C. for 1.5 h. The reaction mixture was poured into ice-cold brine, and extracted with AcOEt twice. The combined organic layers were washed with H₂O and brine, dried over Na₂SO₄, filtered, and concentrated in reduced pressure to give a crude product, which was used in the next step without further purification.

REFERENCE EXAMPLE 22 tert-butyl 4-{[tert-butyl(dimethyl)silyl]oxy}-6-(5-oxo-4,5-dihydro-1,2,4-oxadiazol-3-yl)-3,4-dihydro-1'H-spiro[chromene-2,4'-piperidine]-1'-carboxylate A solution of tert-butyl 6-{amino[({[(2-ethylhexyl)oxy]carbonyl}oxy)imino]methyl}-4-{[tert-butyl(dimethyl)silyl]oxy}-3,4-dihydro-1'H-spiro[chromene-2,4'-piperidine]-1'-carboxylate in 100 mL of xylene was stirred at 145° C. for 14 h. The reaction mixture was cooled to rt, and concentrated in reduced pressure. The residue was purified by column chromatography on silica gel using a mixture of hexane-AcOEt (100/1-35/65) as an eluent to give the product as an off-white solid.

REFERENCE EXAMPLE 23 tert-butyl 4-hydroxy-6-(5-oxo-4,5-dihydro-1,2,4-oxadiazol-3-yl)-3,4-dihydro-1'H-spiro[chromene-2,4'-piperidine]-1'-carboxylate To a solution of 13.4 g of tert-butyl 4-{[tert-butyl(dimethyl)silyl]oxy}-6-(5-oxo-4,5-dihydro-1,2,4-oxadiazol-3-yl)-3,4-dihydro-1'H-spiro[chromene-2,4'-piperidine]-1'-carboxylate in 200 mL of EtOH-THF (5.5:1) at 0° C. was added 67 ml Of 1M HClaq dropwise, and the reaction mixture was stirred at rt for 18 h. The reaction mixture was cooled to 0° C., and the mixture was basified with NaHCO₃. The mixture was concentrated in reduced pressure, and the residue was acidified with 1M HClaq. The aqueous mixture was extracted with a mixture of CHCl₃-MeOH (9:1) three times, and the combined organic layers was washed with brine, dried over Na₂SO₄, and concentrated in reduces pressure to give the product as a pale brown solid.

REFERENCE EXAMPLE 24 tert-butyl 4-oxo-6-(5-oxo-4,5-dihydro-1,2,4-oxadiazol-3-yl)-3,4-dihydro-1'H-spiro[chromene-2,4'-piperidine]-1'-carboxylate To a solution of 1.0 g of tert-butyl 4-hydroxy-6-(5-oxo-4,5-dihydro-1,2,4-oxadiazol-3-yl)-3,4-dihydro-1'H-spiro[chromene-2,4'-piperidine]-1'-carboxylate in 40 ml of THF-CH₃CN (1:1) ar rt were added 2.0 g of MS 4A, 435 mg of NMO, and 88 mg of TPAP, and the reaction mixture was stirred at rt overnight. The mixture was filtered through a Celite pad, washed with CHCl₃ and CHCl₃-MeOH (9:1), and the filtrate was concentrated in reduced pressure. The residue was purified by column chromatography on silica gel using a mixture of hexane-AcOEt (100/0-0/100) as eluent to give the intended compound as a colorless solid.

REFERENCE EXAMPLE 25

6-(5-oxo-4,5-dihydro-1,2,4-oxadiazol-3-yl)spiro[chromene-2,4'-piperidin]-4(3H)-one hydrochloride A suspension of 437 mg of tert-butyl 4-oxo-6-(5-oxo-4,5-dihydro-1,2,4-oxadiazol-3-yl)-3,4-dihydro-1'H-spiro[chromene-2,4'-piperidine]-1'-carboxylate in 10 mL of 4N HCl in dioxane was stirred at rt for 1d, the resultant white solid was filtered, and washed with ether. The collected white solid was dried in vacuo at 50° C. to give the intended compound as a colorless solid.

REFERENCE EXAMPLE 26

1'-tert-butoxycarbonyl-6-(4",4",5",5"-tetramethyl-1", 3",2"-dioxaborolan-2"-yl) spiro[chroman-2,4'-piperidin]-4-one tert-Butyl-6-bromo-4-oxospiro[chroman-2,4'-piperidine]-1'-carboxylate (99.0 g, 250 mmol), bis(pinacolato)diboran (70.2 g, 275 mmol), Pd(OAc)$_2$ (2.80 g, 12.5 mmol), DPPF (13.9 g, 25.0 mmol), and AcOK (29.1 g, 300 mmol) were suspended in dioxane (500 ml) and heated at 100° C. for 20 h. After cooling down to room temperature, MeOH (500 ml) was added and further stirred for 1 h. The resulted precipitate was filtered and the cake was washed with MeOH to obtain the intended compound as a pale brown solid.

REFERENCE EXAMPLE 27

5"-{1'-tert-butoxycarbonyl]-4-oxospiro[chroman-2,4'-piperidin]-6-yl}nicotinic Acid Methyl Ester 1'-tert-butoxycarbonyl-6-(4",4",5",5"-tetramethyl-1",3",2"-dioxaborolan-2"-yl)spiro[chroman-2,4'-piperidin]-4-one (2.00 g, 4.51 mmol), 5-bromonicotinic acid methyl ester (1.17 g, 5.42 mmol), Pd(OAc)$_2$ (50.6 mg, 0.226 mmol), DPPF (250 g, 0.451 mmol), and K$_3$PO$_4$ (1.91 g, 9.02 mmol) were suspended in DME (500 ml) and heated at 100° C. for 18 h. The reaction mixture was filtered through Celite, the residue on the Celite was washed with chloroform, and the filtrate and the washing were combined and concentrated under a reduced pressure. The resulting residue was purified through silica gel column chromatography (hexane/EtOAc=10/0 to 2/8) to obtain the intended compound as a pale yellow foam.

REFERENCE EXAMPLE 28

5"-{4-oxospiro[chroman-2,4'-piperidin]-6-yl}nicotinic Acid Methyl Ester Di-Hydrochloride 5"-{1'-tert-butoxycarbonyl]-4-oxospiro[chroman-2,4'-piperidin]-6-yl}nicotinic acid methyl ester (22.0 g, 48.6 mmol) was suspended in MeOH (110 ml) and 4N HCl in dioxane (220 ml) was added thereto, and stirred at room temperature for 14 h. The solvents were removed in vacuo and the resulting solid was washed with MeOH/Et$_2$O (50 ml/200 ml) to obtain the intended compound as a colorless solid.

REFERENCE EXAMPLE 29

2-cyclopropyl-3-cyano-pyridine

2-Chloro-3-cyano-pyridine (9.69 g, 70.0 mmol), cyclopropylboronic acid (7.21 g, 84.0 mmol), Pd(OAc)$_2$ (875 mg, 3.50 mmol), tricyclohexylphosphine (1.96 g, 7.00 mmol), and K$_3$PO$_4$ (44.5 g, 210 mmol) were suspended in toluene (280 ml) and H$_2$O (14 ml) and heated at 100° C. for 5 h. The reaction mixture was dried over MgSO$_4$ and the mixture was filtered through Celite, the filtrate was concentrated under reduced pressure. The resulting residue was purified by silica gel column chromatography (hexane/EtOAc=10/0 to 7/3) to obtain the intended compound as a pale yellow solid.

REFERENCE EXAMPLE 30

2-cyclopropyl-3-pyridinecarboxaldehyde 2-cyclopropyl-3-cyano-pyridine (18.5 g, 128 mmol) was dissolved in toluene (400 ml) and DIBAL (1.01M in toluene, 153 ml) was added thereto at 0° C. After stirred at 0° C. for 1 h, the reaction mixture was poured into 2N HCl aq (90 ml); and 5N NaOH aq. (40 ml) was added thereto. The mixture was extracted with EtOAc and the organic layer was washed with brine, dried over MgSO$_4$. The desiccant was removed through filtration, the filtrate was concentrated under reduced pressure, and the resulting residue was purified by silica gel column chromatography (hexane/EtOAc=10/0 to 7/3) to obtain the intended compound as a pale yellow solid.

REFERENCE EXAMPLE 31

2-[1-(2-Cyclopropyl-pyridin-3-yl)-methylidene]-succinic Acid 4-tert-butyl-1-methyl Diester Triphenylphosphoranylidene-butanedioicacid-4-tert-butyl-1-methyl ester (53.8 g, 120 mmol) was dissolved in toluene (300 ml) and 2-cyclopropyl-3-pyridinecarboxaldehyde (11.0 g, 74.7 mmol) was added thereto. After the reaction mixture was stirred at 120° C. for 14 h, the solvent was removed in a reduced pressure. The resulting solid was washed with hexane/EtOAc (90 ml/270 ml) and the filtrate was concentrated in vacuo. The resulting residue was purified by silica gel column chromatography (hexane/EtOAc=10/0 to 7/3) to obtain the intended compound as a pale yellow oil.

REFERENCE EXAMPLE 32

2-[1-(2-Cyclopropyl-pyridin-3-yl)-methylidene]-succinic acid 1-methyl Ester

Formic acid (200 ml) was added to 2-[1-(2-cyclopropyl-pyridin-3-yl)-methylidene]-succinic acid 4-tert-butyl-1-methyl diester (22.0 g, 69.4 mmol) and the mixture was stirred at 50° C. for 4 days. After removal of formic acid in vacuo, the resulting residue was purified by silica gel column chromatography (CHCl$_3$/MeOH=100/0 to 88/12) to obtain the intended compound as a pale yellow oil.

REFERENCE EXAMPLE 33

5-Acetoxy-1-cyclopropyl-isoquinoline-7-carboxylic Acid Methyl Ester

2-[1-(2-Cyclopropyl-pyridin-3-yl)-methylidene]-succinic acid 1-methyl ester (18.9 g, 72.4 mmol), sodium acetate (5.94 g, 72.4 mmol) was suspended in AcOH (150 ml) and heated at 155° C. for 6 h. After cooling to room temperature, the mixture was concentrated in vacuo. The residue was purified by silica gel column chromatography (hexane/EtOAc=10/0 to 6/4) to obtain the intended compound as a pale yellow solid.

REFERENCE EXAMPLE 34

1-Cyclopropyl-5-hydroxy-isoquinoline-7-carboxylic Acid Methyl Ester

5-Acetoxy-1-cyclopropyl-isoquinoline-7-carboxylic acid methyl ester (12.7 g, 44.6 mmol) was dissolved in THF (90 ml)-MeOH (30 ml) and K$_2$CO$_3$ (3.69 g, 26.7 mmol) was added thereto. After stirring at room temperature for 20 h, the reaction mixture was diluted with EtOAc and diluted HCl aq. (26.7 mmol). The mixture was extracted with EtOAc and the organic layer was washed with brine, dried over MgSO$_4$. The desiccant was removed through filtration and the filtrate was concentrated under reduced pressure. The residue was triturated with EtOAc and hexane (1:2) and the insoluble solid was collected through filtration to obtain the intended compound as a colorless solid.

REFERENCE EXAMPLE 35

1-Cyclopropyl-5-methoxy-isoquinoline-7-carboxylic Acid Methyl Ester

1-Cyclopropyl-5-hydroxy-isoquinoline-7-carboxylic acid methyl ester (5.00 g, 20.6 mmol) was dissolved in DMF (50 ml) and $K_2CO_3$ (5.69 g, 41.2 mmol) and MeI (1.54 ml, 24.7 mmol) was added thereto. After stirred at room temperature for 2 h, the reaction mixture was diluted with EtOAc and $H_2O$. The aqueous layer was extracted with EtOAc and the organic layer was washed with brine, dried over $MgSO_4$. The desiccant was removed through filtration and the filtrate was concentrated under reduced pressure. The residue was purified by silica gel column chromatography (hexane/EtOAc=10/0 to 6/4) to obtain the intended compound as a colorless solid.

REFERENCE EXAMPLE 36

1-Cyclopropyl-5-methoxy-isoquinoline-7-carboxylic Acid

1-Cyclopropyl-5-methoxy-isoquinoline-7-carboxylic acid methyl ester (4.87 g, 18.9 mmol) was dissolved in THF (50 ml) and MeOH (50 ml), and 5N NaOH aq. (18.9 ml) was added thereto. After stirred at 60° C. for 2 h, the mixture was concentrated in vacuo. The residue was triturated with $H_2O$ and 5N HCl aq. (18.9 ml) and the insoluble solid was collected through filtration to obtain the intended compound as a colorless solid.

REFERENCE EXAMPLE 37

5"-{1'-[(1-Cyclopropyl-5-methoxy-isoquinolin-7-yl)carbonyl]-4-oxospiro[chroman-2,4'-piperidin]-6-yl}nicotinic Acid Methyl Ester 1-Cyclopropyl-5-methoxy-isoquinoline-7-carboxylic acid (900 mg, 3.70 mmol), 5"-{4-oxospiro[chroman-2,4'-piperidin]-6-yl}nicotinic acid methyl ester di-hydrochloride (1.89 g, 4.44 mmol), EDCI (852 mg, 4.44 mmol), HOBT (675 mg, 4.44 mmol), and TEA (2.06 ml, 14.8 mmol) were suspended in DMF (500 ml) and stirred at room temperature for 16 h. After removal of the solvent, the residue was diluted with $CHCl_3$ and $H_2O$. The aqueous layer was extracted with $CHCl_3$ and the combined organic layer was washed with saturated $NaHCO_3$ aq. and brine, dried over $MgSO_4$. The desiccant was removed through filtration and the filtrate was concentrated under reduced pressure. The residue was purified by silica gel column chromatography (hexane/EtOAc=10/0 to 0/10) to obtain the intended compound as a pale yellow foam.

REFERENCE EXAMPLE 38

3"-{1'-tert-butoxycarbonyl-4-oxospiro[chroman-2,4'-piperidin]-6-yl}benzoic Acid tert-butyl-6-bromo-4-oxospiro[chroman-2,4'-piperidine]-1'-carboxylate (39.6 g, 100 mmol), 3-carboxy-phenylboronic acid (16.6 g, 100 mmol), Pd(PPh$_3$)$_4$ (5.78 g, 5.00 mmol), and 2M $Na_2CO_3$ aq. (250 ml, 500 mmol) were suspended in 1,4-dioxane (400 ml) and heated at 100° C. for 18 h. The reaction mixture was diluted with $CHCl_3$ and dil HCl aq. (1.1 mol), the aqueous layer was extracted with $CHCl_3$. The combined organic layer was washed with $H_2O$ and brine, dried over $MgSO_4$. The desiccant was removed through filtration and the filtrate was concentrated under reduced pressure. The residue was triturated with EtOAc and the insoluble solid was collected through filtration to obtain the intended compound as a colorless solid.

REFERENCE EXAMPLE 39

Methyl 3"-{1'-tert-butoxycarbonyl]-4-oxospiro[chroman-2,4'-piperidin]-6-yl}benzoate 3"-{1'-tert-butoxycarbonyl]-4-oxospiro[chroman-2,4'-piperidin]-6-yl}benzoic acid (24.0 g, 54.9 mmol) was dissolved in $CHCl_3$ (120 ml), and MeOH (24 ml), WSC (15.8 g, 82.4 mmol) and DMAP (10.0 g, 82.4 mmol) was added thereto in this order, and the mixture was stirred at room temperature over night. The reaction mixture was diluted with $CHCl_3$ and diluted HCl aq. (220 mmol). The organic layer was washed with 0.5N NaOH aq., brine and dried over $MgSO_4$ and silica gel. The desiccant was removed through filtration and the filtrate was concentrated under reduced pressure. The residue was triturated with MeOH and the insoluble solid was collected through filtration to obtain the intended compound as a pale yellow solid.

REFERENCE EXAMPLE 40

Methyl 5-{4-oxospiro[chroman-2,4'-piperidin-6-yl}benzoate

The intended compound was produced according to the reference Example 28 but using methyl 3"-{1'-tert-butoxycarbonyl]-4-oxospiro[chroman-2,4'-piperidin]-6-yl}benzoate in place of 5"-{1'-tert-butoxycarbonyl]-4-oxospiro[chroman-2,4'-piperidin]-6-yl}nicotinic acid methyl ester.

REFERENCE EXAMPLE 41

3"-{1'-[(1-Cyclopropyl-5-methoxy-isoquinolin-7-yl)carbonyl]-4-oxospiro[chroman-2,4'-piperidin]-6-yl}benzoic Acid Methyl Ester The intended compound was produced according to the procedure described in reference Example 37 but using methyl 3"-{4-oxospiro[chroman-2,4'-piperidin]-6-yl}benzoate in place of methyl 5"-{4-oxospiro[chroman-2,4'-piperidin]-6-yl}nicotinate di-hydrochloride.

REFERENCE EXAMPLE 42

5"-{1'-tert-butoxycarbonyl]-4-oxospiro[chroman-2,4'-piperidin]-6-yl}nicotinamide The intended compound was produced according to the procedure described in reference Example 27 but using 5-bromonicotinamide in place of 5-bromonicotinic acid methyl ester.

REFERENCE EXAMPLE 43

5"-{4-oxospiro[chroman-2,4'-piperidin]-6-yl}nicotinamide Di-Hydrochloride

The intended compound was produced according to the procedure described in reference Example 28 but using 5"-{1'-tert-butoxycarbonyl]-4-oxospiro[chroman-2,4'-piperidin]-6-yl}nicotinamide in place of 5"-{1'-tert-butoxycarbonyl]-4-oxospiro[chroman-2,4'-piperidin]-6-yl}nicotinic acid methyl ester.

REFERENCE EXAMPLE 44

8-cyclopropyl-4-(2-hydroxy-ethoxy)-[1,7]naphthyridine-2-carboxylic Acid

The intended compound was produced according to the procedures described in reference examples 35 and 36 but using 8-cyclopropyl-4-hydroxy-[1,7]naphthyridine-2-carboxylic acid and acetic acid 2-bromoethyl ester in place of 1-Cyclopropyl-5-hydroxy-isoquinoline-7-carboxylic acid methyl ester and iodomethane.

REFERENCE EXAMPLE 45

6-Carboxy-4-oxospiro(chroman-2,4'-piperidine)hydrochloride tert-butyl 6-cyano-4-oxospiro[chroman-2,4'-piperidine]-1'-carboxylate (20.0 g, 58.5 mmol) was suspended in dioxane (50 ml)-6N HCl aq. (200 ml) and was heated at 120° C. for 20 h. After removal of the solvents in vacuo, the residue was triturated with $H_2O$ and the insoluble solid was collected through filtration to obtain the intended compound as a colorless solid.

REFERENCE EXAMPLE 46 tert-butyl 6-carboxy-4-oxospiro(chroman-2,4'-piperidine)-1'carboxylate

6-Carboxy-4-oxospiro(chroman-2,4'-piperidine) hydrochloride (15.0 g, 50.3 mmol) was dissolved in 1,4-dioxane (150 ml) and $H_2O$ (150 ml), $NaHCO_3$ (10.6 g, 126 mmol) and DIBOC (13.2 g, 60.4 mmol) were added thereto in this order. After stirred at room temperature for 13 h, the reaction mixture was diluted with $Et_2O$ and 5N NaOH aq. (12.1 ml). The aqueous layer was washed with $Et_2O$ and acidified with 6N HCl aq. (PH=ca. 3), then extracted with $CHCl_3$. The organic layer was washed with brine and dried over $MgSO_4$. The desiccant was removed through filtration and the filtrate was concentrated under reduced pressure. The residue was triturated with $MeOH—H_2O$ and the insoluble solid was collected through filtration to obtain the intended compound as a colorless solid.

REFERENCE EXAMPLE 47

1'-tert-butoxycarbonyl-[4-oxospiro(chroman-2,4'-piperidine)-6-yl]-carboxylic acid carbamoylmethyl amide tert-butyl 6-carboxy-4-oxospiro(chroman-2,4'-piperidine)-1'carboxylate (7.50 g, 20.8 mmol), glycinamide hydrochloride (2.76 g, 24.9 mmol), EDCI (4.78 g, 24.9 mmol), HOBT (3.78 g, 24.9 mmol), and TEA (5.80 ml, 41.6 mmol) were suspended in DMF (75 ml) and stirred at room temperature for 23 h. After removal of the solvent, the residue was diluted with EtOAc and $H_2O$. The aqueous layer was extracted with EtOAc and the combined organic layer was washed with saturated $NaHCO_3$ aq. and brine, dried over $MgSO_4$. The desiccant was removed through filtration and the filtrate was concentrated under reduced pressure. The residue was triturated with $MeOH-Et_2O$ and the insoluble solid was collected through filtration to obtain the intended compound as a colorless solid.

REFERENCE EXAMPLE 48

4-oxospiro(chroman-2,4'-piperidine)-6-yl-carboxylicacidcarbamoylmethyl amide hydrochloride The intended compound was produced according to the reference Example 28 but using 1'-tert-butoxycarbonyl-[4-oxospiro(chroman-2,4'-piperidine)-6-yl]-carboxylic acid N-carbamoylmethylamide in place of 5"-{1'-tert-butoxycarbonyl]-4-oxospiro[chroman-2,4'-piperidin]-6-yl}nicotinic acid methyl ester.

REFERENCE EXAMPLE 49

1-Cyclopropyl-5-(2-hydroxy-ethoxy)-isoquinoline-7-carboxylic Acid

The intended compound was produced according to the procedures described in reference examples 35 and 36 but using acetic acid 2-bromoethyl ester in place of iodomethane.

REFERENCE EXAMPLE 50

3-Oxo-4-(2-trimethylsilanyl-ethoxymethyl)-piperazine-1-carboxylic Acid Benzyl Ester Piperazin-2-one (2.00 g, 20.0 mmol) was dissolved in $H_2O$ (10 ml)-1,4-dioxane (10 ml); and $NaHCO_3$ (1.85 g, 22.0 mmol) and benzylchloroformate (3.42 g, 20.0 mmol) was added thereto. After stirring at room temperature for 13 h, the reaction mixture was diluted with $H_2O$ and EtOAc. The aqueous layer was extracted with EtOAc and the combined organic layer was washed with brine, dried over $MgSO_4$. The desiccant was removed through filtration and the filtrate was concentrated under reduced pressure to obtain crude 3-Oxo-piperazine-1-carboxylic acid benzyl ester as pale brown oil. This oil was used for the next step without further purification. The crude 3-Oxo-piperazine-1-carboxylic acid benzyl ester was dissolved in DMF (40 ml) and NaH (55% in oil, 1.05 g, 24.0 mmol) and SEMCl (5.01 g, 30.0 mmol) was added thereto at room temperature. After stirring at 50° C. for 18 h, the reaction mixture was diluted with EtOAc. The mixture was washed with $H_2O$ and brine, dried over $MgSO_4$. The desiccant was removed through filtration and the filtrate was concentrated under reduced pressure. The residue was purified by silica gel column chromatography (hexane/EtOAc=8/2 to 5/5, to obtain the intended compound as a colorless oil.

REFERENCE EXAMPLE 51

1-(2-Trimethylsilanyl-ethoxymethyl)-piperazin-2-one

3-Oxo-4-(2-trimethylsilanyl-ethoxymethyl)-piperazine-1-carboxylic acid benzyl ester (3.00 g, 8.22 mmol) was dissolved in THF (30 ml) and MeOH (30 ml), and vigorously stirred on 20% $Pd(OH)_2/C$ under a hydrogen atmosphere (1 atm) for 14 h. After N2 was purged, $Pd(OH)_2/C$ was removed through filtration and the filtrate was concentrated under reduced pressure. The residue was purified by silica gel column chromatography (CHCl$_3$/MeOH=95/5 to 90/10) to obtain the intended compound as a colorless oil.

REFERENCE EXAMPLE 52

1'-[(4,8-dimethoxyquinolin-2-yl)carbonyl]-6-[(1"-(2"-trimethylsilanyl-ethoxymethyl)piperazin-2"-one-4"-yl)]spiro[chroman-2,4'-piperidin]-4-one 1-(2-Trimethylsilanyl-ethoxymethyl)-piperazin-2-one (540 mg, 2.35 mmol), 6-bromo-'-[(4,8-dimethoxyquinolin-2-yl)carbonyl]spiro[chroman-2,4'-piperidin]-4-one (1.00 g, 1.96 mmol), palladium acetate (43.9 mg, 0.196 mmol), 2-(di-tert-butylphosphino)biphenyl (58.4 mg, 0.196 mmol) and cesium carbonate (766 mg, 2.35 mmol) were suspended in 1,4-dioxane (20 ml), and heated under reflux at 110° C. for 13 h. The reaction mixture was filtered through Celite, the residue on the Celite was washed with chloroform, and the filtrate was concentrated under reduced pressure. The resulting residue was purified by silica gel column chromatography (EtOAc/Acetone=8/2 to 5/5) to obtain the intended compound as a yellow foam.

REFERENCE EXAMPLE 53

1'-[(4,8-dimethoxyquinolin-2-yl)carbonyl]-6-[4-(hydroxymethyl)-3-oxo-piperazin-1-yl)]spiro[chroman-2,4'-piperidin]-4-one 1'-[(4,8-dimethoxyquinolin-2-yl)carbonyl]-6-[(1"-(2"-trimethylsilanyl-ethoxymethyl)-piperazin-2"-one-4"-yl)]spiro[chroman-2,4'-piperidin]-4-one (463 mg, 0.700 mmol) was dissolved in CHCl$_3$ and HF (70% in pyridine, 1.5 ml) was added thereto at 0° C. After stirred at 0° C. for 20 minutes, the reaction mixture was diluted with CHCl$_3$ and 1N NaOH aq. The aqueous layer was extracted with CHCl$_3$ and the combined organic layer was washed with brine, dried over MgSO$_4$. The desiccant was removed through filtration and the filtrate was concentrated under reduced pressure. The residue was purified through silica gel thin-layer chromatography (CHCl$_3$/MeOH=9/1) to obtain the intended compound as a yellow foam.

REFERENCE EXAMPLE 54

Methyl 8-bromo-4-hydroxyquinoline-2-carboxylate 27 ml of dimethyl acetylenedicarboxylate was added to a solution of 34.4 g of 2-bromoaniline in 200 ml of MeOH placed in a 1 L-flask at room temperature. The mixture was stirred overnight at room temperature. The mixture was concentrated in vacuo to afford a yellow oil. The crude product was added to 200 ml of Ph$_2$O placed in 1 L-flask heated at 250° C. The mixture was stirred for 15 min at the same temperature and then cooled to room temperature. 200 ml of toluene and 200 ml of hexane was added to the mixture. The slurry was stirred for 1 h with cooling at 0 deg C. The resulting solid was filtered, washed with hexane, and dried under vacuum to afford methyl 8-bromo-4-hydroxyquinoline-2-carboxylate as an off-white solid.

REFERENCE EXAMPLE 55

Methyl 8-bromo-4-methoxyquinoline-2-carboxylate 400 ml of DMF and 46.9 g of K$_2$CO$_3$ was added to 48.3 g of Methyl 8-bromo-4-hydroxy-2-carboxylate placed in a 1 L-flask at room temperature and then 21.6 ml of MeI was added thereto. The mixture was stirred overnight at room temperature. The mixture was diluted with 800 ml of water; the slurry was cooled in ice bath and stirred for 1 h. The precipitate was filtered, washed with water and dried over under vacuum to afford methyl 8-bromo-4-methoxyquinoline-2-carboxylate as an off-white solid.

REFERENCE EXAMPLE 56

Methyl 8-cyclopropyl-4-methoxyquinoline-2-carboxylate 43.3 g of methyl 8-bromo-4-methoxyquinoline-2-calboxylate, 18.8 g of cyclopropylboronic acid, 46.6 g of K$_3$PO$_4$, 1.63 g of Pd(OAc)$_2$, 4.09 g of tricyclohexylphosphine and 660 ml of toluene were placed in a 2 L-flask and purged with nitrogen gas. The mixture was stirred for 30 min at 100° C., cooled in ice bath and filtered by celite pad. The filtrate was concentrated in vacuo to afford crude brown oil and purified by Biotage Si 75M to afford yellow solid. The solid was washed with hexane 200 ml, and filtered to afford methyl 8-cyclopropyl-4-methoxyquinoline-2-carboxylate as a pale yellow solid.

REFERENCE EXAMPLE 57

8-Cyclopronyl-4-methoxyquinoline-2-carboxylic Acid 30.0 g of methyl 8-cyclopropyl-4-methoxyquinoline-2-carboxylate, 250 ml of THF and 400 ml of MeOH was placed in 2 L-flask, and 46 ml of 5N NaOH aq. was added, and stirred for 1 h. The mixture was concentrated in vacuo and diluted with water. 46 ml of 5N HCl aq. was added with cooling in ice bath, extracted with 500 ml of CHCl$_3$-MeOH (4-1), dried over Na$_2$SO$_4$ and filtered. The filtrate was concentrated to afford a yellow solid. The solid was washed with hexane-CHCl$_3$, filtered and dried under vacuum to afford 8-cyclopropyl-4-methoxyquinoline-2-carboxylic acid.

REFERENCE EXAMPLE 58

4,8-Dimethoxyquinoline-2-carboxylic Acid Potassium Salt

To a solution of 250 mL of methanol and o-anisidine (30.0 g, 0.238 mol), cooled to 3-6° C., was added dropwise dimethyl acetylene dicarboxylate (40.9 g, 0.288 mol) keeping the temperature less than about 10-12° C. The resulting slurry was stirred overnight at room temperature, then 170 mL of H$_2$O were added dropwise. The resulting slurry was aged 2 to 2½ h, then filtered and washed with 120 mL of methanol/H$_2$O (1:1). The solid was dried to give the diester, which was used in the next step. A solution of 80 mL of Eaton's reagent (phosphorous pentoxide, 7.7 wt % solution in methanesulfonic acid) was heated to 50° C., then 20 g of the diester (75.4 mmol) was added in 4-5 portions over 2-3½ h, keeping the reaction temperature between 49-53° C. The reaction was aged at 50° C. from about 3-4 h, then cooled overnight. The resulting mixture was added to a solution of 130 g NaHCO$_3$ in 1 L H$_2$O over 1 h, keeping the temperature between 17-22° C. The resulting slurry was aged for 1½ hours, then filtered, washed with 170 mL of H$_2$O, and dried to give the quinolinone. A solution of quinolinone (25.0 g, 0.107 mol) and methyl iodide (10 mL, 0.161 mol) in 250 mL of DMF was heated to approximately 37° C., and powdered K$_2$CO$_3$ (22.2 g, 0.161 mol) was added. The reaction was aged for 1 hour, then 125 mL of H$_2$O were added, and the mixture was heated to 80° C. for 10-12 h. The resulting slurry was cooled, filtered, washed with 150 mL DMF and dried to give the intended compound.

REFERENCE EXAMPLE 59

6-(1H-tetrazol-5-yl)spiro[chroman-2,4'-piperidine]-4-one Hydrochloride Salt

A mixture of 5-bromo-2-hydroxyacetophenone (104.35 g, 485.26 mmol), N-Boc-piperidin-4-one (98.62 g, 494.96 mmol), 20 mL of pyrrolidine (17.26 g, 242.63 mmol) and 261 mL of MeOH was heated under reflux until the reaction was complete. The mixture was cooled, then 87 mL of H$_2$O were added, and the mixture was filtered and dried to give tert-butyl 6-bromo-4-oxospiro-[chroman-2,4'-piperidine]-1'-carboxylate. Alternatively, 10 mL of pyrrolidine (121.31 mmol) may be used in this procedure. To a solution of tert-butyl 6-bromo-4-oxospiro[chroman-2,4'-piperidine]-1'-carboxylate (6593 g, 16.6 mol) and DMF (33 L) was added Zn(CN)$_2$ (1947 g, 16.6 mol) and Pd(PPh$_3$)$_4$ (192 g, 0.17 mol). The slurry was heated to 90° C. for 3 hours, then cooled to room temperature and filtered. Water (16 L) was added to the filtrate. The resulting slurry was cooled to 5° C., stirred for 1 hour and filtered. The solid was washed with DMF/water (2:1) and dried under vacuum to give tert-butyl 6-cyano-4-oxospiro[chroman-2,4'-piperidine]-1'-carboxylate. A solution of 23 g of tert-butyl 6-cyano-4-oxospiro[chroman-2,4'-piperidine]-1'-carboxylate (67.17 mmol), 13.10 g sodium azide (201.52 mmol), 27.74 g of triethylamine hydrochloride (201.52 mmol), and 460 mL of dry DMF was stirred under a nitrogen atmosphere at 100° C. for 12 hours. After cooling to room temperature, 506 mL of EtOAc were added, followed by 322 mL of 1M HCl (322 mmol). Alternatively, 0.5M HCl may be added until pH=3. The resulting layers were separated, the organic layer was washed with water/methanol (115 ml/46 mL), and then concentrated to give tert-butyl 4-oxo-6-(1H-tetrazol-5-yl)spiro[chroman-2,4'-piperidine]-1'-carboxylate. A solution of 5.08 g of tert-butyl 4-oxo-6-(1H-tetrazol-5-yl)spiro[chroman-2,4'-piperidine]-1'-carboxylate (13.18 mmol), 8.8 mL of 12 M HCl (105.44 mmol) and 8 mL of methanol was heated to 50° C. until the reaction was complete. The resulting slurry was filtered, washed with 25 mL of methanol at room temperature, and dried to give 6-(1H-tetrazol-5-yl)spiro[chroman-2,4'-piperidine]-4-one hydrochloride salt.

REFERENCE EXAMPLE 60

2-(4H-[1,2,4]Triazol-3-yl)-isoindole-1,3-dione

3-Amino-[1,2,4]triazole (8.40 g, 100 mmol) and isobenzofuran-1,3-dione (14.8 g, 100 mmol) were suspended in 1,4-dioxane (200 ml) and heated at 120° C. for 2 days. After the reaction mixture was cooled down at room temperature, the resulting precipitate was filtered, and the cake was washed with H$_2$O then EtOAc to obtain the intended compound as a colorless solid.

REFERENCE EXAMPLE 61

3-Amino-1-(2-Trimethylsilanyl-ethoxymethyl)-1H-[1,2,4]triazole 2-(4H-[1,2,4]Triazol-3-yl)-isoindole-1,3-dione (1.60 g, 7.48 mmol) was dissolved in DMF (16 ml) and NaH (55% in oil, 500 mg, 11.5 mmol) and SEMCl (2.00 g, 12.0 mmol) was added thereto at room temperature. After stirring at 50° C. for 5 h, the reaction mixture was diluted with EtOAc. The mixture was poured into diluted HCl aq. and the organic layer was washed with brine, dried over MgSO$_4$. The desiccant was removed through filtration and the filtrate was concentrated under reduced pressure. The residue was dissolved in THF (16 ml) and MeOH (16 ml), and hydrazine hydrate (561 mg, 11.2 mmol) was added thereto. After stirred at room temperature for 15 h, the mixture was concentrated in vacuo. The residue was suspended in EtOAc and the desiccant was removed through filtration and the filtrate was concentrated under reduced pressure. The residue was purified by silica gel column chromatography (hexane/EtOAc=5/5 to 0/10) to obtain the intended compound as a colorless solid.

REFERENCE EXAMPLE 62

1'-[(4,8-dimethoxyquinolin-2-yl)carbonyl]-6-[1-(2-trimethylsilanyl-ethoxymethyl)-1H-[1,2,4]triazol-3-ylamino]spiro[chroman-2,4'-piperidin]-4-one The intended compound was produced according to the procedure (Method 9) described in reference Example 52 but using 3-amino-1-(2-Trimethylsilanyl-ethoxymethyl)-1H-[1,2,4]triazol in place of 1-(2-trimethylsilanyl-ethoxymethyl)-piperazin-2-one.

REFERENCE EXAMPLE 63

5-{1'-[(1-cyclopropyl-5-methoxyisoquinolin-7-yl)carbonyl]-4-oxospiro[chroman-2,4'-piperidin]-6-yl}nicotinic acid

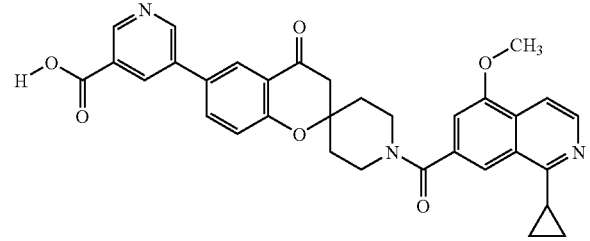

The compound was prepared according to the procedure described in Example 36 but using 1-[(1-cyclopropyl-5-methoxy-isoquinolin-7-yl)carbonyl]-1H-imidazole instead of (8-cyclopropyl-4-methoxy-quinolin-2-yl)-imidazol-1-yl-methanone. $^1$H-NMR (400 MHz, DMSO-d$_6$) δ: 9.03-8.99 (2H, m), 8.40-8.37 (1H, m), 8.36 (1H, d, J=5.9 Hz), 8.08-8.02 (3H, m), 7.73 (1H, d, J=5.9 Hz), 7.25 (1H, d, J=9.5 Hz), 7.19 (1H, s), 4.40-4.28 (1H, br m), 4.01 (3H, s), 3.64-3.18 (3H, m), 3.00-2.86 (1H, m), 2.96 (2H, s), 2.17-2.03 (1H, br m), 1.99-1.79 (3H, m), 1.16-1.01 (4H, m). MS [M+H]+=564.

The usefulness of the compounds of the invention as medicines is demonstrated, for example, by the following pharmacological test example.

BIOLOGICAL ASSAYS

A. Pharmacological Test Example

Acetyl CoA Carboxylase (ACC) Activity Inhibition Test

A test compound is dissolved in dimethyl sulfoxide (DMSO) to a concentration of 10 mM and then diluted with DMSO to give a 100-fold concentrated solution of the compound compared with target assay concentration. The ACC enzyme activity inhibition test is carried out according to a modification of Thampy & Wakil's method (*J. Biol. Chem., Vol.* 260, pp. 6318-6323 (1985)). Concretely, 0.8 µl of the diluted test compound is added to each well of 96-well assay plate (Perkin Elmer Opti Plate), then 40 µl of a substrate solution (50 mM Hepes sodium (pH 7.5), 2 mM DTT, 10 mM ATP, 500 µM acetyl CoA, 0.17 mM NaH[$^{14}$C]O$_3$ (58 mCi/mmol, by Amersham), 8 mM NaHCO$_3$) is added to each well, and 40 µL of an enzyme solution (1 to 2 nM human ACC1 or human ACC2, 50 mM Hepes sodium (pH 7.5), 2 mM DTT, 40 mM MgCl$_2$, 40 mM tripotassium citrate 1 mg/ml fetal bovine serum albumin) is added thereto. Then, the upper side of the plate is sealed up, and the plate is incubated with gently stirring at 37° C. for 40 minutes. Next, 20 µl of 1 N HCl is added to each well to stop the enzyme reaction, and the assay plate is stirred overnight to remove the unreacted NaH[$^{14}$C]O$_3$. Next, 100 µl of a scintillator (Perkin Elmer's Microscinti 40) is added to each well and the plate is stirred, then the radioactivity of the fixed [$^{14}$C] is counted using a microplate scintillation counter (Perkin Elmer's Topcount), the radioactivity of which represents the enzyme activity in each well. The human ACC1 and human ACC2 enzyme-inhibition activities of the test compounds are calculated, based on the radioactivity of the well added by DMSO without test compound as a control.

The compounds of the invention were tested according to this method and the compounds tested all inhibited both ACC1 and ACC2. The results are shown in the following Table.

TABLE

| Inhibition (%) by 1 µmol/liter Chemical | | |
|---|---|---|
| Compound | human ACC1 | human ACC2 |
| Example 2 | 82% | 85% |
| Example 3 | 100% | 98% |
| Example 4 | 93% | 96% |
| Example 5 | 97% | 97% |
| Example 10 | 100% | 99% |
| Example 18 | 97% | 99% |
| Example 21 | 99% | 97% |
| Example 27 | 101% | 100% |

Representative compounds of the present invention, including the compounds of Examples 1-85 were tested in the above assay and found to have a percent inhibition of greater than or equal to 50% for ACC-1 and a percent inhibition of greater than or equal to 50% for ACC-2 in the acetyl CoA carboxylase (ACC) activity inhibition test.

B. Effect of ACC1/2 Inhibitor on In Vivo Body Weight Fat Mass, Fatty Liver and Plasma Glucose Levels Effect of ACC1/2 inhibitor on body weight, fat mass, fatty liver and plasma glucose level can be determined in either high fat diet induced obese or KKAy diabetic mice.

Male C57black/6J mice at approximately 6 weeks old are individually housed and maintained on chow diet for 2 weeks prior to the study. Then the mice are fed with a 60% fat diet for 5 weeks before dosing. The mice (n=8) on the high fat diet are orally dosed with either vehicle control (0.5% methylcellulose solution) or an ACC1/2 inhibitor (various doses) for 6 weeks. Body weight is determined on a daily basis and fat mass is measured by NMR every other week. Hepatic triglyceride content is determined at week 6. Effective ACC1/2 inhibitors result reduced body weight gain, reduced fat mass gain, and reduced hepatic triglyceride content in ACC1/2 inhibitor treated male C57black/6J mice in contrast to the vehicle control group.

Male KKAy mice at approximately 8 weeks old are individually housed and maintained on for 2 weeks prior to the study. The mice (n=10) are orally dosed with either vehicle control (0.5% methylcellulose solution) or an ACC1/2 inhibitor (various doses) for 2 weeks. At week 2, blood is collected at 23 hours post dose and plasma glucose concentration is determined. Effective ACC1/2 inhibitors result in reduced plasma glucose levels in ACC1/2 inhibitor treated KKAy mice in contrast to the vehicle control group.

C. Human Study for Effect on Food Intake and Glucose/Insulin Levels 800 people with a BMI≧30 who have impaired fasting plasma glucose levels, impaired glucose tolerance, or elevated serum insulin, indicative of a prediabetic insulin resistant state, and who may have elevated serum glucose levels, indicative of type II diabetes, are advised to diet and increase their physical activity. After a two-week placebo run-in period, which includes a standardized program of diet, physical activity, and lifestyle changes, the patients are randomized into 2 treatment groups: placebo; and an effective dose of a compound of formula (I). The compound of formula (I) is given once or more per day, as previously determined to be effective. Patients are treated for 6 months, body weights are measured biweekly, and appetite, hunger, satiety are measured weekly using standard questionnaires. Serum glucose, insulin levels and body weight are determined at day 0, monthly, and after the final dose.

Effective compounds result in body weight loss or an improvement in serum insulin levels, indicative of improved insulin sensitivity or lower fasting blood glucose levels.

FORMULATION PREPARATION EXAMPLE 1

20.0 g of the compound of Example 1, 417 g of lactose, 80 g of crystalline cellulose and 80 g of partially-alphatized starch are mixed in a V-shape mixer, and 3.0 g of magnesium stearate is added to it and mixed. The mixture powder is tabletted according to an ordinary method to obtain 3000 tablets each having a diameter of 7.0 mm and a weight of 150 mg.

Ingredients of Tablet (150 mg

| Ingredients of Tablet (150 mg) | |
|---|---|
| Compound of Example 1 | 5.0 mg |
| Lactose | 104.25 mg |
| Crystalline cellulose | 20.0 mg |
| Partially-alphatized starch | 20.0 mg |
| Magnesium stearate | 0.75 mg |

FORMULATION PREPARATION EXAMPLE 2

10.8 g of hydroxypropyl cellulose 2910 and 2.1 g of polyethylene glycol 6000 are dissolved in 172.5 g of pure water, and 2.1 g of titanium oxide is dispersed therein to prepare a coating-liquid. Using a high-coater-mini, 2500 tablets of Preparation Example 1 that is prepared separately is sprayed with the coating liquid to obtain film-coated tables each having a weight of 155 mg.

Ingredients of Tablet (155 mg)

| Ingredients of Tablet (155 mg) | |
|---|---|
| Tablet of Preparation Example 1 | 150 mg |
| Hydroxypropyl cellulose 2910 | 3.6 mg |
| Polyethylene glycol 6000 | 0.7 mg |
| Titanium dioxide | 0.7 mg |

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

What is claimed is:

1. A method for the treatment of, insulin resistance in a subject in need thereof which comprises administering to said subject a therapeutically effective amount of a compound of formula (I):

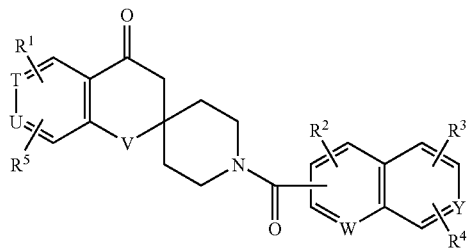

(I)

wherein $R^1$ and $R^5$ each independently represent a hydrogen atom, a halogen atom, a cyano group, a lower alkenyl group, a lower alkoxy group, a lower alkanoyl group, a lower alkoxycarbonyl group, an aralkyloxycarbonyl group, a carbamoyl-lower alkoxy group, a carboxy-lower alkenyl group, or a group of $-Q^1-N(R^a)-Q^2-R^b$, a lower alkyl group optionally substituted by a substituent selected from a group consisting of a halogen atom, a hydroxyl group, an azido group, a lower alkoxy group, a halo-lower alkoxy group, a lower alkylthio group, a lower alkanoyloxy group, a carboxyl group, a carbamoyl group, a lower alkoxycarbonyl group and a lower alkylsulfonyl group, an aryl or heterocyclic group optionally substituted by a substituent selected from a group consisting of a halogen atom, a hydroxyl group, an oxo group, a thioxo group, a lower alkyl group, a halo-lower alkyl group, a hydroxy-lower alkyl group, a lower alkanoyloxy-lower alkyl group, a lower alkoxy group, a halo-lower alkoxy group, a formyl group, a carboxyl group, a lower alkanoyl group, a lower alkoxycarbonyl group, a lower alkylsulfonyl group and a group of $-CO-N(R^c)R^d$, or a lower alkyl or alkenyl group having the said aryl or heterocyclic group;

$R^2$, $R^3$ and $R^4$ each independently represent a hydrogen atom, a halogen atom, a hydroxyl group, a nitro group, a cyano group, a cyclo-lower alkyl group, a lower alkenyl group, a lower alkoxy group, a halo-lower alkoxy group, a hydroxy-lower alkoxy group, a lower alkoxy-lower alkoxy group, a cyclo-lower alkyloxy group, a cyclo-lower alkyl-lower alkoxy group, a lower alkylthio group, a group of $-O-R^k$ or a group of $-N(R^e)R^f$, or a lower alkoxy group substituted by the group of $-N(R^e)R^f$, or a lower alkyl group optionally substituted by a substituent selected from a group consisting of a halogen atom, a hydroxyl group and a cyclo-lower alkyl group, or an aryl or heteroaromatic group optionally substituted by a substituent selected from a group consisting of a halogen atom, a nitro group, a hydroxyl group, a lower alkyl group, a halo-lower alkyl group, a hydroxy-lower alkyl group, a cyclo-lower alkyl group, a lower alkenyl group, a lower alkoxy group, a halo-lower alkoxy group and a lower alkylthio group;

$Q^1$ and $Q^2$ each independently represent a single bond, or a group of $-CO-$, $-SO_2-$ or $-C(R^g)(R^h)-$, when $Q^2$ represents the group of $-C(R^g)(R^h)-$, $R^a$ and $R^g$, taken together, may represent a group of $-Q^1-N=C(R^h)-R^b$;

$R^a$ and $R^b$ each independently represent a hydrogen atom, a lower alkenyl group, a lower alkoxy group, a halo-lower alkoxy group, an aralkyloxy group, a carbamoyl group, a lower alkoxycarbonyl group or a group of $-N(R^i)R^j$, or a lower alkyl group optionally substituted by a substituent selected from a group consisting of a halogen atom, a lower alkoxy group, a carbamoyl group and a lower alkoxycarbonyl group, or a heteroaromatic group optionally substituted by a lower alkyl group that is optionally substituted by a substituent selected from a group consisting of a halogen atom, a lower alkoxy group, a carbamoyl group and a lower alkoxycarbonyl group;

$R^c$, $R^d$, $R^g$, $R^h$, $R^i$ and $R^j$ each independently represent a hydrogen atom, a lower alkyl group, or a halo-lower alkyl group;

$R^e$ and $R^f$ each independently represent a hydrogen atom, a lower alkyl group or a halo-lower alkyl group, or taken together, they may form a lower alkylene group optionally interrupted by an oxygen atom, a sulfur atom or an imino group;

$R^k$ represents a pyrrolidinyl, tetrahydrofuranyl, piperidyl group optionally substituted by a lower alkyl group or a halo-lower alkyl group;

T, U and W are each methine;

Y is a nitrogen atom; and

V represents an oxygen atom;

or a pharmaceutically acceptable salt or ester thereof.

2. The method of claim 1, wherein the compound of formula I is selected from the group consisting of:

5-{1'-[(1-Cyclopropyl-5-methoxyisoquinolin-7-yl)carbonyl]-4-oxo-spiro[chromane-2,4'-piperidin]-6-yl}nicotinic acid;

Methyl 5-{1'-[(1-cyclopropyl-5-methoxyisoquinolin-7-yl)carbonyl]-4-oxo-spiro[chromane-2,4'-piperidin]-6-yl}nicotinate;

sodium 5-{1'-[(1-cyclopropyl-5-methoxyisoquinolin-7-yl)carbonyl]-4-oxo-spiro [chromane-2,4'-piperidin]-6-yl}-2-fluorobenzoate;

sodium 2-{1'-[(8-cyclopropyl-4-ethoxyquinolin-2-yl)carbonyl]-4-oxo-spiro [chromane-2,4'-piperidin]-6-yl}isonicotinate; and sodium 4-{1'-[(1-cyclopropyl-5-methoxyisoquinolin-7-yl)carbonyl]-4-oxo-spiro [chromane-2,4'-piperidin]-6-yl}pyridine-2-carboxylate.

\* \* \* \* \*